US008318960B2

(12) United States Patent
Gandelman et al.

(10) Patent No.: US 8,318,960 B2
(45) Date of Patent: Nov. 27, 2012

(54) DIARYLPHOSPHINE- AND DIALKYLPHOSPHINE-CONTAINING COMPOUNDS, PROCESSES OF PREPARING SAME AND USES THEREOF AS TRIDENTATE LIGANDS

(75) Inventors: Mark Gandelman, Kfar-Saba (IL); Elaine Melissa Schuster, Haifa (IL); Gennady Nisnevich, Haifa (IL)

(73) Assignee: Technion Research & Development Foundation Ltd., Haifa (IL)

( * ) Notice: Subject to any disclaimer, the term of this patent is extended or adjusted under 35 U.S.C. 154(b) by 90 days.

(21) Appl. No.: 12/779,093

(22) Filed: May 13, 2010

(65) Prior Publication Data

US 2010/0292084 A1 Nov. 18, 2010

Related U.S. Application Data

(63) Continuation-in-part of application No. 12/465,719, filed on May 14, 2009.

(60) Provisional application No. 61/178,114, filed on May 14, 2009.

(51) Int. Cl.
C07F 9/02 (2006.01)
(52) U.S. Cl. .......................................................... 552/3
(58) Field of Classification Search .................. 552/3
See application file for complete search history.

(56) References Cited

U.S. PATENT DOCUMENTS

2010/0292100 A1 11/2010 Gandelman et al.

FOREIGN PATENT DOCUMENTS

WO WO 2008/145976 12/2008

OTHER PUBLICATIONS

Moedritzer et al. CAS: 57:1831, 1962.*
Hoffman et al. CAS: 24:37243, 1930.*
Kabachnik et al. CAS: 57:23310, 1962.*
Grinshtein et al. CAS: 56: 7769, 1962.*
Grinshtein et al. CAS: 64: 93586, 1966.*
Anteunis et al. CAS: 64: 35992, 1966.*
Petrov et al. CAS: 64: 35984, 1966.*
Chance et al. CAS: 66: 105019, 1967.*
Response Dated Dec. 12, 2011 to Official Action to Oct. 11, 2011 From the US Paten and Trademark Office Re. U.S. Appl. No. 12/465,719.
Official Action Dated Oct. 11, 2011 From the US Paten and Trademark Office Re. U.S. Appl. No. 12/465,719.
Buckler et al. "Reactions of Phosphine With Aliphatic Aldehydes", Journal of the American Chemical Society, JACS, 83: 168-173, Jan. 5, 1961.
Degl'Innocenti et al. "Azide Cyclizations With Acetylenic Silyl Ketone: A General Access to Functionalized-1,2,3-Triazolylacylsilanes and Aldhydes", Tetrahedron Letters, 36(49): 9031-9034, 1995.
Detz et al "'Clickphine': A Novel and Highly Versatile P,N. Ligand Class Via Click Chemistry", Organic Letters, 8(15): 3227-3230, Jun. 27, 2006.
Dolhem et al "Modular Synthesis of ChiraClick Ligands: A Library of P-Chirogenic Phosphines", Journal of Combinatorial Chemistry, 9(3): 477-486, Mar. 10, 2007.
Kolb et al "Click Chemistry: Diverse Chemical Function From A Few Good Reactions", Angwandte Chemie International Edition, 40: 2005-2021, 2004.
Morales-Morales "Pincer Complexes. Applications in Catalysis", Revista de la Sociedad Química de México, 48(4): 338-346, 2004.
Rostovtsev et al "A Stepwise Huisgen Cycloaddition Process: Copper(I)-Catalyzed Regioselective 'Ligation' of Azides and Terminal Alkynes", Angewndte Chemie International Edition, 41(14): 2596-2599, 2002.
Schuster et al "Pincer Click Ligands", Angewandte Chemie International Edition, 47: 4555-4558, 2008.
Schuster et al. "Synthesis of Novel Bulky, Electron-Rich Propargyl and Azidomethyl Dialkyl Phosphines and Their Use in the Preparation of Pincer Click Ligands", Organometallics, 28(17): 5025-5031, Aug. 5, 2009. Abstract.
Schuster et al. "Versatile, Selective, and Switchable Coordination Modes of Pincer Click Ligands", Organometallics, 28(24): 7001-7005, Nov. 13, 2009.
Official Action Dated Jan. 17, 2012 From the US Paten and Trademark Office Re. U.S. Appl. No. 12/465,719.

* cited by examiner

Primary Examiner — Rei-tsang Shiao

(57) ABSTRACT

A novel process of preparing tridentate ligands containing one or more of a diarylphosphine and/or dialkylphosphine electron donating groups are disclosed. Use of this process for preparing a combinatorial library of such tridentate ligands and of organometallic complexes containing same is also disclosed. Further disclosed are novel diarylphosphine-containing and dialkylphosphine-containing compounds that can serve as tridentate ligands (e.g., pincer ligands), combinatorial libraries of such tridentate ligands, organometallic complexes containing these ligands (e.g., pincer complexes), and combinatorial libraries of such complexes. Methods utilizing these libraries for screening for candidate organometallic catalysts are also disclosed. Novel precursor molecules useful for preparing the tridentate ligands and processes of preparing same are also disclosed.

4 Claims, 9 Drawing Sheets

3a: Ar = C₆H₅
3b: Ar = o-MeOC₆H₄
i: CuSO₄/Na Ascorbate, THF/H₂O, 23°C, 24h
ii: DABCO, 70°C, 5h, for 5, 6, 7. HSiCl₃/NEt₃, 120°C, 12h for 7, 8.

5, 9: $D^1 = D^2 = PPh_2$
6, 10: $D^1 = PPh_2$, $D^2$ = pyridine
7, 11: $D^1 = PhS$, $D^2 = PPh_2$
8, 12: $D^1 = PhS$, $D^2 = P(o-MeOC_6H_4)_2$

14a R=*i*Pr
14b R=Cy

15a R=*i*Pr
15b R=Cy (i) TMS-C≡CCH₂MgBr, 48h, r.t. (ii) NH₄F, MeOH, 18h, r.t.

*i*Pr = isopropyl; Cy = cyclohexyl; *t*Bu = *t*-butyl; Bn = benzyl (i) CuSO4/Na Ascorbate, THF/H2O, 23 °C, 24h
(ii) PhSiH3, 110 °C, 12h for 25, 27. MeOH/dioxane/4Å mol sieves, 110 °C, 18h for 24, 25, 26, 27.

DIARYLPHOSPHINE- AND DIALKYLPHOSPHINE-CONTAINING COMPOUNDS, PROCESSES OF PREPARING SAME AND USES THEREOF AS TRIDENTATE LIGANDS

RELATED APPLICATION/S

The instant application is a continuation-in-part (CIP) of U.S. patent application Ser. No. 12/465,719 filed May 14, 2009. The instant application also claims the benefit of priority from U.S. Provisional Patent Application No. 61/178,114 filed May 14, 2009. The contents of the above applications are incorporated herein by reference in their entirety.

FIELD AND BACKGROUND OF THE INVENTION

The present invention, in some embodiments thereof, relates to novel compounds, methods of preparing same, metal complexes formed therewith and uses thereof and, more particularly, but not exclusively, to novel dialkylphosphine-containing compounds and diarylphosphine-containing compounds that can be utilized for forming a library of tridentate ligands, such as, for example, pincer-type ligands, to methods of synthesizing these compounds and ligands, to uses thereof in, for example, the preparation of organometallic complexes and to the various uses of such organometallic complexes.

Organophosphorus compounds have enjoyed a variety of important applications in numerous actively developing fields of science and technology. Organophosphorus compounds have found use as agricultural insecticides, anti-corrosion and fire-resistant agents, extractants in hydrometallurgy and as antimicrobial and chemotherapeutic agents.

In addition, phosphorus-containing compounds have received special attention due to their spectacular applications in synthetic chemistry both as reagents and ligands for metal-based catalysis. From a synthetic point of view, phosphorus-containing precursors decorated with versatile functional groups are especially valuable, particularly if these groups can be easily interconverted and further diversified.

One of the most interesting synthetic applications of organophosphorus compounds is the formation of tridentate pincer type ligands, also referred to herein and in the art as "pincer ligands".

A pincer ligand is a type of a chelating agent that can bind tightly to three adjacent coplanar sites, usually on a transition metal. Typical tridentate pincer type ligands have the general form $D_1CD_2$, wherein C is a carbon atom that can potentially interact with a metal; and $D_1$ and $D_2$ are groups containing coordinating atoms (also referred to herein as electron donating atoms). In most pincer ligands, the carbon atom forms a part of an aryl ring, typically phenyl. The carbon atom can be replaced by other coordinating atoms such as nitrogen or sulfur, which typically form a part of a heterocyclyl such as a heteroaryl.

Many useful pincer ligands contain phosphines. Early examples of pincer ligands are anionic ligands with a carbanion as the central donor site and flanking phosphine donors. Such ligands are referred to in the art as PCP pincers. Other pincer ligands include, for example, PNP, SCS, NCN, PCS, PCN, PNN, and NNN.

The assumed irreversibility of pincer-metal interaction confers high thermal stability to the resulting complexes. This stability is ascribed to the constrained geometry of the pincer ligand and steric shielding provided to the metal center by substituents of the coordinated donor groups.

Stoichiometric and catalytic applications of pincer complexes have been studied at an accelerating pace since the mid 1970's, especially for C—H activation.

Tridentate pincer type ligands have found spectacular employment in coordination, mechanistic, synthetic and supramolecular chemistry, along with nanoscience and the development of sensors and molecular switches. Most significantly, a realization that pincer ligands offer both a unique, highly protective environment for the coordinated metal center and opportunities to fine tune the steric and electronic metal properties has generated extensive research into the use of these complexes as catalysts [For reviews, see: J. T. Singleton, *Tetrahedron* 2003, 59, 1837; and D. Morales-Morales, *Rev. Quim. Mex.* 2004, 48, 338]. As a result, many important and challenging catalytic processes have been developed based on such systems.

It is generally accepted that the reactivity, selectivity and catalytic performance of pincer-based systems greatly relies on the characteristics of the donor groups D in the carefully selected ligand. These characteristics depend on the type of the coordinating atom, and further on the nature of its organic substituents.

Catalytic groundbreaking processes such as dehydrogenation of saturated hydrocarbons and dehydrogenative coupling of alcohols with amines [Gunanathan, C.; Ben-David, Y.; Milstein, D. Science 2007, 317, 790] have been developed on the basis of pincers bearing bulky electron-donating phosphorus substituents.

Pincer-type ligands based on bulky, electron-donating phosphines are therefore advantageous for numerous important applications.

Traditionally, pincer ligands are prepared by attaching electron donating atoms, or groups containing the same, to a ligand backbone.

Optimization of tailor-made catalysts therefore includes extensive experimental investigations, in which laborious ligand synthesis is often a serious bottleneck. Especially, synthesis of non-symmetrically substituted $D^1CD^2$ ligands ($D^1$ and $D^2$ are different groups) represents a considerable challenge, as their preparation usually includes series of steps and separations which commonly result in low yields.

The preparation of mono-phosphine and chiral phosphine ligand libraries, using the "click" reaction has recently been reported [Q. Dai, W. Gao, D. Liu, L. M. Kapes, X. Zhang, *J. Org. Chem.* 2006, 71, 3928; R. D. Detz, S. Heras, R. de Gelder, P. W. N. M. van Leeuwen, H. Hiemstra, J. N. H. Reek, J. H. van Maarseveen *Org. Lett.* 2006, 8, 3227; F. Dolhem, M. J. Johansson, T. Antonsson, N. Kann, *J. Comb. Chem.* 2007, 9, 477.

The "click" reaction is a name used to describe a Cu(I)-catalyzed stepwise variant of the Huisgen 1,3-dipolar cycloaddition of azides and alkynes to yield 1,2,3-triazole. This reaction is carried out under ambient conditions and with exclusive regioselectivity for the 1,4-disubstituted triazole product when mediated by catalytic amounts of Cu(I) salts [V. Rostovtsev, L. G. Green, V. V. Fokin, K. B. Sharpless, *Angew. Chem. Int. Ed.* 2002, 41, 2596; H. C. Kolb, M. Finn, K. B. Sharpless, *Angew Chem., Int. Ed.* 2001, 40, 2004.

Pincer ligands based on alkyl-substituted phosphines have recently demonstrated broad use in the elucidation of elusive species [For representative examples, see: (a) van Koten, G.; Timmer, J. G.; Noltes, J. G.; Spek, A. L. *J. Chem. Soc., Chem. Commun.* 1978, 250. (b) Albrecht, M; Spek, A. L.; van Koten, G. *J. Am. Chem. Soc.* 2001, 123, 7233. (c) Gandelman, M.; Rybtchinski, B.; Ashkenazi, N.; Gauvin, R. M.; Milstein, D. *J. Am. Chem. Soc.* 2001, 123, 5372. (d) Vigalok, A.; Milstein, D. *Acc. Chem. Res.* 2001, 34, 798. (e) Poverenov, E.; Efremenko, I.; Frenkel, A.; Ben-David, Y.; Shimon, L. J. W.; Leitus, G.; Konstantinovski, L.; Martin, J. M. L.; Milstein, D. *Nature* 2008, 455, 1093.].

While a myriad of di-substituted phosphine ligands have been described in the art, the synthesis of dialkyl-substituted phosphine compounds such as, for example, dialkyl substituted propargyl, azidomethyl, bromomethyl, and carboxymethyl phosphine species, has not been described hitherto, with the exception of dialkylphosphinyl acetic acids [Dolhem, F; Johansson, M. J.; Antonsson, T.; Kann, N. *Synlett* 2006, 20, 3389].

SUMMARY OF THE INVENTION

The present inventors have devised and successfully practiced a novel, general process for a selective and facile preparation of both symmetrically and non-symmetrically substituted tridentate ligands of the $D^1CD^2$ type, based on a triazole core and a diarylphosphine-containing moiety. The present inventors have further utilized these tridentate ligands for forming well-defined transition metal complexes and have further demonstrated the catalytic activity of the formed complexes.

The present inventors have further devised and successfully practiced novel methods for preparing azides and alkynes bearing dialkylphosphine moieties, which are particularly suitable for being utilized for forming a novel family of dialkylphosphine-containing tridentate ligands. As discussed hereinabove, substituted phosphine-containing tridentate ligands, bearing one or more bulky, electron donating groups, have recently been recognized and highly advantageous in a myriad of applications.

The methodology described herein is conceptually and generally depicted in FIG. 1, and is based upon the Sharpless-modified Huisgen [2+3] cycloaddition of alkynes and azides (the "click" reaction), forming triazoles, as the central building tool for ligand assembly [Huisgen, R. *Proc. Chem. Soc.* 1961, 357]. Thus, a variety of azides and alkynes decorated with a dialkylphosphine or diarylphosphine donating group, as well as with other electron donating groups, are reacted to give a triazole-based pincer frame with two donor arms in 1,4-positions and a relatively acidic hydrogen that allows for metal insertion to form tridentate pincer-type complexes.

The present inventors have shown that by utilizing the "click chemistry" described herein, combinatorial synthesis of non-trivial ligands from relatively simple building blocks is effected and advantageously allows for efficient preparation and screening of a broad range of organometallic catalysts for a variety of synthetic applications.

The novel methodology described herein allows for efficient and facile preparation of an entirely novel family of tridentate ligands of the $D^1CD^2$ type, and can be advantageously utilized for creating combinatorial libraries of, for example, tridentate pincer ligands.

According to an aspect of some embodiments of the present invention there is provided a compound of the general Formula I:

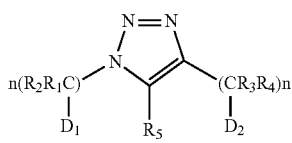

Formula I wherein:
n is an integer from 1 to 4;
$R_1$-$R_4$ are each independently selected from the group consisting of hydrogen, alkyl, cycloalkyl, aryl, heteroaryl, heteroalicyclic, alkoxy, thioalkoxy, hydroxy, thiol, amine, nitro and cyano;

$R_5$ is a leaving group capable of being dissociated so as to form a carbanion;

$D_1$ is a first electron donating group of the general Formula IIa:

$$Z_1Z_2Xa \qquad \text{Formula IIa;}$$

and $D_2$ is a second electron donating group of the general Formula IIb:

$$Z_3Z_4Xb \qquad \text{Formula IIb;}$$

whereas:

Xa and Xb are each independently an electron donating atom; and $Z_1$, $Z_2$, $Z_3$ and $Z_4$ are each independently absent or a substituent selected from the group consisting of substituted or non-substituted aryl, substituted or non-substituted alkyl, substituted or non-substituted alkoxy and substituted or non-substituted aryloxy, or, alternatively, at least two of $Z_1$, $Z_2$, $R_1$ and $R_2$ and/or at least two of $Z_3$, $Z_4$, $R_3$ and $R_4$ form together a five- or six-membered heteroalicyclic or heteroaromatic ring, at least one of the $D_1$ and $D_2$ having the general Formula IIa or IIb, respectively, is being such that the electron donating atom is phosphorus and either the $Z_1$ and $Z_2$ or the $Z_3$ and $Z_4$ substituents of the phosphorus are each independently a substituted or non-substituted aryl, or, alternatively, at least one of the $D_1$ and $D_2$ having the general Formula IIa or IIb, respectively, is being such that the electron donating atom is phosphorus and at least one of the $Z_1$ and $Z_2$ or the $Z_3$ and $Z_4$ substituents of the phosphorus is a substituted or non-substituted alkyl or a substituted or non-substituted cycloalkyl.

According to an aspect of some embodiments of the present invention there is provided a process of preparing the compound described above, the process comprising:

reacting, via a 1,3-dipolar cycloaddition reaction, a compound having general Formula IIIa:

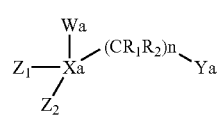

Formula IIIa with a compound having general Formula IIIb:

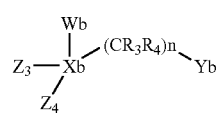

Formula IIIb wherein:
Wa and Wb are each independently a protecting group or absent;
Ya is a —$N_3$ group;
Yb is a —C≡C—$R_5$ group;
n is the abovementioned integer from 1 to 4;
$R_1$-$R_4$ are each independently selected from the group consisting of hydrogen, alkyl, cycloalkyl, aryl, heteroaryl, heteroalicyclic, alkoxy, thioalkoxy, hydroxy, thiol, amine, halogen, nitro and cyano;
$R_5$ is the leaving group;
Xa and Xb are each independently the electron donating atom; and $Z_1$, $Z_2$, $Z_3$ and $Z_4$ are each independently absent or the substituent selected from the group consisting of substituted or non-substituted aryl, substituted or non-substituted alkyl, substituted or non-substituted alkoxy and substituted or non-substituted aryloxy, or, alternatively, at least two of $Z_1$, $Z_2$, $R_1$ and $R_2$ and/or at least two of $Z_3$, $Z_4$, $R_3$ and $R_4$ form together a five- or six-membered heteroalicyclic or heteroaromatic ring, at least one of the $D_1$ and $D_2$ having the general Formula IIa or IIb, respectively, is being such that the electron donating atom is phosphorus and either the $Z_1$ and $Z_2$ or the $Z_3$ and $Z_4$ substituents of the phosphorus are each independently a substituted or non-substituted aryl, or, alternatively, at least one of the $D_1$ and $D_2$ having the general Formula IIa or IIb, respectively, is being such that the electron donating atom is phosphorus and at least one of the $Z_1$ and $Z_2$ or the $Z_3$ and $Z_4$ substituents of the phosphorus is a substituted or non-substituted alkyl or a substituted or non-substituted cycloalkyl.

According to an aspect of some embodiments of the present invention there is provided a combinatorial library of tridentate ligands, the library comprising a plurality of compounds having the general Formula I:

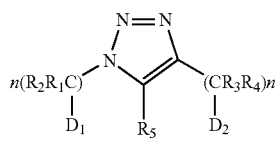

Formula I wherein:

n is an integer from 1 to 4;

$R_1$-$R_4$ are each independently selected from the group consisting of hydrogen, alkyl, cycloalkyl, aryl, heteroaryl, heteroalicyclic, alkoxy, thioalkoxy, hydroxy, thiol, amine, nitro and cyano;

$R_5$ is a leaving group capable of being dissociated so as to form a carbanion;

$D_1$ is an electron donating group of the general Formula IIa:

 Formula IIa;

and $D_2$ is an electron donating group of the general Formula IIb:

 Formula IIb;

whereas:

Xa and Xb are each independently an electron donating atom; and $Z_1$, $Z_2$, $Z_3$ and $Z_4$ are each independently absent or a substituent selected from the group consisting of substituted or non-substituted aryl, substituted or non-substituted alkyl, substituted or non-substituted alkoxy and substituted or non-substituted aryloxy, or, alternatively, at least two of $Z_1$, $Z_2$, $R_1$ and $R_2$ and/or at least two of $Z_3$, $Z_4$, $R_3$ and $R_4$ form together a five- or six-membered heteroalicyclic or heteroaromatic ring, at least one of the $D_1$ and $D_2$ having the general Formula IIa or IIb, respectively, is being such that the electron donating atom is phosphorus and either the $Z_1$ and $Z_2$ or the $Z_3$ and $Z_4$ substituents of the phosphorus are each independently a substituted or non-substituted aryl, or, alternatively, at least one of the $D_1$ and $D_2$ having the general Formula IIa or IIb, respectively, is being such that the electron donating atom is phosphorus and at least one of the $Z_1$ and $Z_2$ or the $Z_3$ and $Z_4$ substituents of the phosphorus is a substituted or non-substituted alkyl or a substituted or non-substituted cycloalkyl, the compounds being different from one another in at least one of the electron donating groups D1 and D2 and/or at least one of the aforementioned n and $R_1$-$R_5$.

According to an aspect of some embodiments of the present invention there is provided an organometallic complex comprising a metal and a compound described hereinabove serving as a tridentate ligand being in complex with the metal, the organometallic complex having general Formula V:

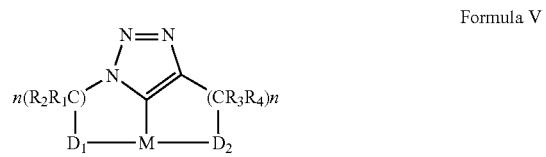

Formula V wherein:

n is the aforementioned integer from 1 to 4;

$R_1$-$R_4$ are each independently selected from the group consisting of hydrogen, alkyl, cycloalkyl, aryl, heteroaryl, heteroalicyclic, alkoxy, thioalkoxy, hydroxy, thiol, amine, halogen, nitro and cyano;

M is a transition metal;

$D_1$ is the electron donating group of the general Formula IIa:

 Formula IIa;

and $D_2$ is an electron donating group of the general Formula IIb:

 Formula IIb, whereas:

Xa and Xb are each independently the electron donating atom; and $Z_1$, $Z_2$, $Z_3$ and $Z_4$ are each independently absent or a substituent selected from the group consisting of substituted or non-substituted aryl, substituted or non-substituted alkyl, substituted or non-substituted alkoxy and substituted or non-substituted aryloxy, or, alternatively, at least two of $Z_1$, $Z_2$, $R_1$ and $R_2$ and/or at least two of $Z_3$, $Z_4$, $R_3$ and $R_4$ form together a five- or six-membered heteroalicyclic or heteroaromatic ring, at least one of the $D_1$ and $D_2$ having the general Formula IIa or IIb, respectively, is being such that the electron donating atom is phosphorus and either the $Z_1$ and $Z_2$ or the $Z_3$ and $Z_4$ substituents of the phosphorus are each independently a substituted or non-substituted aryl, or, alternatively, at least one of the $D_1$ and $D_2$ having the general Formula IIa or IIb, respectively, is being such that the electron donating atom is phosphorus and at least one of the $Z_1$ and $Z_2$ or the $Z_3$ and $Z_4$ substituents of the phosphorus is a substituted or non-substituted alkyl or a substituted or non-substituted cycloalkyl.

According to an aspect of some embodiments of the present invention there is provided a process of preparing the organometallic complex described above, the process comprising contacting a salt or a complex of the metal with a compound having general Formula I:

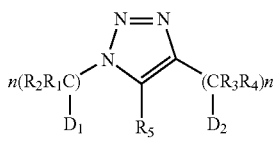

Formula I wherein:

n is an integer from 1 to 4;

$R_1$-$R_4$ are each independently selected from the group consisting of hydrogen, alkyl, cycloalkyl, aryl, heteroaryl, heteroalicyclic, alkoxy, thioalkoxy, hydroxy, thiol, amine, nitro and cyano;

$R_5$ is a leaving group capable of being dissociated so as to form a carbanion;

$D_1$ is an electron donating group of the general Formula IIa:

$$Z_1Z_2Xa \qquad \text{Formula IIa;}$$

and $D_2$ is an electron donating group of the general Formula IIb:

$$Z_3Z_4Xb \qquad \text{Formula IIb;}$$

whereas:

Xa and Xb are each independently an electron donating atom; and $Z_1$, $Z_2$, $Z_3$ and $Z_4$ are each independently absent or a substituent selected from the group consisting of substituted or non-substituted aryl, substituted or non-substituted alkyl, substituted or non-substituted alkoxy and substituted or non-substituted aryloxy, or, alternatively, at least two of $Z_1$, $Z_2$, $R_1$ and $R_2$ and/or at least two of $Z_3$, $Z_4$, $R_3$ and $R_4$ from together a five- or six-membered heteroalicyclic or heteroaromatic ring, at least one of the $D_1$ and $D_2$ having the general Formula IIa or IIb), respectively, is being such that the electron donating atom is phosphorus and either the $Z_1$ and $Z_2$ or the $Z_3$ and $Z_4$ substituents of the phosphorus are each independently a substituted or non-substituted aryl, or, alternatively, at least one of the $D_1$ and $D_2$ having the general Formula IIa or IIb, respectively, is being such that the electron donating atom is phosphorus and at least one of the $Z_1$ and $Z_2$ or the $Z_3$ and $Z_4$ substituents of the phosphorus is a substituted or non-substituted alkyl or a substituted or non-substituted cycloalkyl.

According to an aspect of some embodiments of the present invention there is provided a combinatorial library of organometallic complexes, the library comprising a plurality of organometallic complexes having general Formula V:

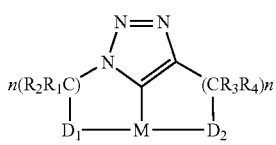

Formula V wherein:

n is an integer from 1 to 4;

$R_1$-$R_4$ are each independently selected from the group consisting of hydrogen, alkyl, cycloalkyl, aryl, heteroaryl, heteroalicyclic, alkoxy, thioalkoxy, hydroxy, thiol, amine, halogen, nitro and cyano;

M is a transition metal; and $D_1$ is an electron donating group of the general Formula IIa:

$$Z_1Z_2Xa \qquad \text{Formula IIa;}$$

and $D_2$ is an electron donating group of the general Formula IIb:

$$Z_3Z_4Xb \qquad \text{Formula IIb;}$$

whereas:

Xa and Xb are each independently an electron donating atom; and $Z_1$, $Z_2$, $Z_3$ and $Z_4$ are each independently absent or a substituent selected from the group consisting of substituted or non-substituted aryl, substituted or non-substituted alkyl, substituted or non-substituted alkoxy and substituted or non-substituted aryloxy, or, alternatively, at least two of $Z_1$, $Z_2$, $R_1$ and $R_2$ and/or at least two of $Z_3$, $Z_4$, $R_3$ and $R_4$ from together a five- or six-membered heteroalicyclic or heteroaromatic ring, at least one of the $D_1$ and $D_2$ having the general Formula IIa or IIb, respectively, is being such that the electron donating atom is phosphorus and either the $Z_1$ and $Z_2$ or the $Z_3$ and $Z_4$ substituents of the phosphorus are each independently a substituted or non-substituted aryl, or, alternatively, at least one of the $D_1$ and $D_2$ having the general Formula IIa or IIb, respectively, is being such that the electron donating atom is phosphorus and at least one of the $Z_1$ and $Z_2$ or the $Z_3$ and $Z_4$ substituents of the phosphorus is a substituted or non-substituted alkyl or a substituted or non-substituted cycloalkyl, the complexes being different from one another in at least one of the metal, the electron donating groups D1 and D2 and at least one of n and $R_1$-$R_5$.

According to an aspect of some embodiments of the present invention there is provided a method of identifying a candidate organometallic complex for catalyzing a chemical reaction, the method comprising:

screening a combinatorial library described hereinabove, by determining a catalytic activity of at least a portion of the plurality of organometallic complexes in the chemical reaction, thereby identifying the candidate organometallic complex.

According to an aspect of some embodiments of the present invention there is provided a chemical reaction performed in the presence of an organometallic complex described hereinabove.

According to an aspect of some embodiments of the present invention there is provided a compound having the general Formula VI:

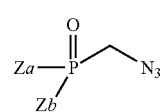

Formula VI wherein Za and Zb are each independently selected from the group consisting of a substituted or non-substituted aryl, a substituted or non-substituted alkyl and a substituted or non-substituted cycloalkyl.

According to an aspect of some embodiments of the present invention there is provided a process of preparing the compound having Formula VI, the process comprising:

converting a diaryl halophosphine containing Za and Zb to a hydroxymethyldiarylphosphine oxide; and reacting the hydroxymethyldiarylphosphine oxide with an azide, thereby obtaining the compound.

According to an aspect of some embodiments of the present invention there is provided a process of preparing the compound having Formula VI, the process comprising:

converting a halophosphine substituted by Za and Zb to a phosphonylacetic acid substituted by Za and Zb;

converting the phosphonylacetic acid substituted by Za and Zb to a bromomethylphosphine oxide substituted by Za and Zb; and reacting the bromomethylphosphine oxide substituted by Za and Zb with an azide, thereby obtaining the compound.

According to an aspect of some embodiments of the present invention there is provided a process of preparing the compound having Formula VI, the process comprising:

converting a halophosphine substituted by Za and Zb to a phosphonylacetate substituted by Za and Zb;

converting the phosphonylacetate substituted by Za and Zb to a alpha-bromo phosphonyl acetate substituted by Za and Zb;

converting the alpha-bromo phosphonyl acetate substituted by Za and Zb to a bromomethylphosphine oxide substituted by Za and Zb; and reacting the bromomethylphosphine oxide substituted by Za and Zb with an azide, thereby obtaining the compound.

According to an aspect of some embodiments of the present invention there is provided a compound having the general Formula VII:

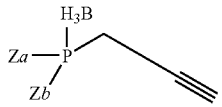

Formula VII wherein Za and Zb are each independently selected from the group consisting of a substituted or non-substituted aryl, a substituted or non-substituted alkyl and a substituted or non-substituted cycloalkyl.

According to an aspect of some embodiments of the present invention there is provided a process of preparing the compound having Formula VII, the process comprising:

converting a diarylphosphine substituted by the Za and Zb to a phosphine borane complex substituted by Za and Zb; and reacting the borane complex with a reactive propargyl, thereby obtaining the compound.

According to an aspect of some embodiments of the present invention there is provided a process of preparing the compound having Formula VII, the process comprising:

reacting a propargyl magnesium halide with a halophosphine-borane complex substituted by Za and Zb, thereby obtaining the compound.

According to an aspect of some embodiments of the present invention there is provided a compound having a general Formula VIII:

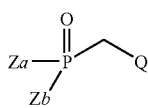

Formula VIII wherein:

Q is selected from the group consisting of azide, halide, carboxy, and hydroxy; and at least one of Za and Zb is a substituted or non-substituted alkyl or a substituted or non-substituted cycloalkyl.

According to some embodiments of the invention, at least one of $D_1$ and $D_2$ having the general Formula IIa or IIb, respectively, is being such that the electron donating atom is phosphorus and the $Z_1$ and $Z_2$ or the $Z_3$ and $Z_4$ substituents of the phosphorus are each independently a substituted or non-substituted aryl.

According to some embodiments of the invention, at least one of $D_1$ and $D_2$ having the general Formula IIa or IIb, respectively, is being such that the electron donating atom is phosphorus and the $Z_1$ and $Z_2$ and the $Z_3$ and $Z_4$ substituents of the phosphorus are each independently a substituted or non-substituted aryl.

According to some embodiments of the invention, at least one of $D_1$ and $D_2$ having the general Formula IIa or IIb, respectively, is being such that the electron donating atom is phosphorus and at least one of the $Z_1$ and $Z_2$ or the $Z_3$ and $Z_4$ substituents of the phosphorus is a substituted or non-substituted alkyl or a substituted or non-substituted cycloalkyl.

According to some embodiments of the invention, the $Z_1$ and $Z_2$ or the $Z_3$ and $Z_4$ substituents of the phosphorus are each independently selected from the group consisting of a substituted or non-substituted alkyl and a substituted or non-substituted cycloalkyl.

According to some embodiments of the invention, the $Z_1$ and $Z_2$ and the $Z_3$ and $Z_4$ substituents of the phosphorus are each independently selected from the group consisting of a substituted or non-substituted alkyl and a substituted or non-substituted cycloalkyl.

According to some embodiments of the invention, $R_1$-$R_5$ are each hydrogen.

According to some embodiments of the invention, n equals 1.

According to some embodiments of the invention, each of the electron donating atoms Xa and Xb is independently selected from the group consisting of phosphorus, sulfur, nitrogen and carbon, the carbon being a carbene that forms a part of a N-heteroalicyclic or a N-heteroaryl.

According to some embodiments of the invention, Xa and Xb are each phosphorus.

According to some embodiments of the invention, Xa is phosphorus and Xb is nitrogen.

According to some embodiments of the invention, Xa is sulfur and Xb is phosphorus.

According to some embodiments of the invention, $Z_3$ and $Z_4$ are each aryl.

According to some embodiments of the invention, $Z_3$ and $Z_4$ are each independently selected from the group consisting of alkyl and cycloalkyl.

According to some embodiments of the invention, $Z_1$ is aryl and $Z_2$ is absent.

According to some embodiments of the invention, $Z_1$ and $Z_2$ are each aryl.

According to some embodiments of the invention, $Z_1$ and $Z_2$ are each independently selected from the group consisting of alkyl and cycloalkyl.

According to some embodiments of the invention, each of $Z_1$, $Z_2$, $Z_3$ and $Z_4$ is independently a substituted or non-substituted aryl.

According to some embodiments of the invention, each of $Z_1$, $Z_2$, $Z_3$ and $Z_4$ is independently selected from the group consisting of a substituted or non-substituted alkyl and a substituted or non-substituted cycloalkyl.

According to some embodiments of the invention, the compound is selected from the group consisting of:

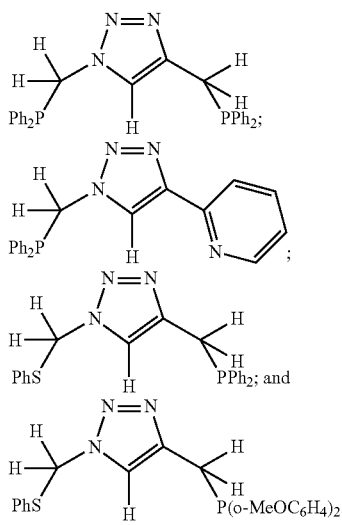

According to some embodiments of the invention, the compound is selected from the group consisting of:

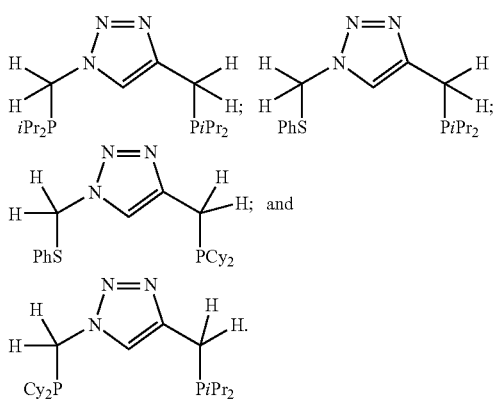

According to some embodiments of the invention, the cycloaddition reaction is performed in the presence of a copper (I) catalyst.

According to some embodiments of the invention, the cycloaddition reaction is performed at room temperature.

According to some embodiments of the invention, the cycloaddition reaction is the "click" reaction.

According to some embodiments of the invention, at least one of Wa and Wb is a protecting group, the process further comprising, subsequent to the reacting via a 1,3-dipolar cycloaddition reaction:

removing the protecting group.

According to some embodiments of the invention, the process described hereinabove is for forming a combinatorial library of tridentate ligands having the above general Formula I.

According to some embodiments of the invention, M is selected from the group consisting of palladium, platinum, rhodium, zirconium, ruthenium, iridium, nickel, iron, and osmium, each optionally further comprising an additional ligand.

According to some embodiments of the invention, contacting a salt or a complex of the metal with a compound having general Formula I is performed under basic conditions.

According to some embodiments of the invention, Za and Zb are each independently a substituted or non-substituted aryl.

According to some embodiments of the invention, at least one of Za and Zb is a substituted or non-substituted alkyl or a substituted or non-substituted cycloalkyl.

According to some embodiments of the invention, each of Za and Zb is independently selected from the group consisting of a substituted or non-substituted alkyl and a substituted or non-substituted cycloalkyl.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

The present invention, in some embodiments thereof, relates to novel compounds, methods of preparing same, metal complexes formed therewith and uses thereof and, more particularly, but not exclusively, to novel dialkylphosphine-containing compounds and diarylphosphine-containing compounds that can be utilized for forming a library of tridentate ligands, such as, for example, pincer-type ligands, to methods of synthesizing these compounds and ligands, to uses thereof in, for example, the preparation of organometallic complexes and to the various uses of such organometallic complexes.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

As discussed hereinabove, tridentate pincer type ligands have found spectacular employment in many applications, particularly in the field of organometallics. Thus, in recent years, pincer type organometallic complexes have been extensively studied. The realization that pincer ligands offer both a unique, highly protective environment for the coordinated metal center and opportunities to fine tune the steric and electronic metal properties has generated extensive research into the use of these complexes as catalysts. As a result, many important and challenging catalytic processes have been developed based on such systems.

It is generally accepted that the reactivity, selectivity and catalytic performance of pincer-based systems relies on the characteristics of the electron donating groups in the carefully selected ligand. These characteristics depend on the type of the coordinating atom, and further on the nature of its substituents.

As mentioned hereinabove, pincer ligands are traditionally prepared by attaching electron donating atoms or groups to a ligand backbone. Such a synthetic pathway often involves a laborious process and commonly results in low yields, particularly due to the non-regioselectivity of attachment and the need to separate the desired product from its regioisomers. This is even more complicated in cases where the desired ligand is hetero symmetric (when $D_1$ and $D_2$ are different from one another).

Figure 1:
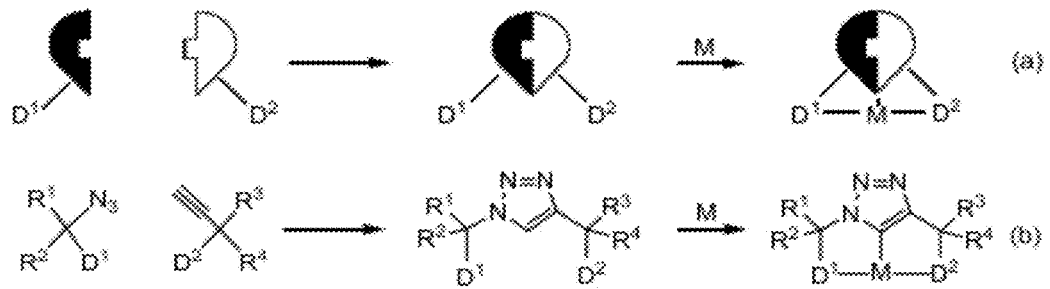
FIG. 1 presents schematic illustrations depicting the conceptual approach (a) and a generalized synthetic strategy (b) for utilizing "click" chemistry for obtaining ligands and organometallic complexes according to some embodiments of the invention.

While conceiving the present invention, it was envisioned that an efficient and facile preparation of a novel family of tridentate ligands that comprise two electron donating groups could be achieved by the design and preparation of tridentate ligands which may be readily synthesized via "click" chemistry, by selective and easy complementary binding of two precursors, each comprising an electron donating group, by covalent assembly, to afford a pincer type system in which the moiety formed by the reaction of the two precursors has an ability to interact with a metal ion. This concept is schematically illustrated in FIG. 1A.

It was further envisioned that the abovementioned approach could greatly facilitate the creation of novel and diverse libraries of such tridentate ligands through combinatorial chemistry, utilizing selected precursors.

While further conceiving the present invention, it was envisioned that the Huisgen 1,3-dipolar cycloaddition of azides and alkynes to yield triazoles could be utilized for ligand assembly. It was further envisioned that the Sharpless-modified Huisgen [2+3] cycloaddition of alkynes and azides, which can be carried out under ambient conditions and with exclusive regioselectivity for the 1,4-disubstituted triazole product when mediated by catalytic amounts of Cu(I) salts, coined and referred to herein as the "click" reaction, can be efficiently utilized for that purpose.

It was envisioned that such a methodology would allow assembling a variety of azides and alkynes, decorated with various electron donating moieties, to give a triazole-based pincer frame with two donor arms at 1,4-positions of the triazole.

While reducing the present invention to practice, a plurality of compounds was designed according to the underlying principles outlined above, based on diarylphosphine-containing precursors, and were readily synthesized. As is demonstrated in the Examples section that follows, a "click" reaction between azide-containing precursors and alkyne-containing precursors was highly efficacious for preparing triazole compounds, regioselectively substituted with two electron donating groups. The resulting triazole-based ligands possess two coordinating "arms" in the 1,4-positions, and a relatively acidic C—H bond in between them, which is suitable for directed metal insertion (see, FIGS. 1B and 2).

Importantly, in contrast to traditional synthetic methodologies, hetero-tridentate ligands are selectively obtained using this methodology, as only a specific covalent assembly is possible under "click" reaction conditions.

As further demonstrated therein, such triazole compounds are effective as tridentate pincer ligands, and hence useful in the preparation of organometallic complexes. The general reaction of azide- and alkyne-containing precursors to form a triazole, and preparation of an organometallic complex therefrom, is schematically illustrated in FIG. 1B.

Figure 2:
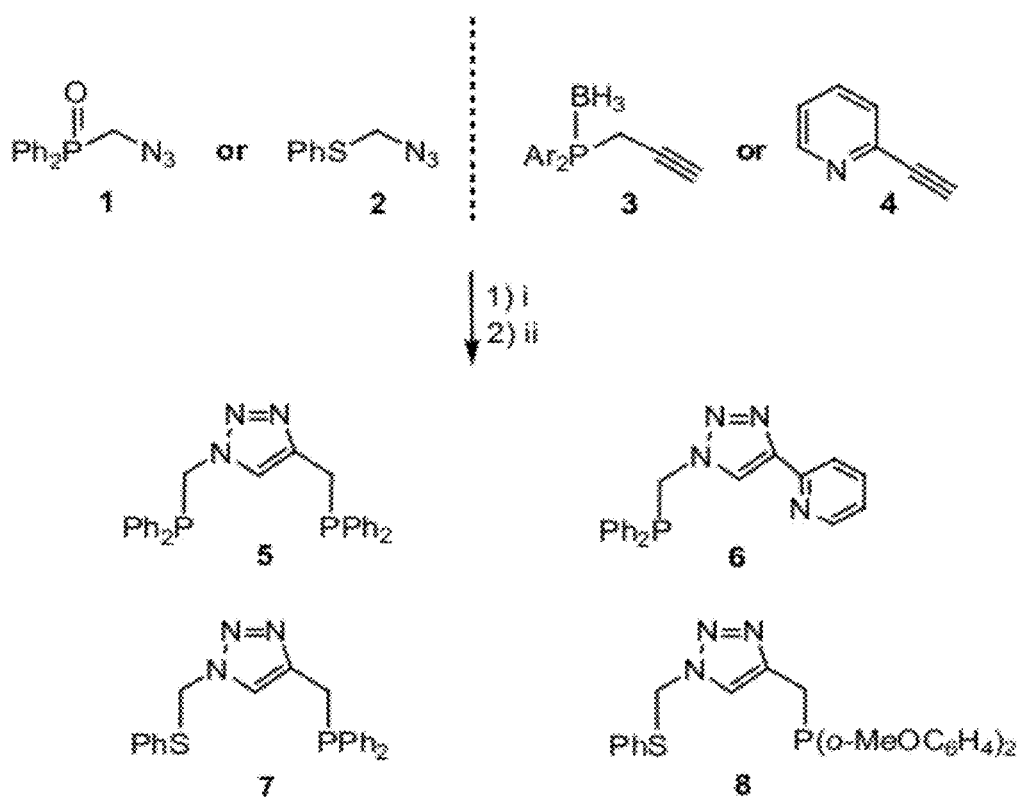
FIG. 2 presents a schematic illustration depicting the combinatorial syntheses of exemplary diarylphosphine-containing compounds according to some embodiments of the invention.
Figure 3:
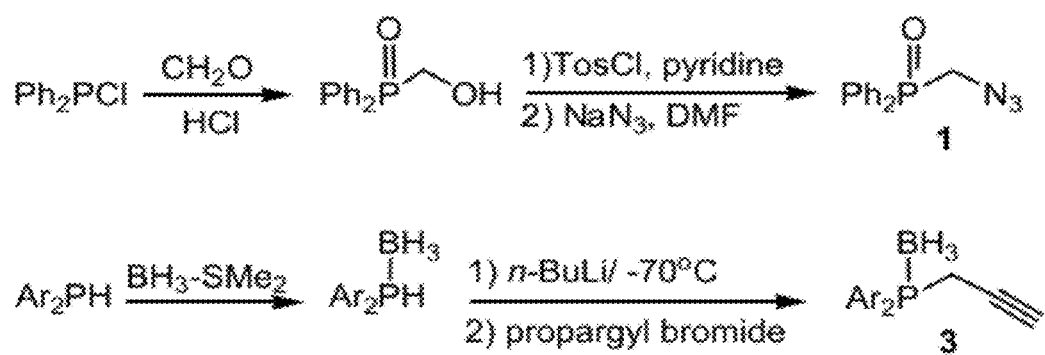
FIG. 3 presents a schematic illustration depicting the syntheses of exemplary building blocks utilized for forming the diarylphosphine-containing compounds according to some embodiments of the invention.

As demonstrated in the Examples section that follows, because of the ease of synthesis, a variety of tridentate ligands may be readily prepared by combinatorial synthesis using various precursors. Combinatorial synthesis of exemplary compounds bearing diarylphosphine moieties is depicted in FIG. 2. Synthesis of exemplary diarylphosphine-containing precursors is depicted in FIG. 3.

While further reducing the present invention to practice, the present inventors have tested the formation of triazole-based tridentate ligands containing alkylphosphine electron donating groups, and have surprisingly uncovered that the required precursors for such a methodology, namely, alkylphosphines bearing an azide or alkyne group, cannot be readily prepared using methodologies which are useful for preparing diarylphosphines bearing an azide or alkyne group.

In view of the potent activity of tridentate ligands that contain alkylphosphine electron donating groups described hereinabove, and other applications of alkylphosphine compounds, particularly those containing bulky alkyls, the present inventors have searched for a novel methodology for preparing such alkylphosphine compounds.

Figure 7A:
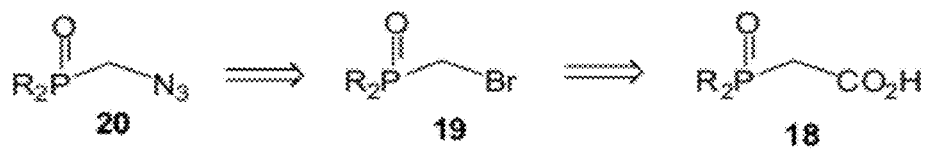
FIGS. 7A-B present a schematic illustration depicting a retrosynthesis (FIG. 7A) and an exemplary synthesis (FIG. 7B) of a dialkyl-containing building block according to some embodiments of the present invention.
Figure 7B:
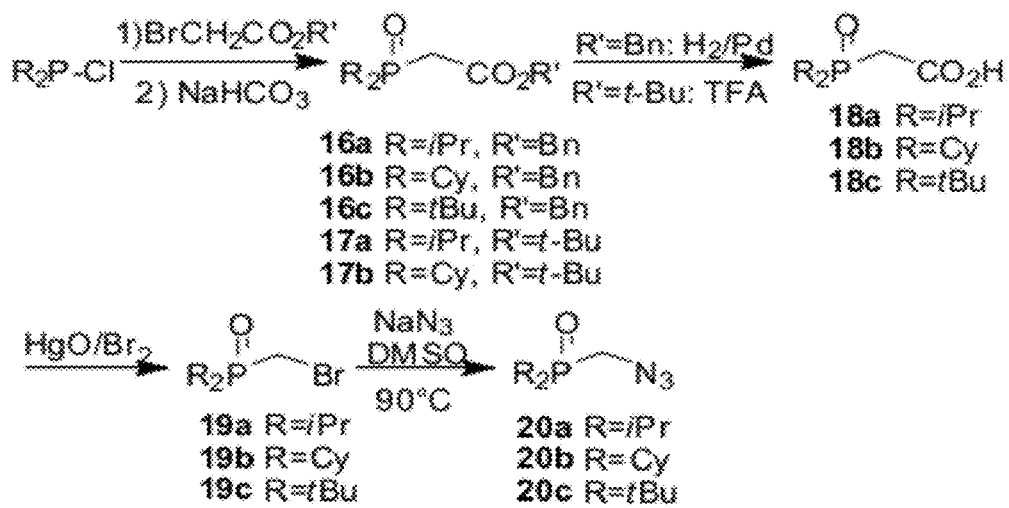
Figure 8:
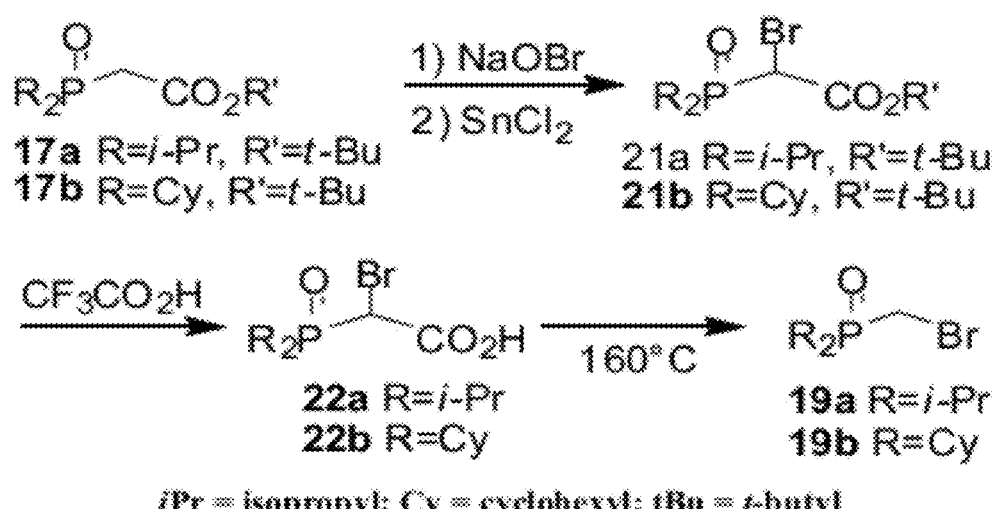
FIG. 8 presents a schematic illustration depicting an alternative synthesis of an intermediate in an exemplary synthesis of a dialkyl-containing building block according to some embodiments of the present invention.

As exemplified in the Examples section, the present inventors have developed novel methodologies for preparing both alkylphosphines bearing an azide group and alkylphosphines bearing an alkyne group. Synthesis of exemplary dialkylphosphine-containing precursors is depicted in FIGS. 7A, 7B and 8.

Figure 9:
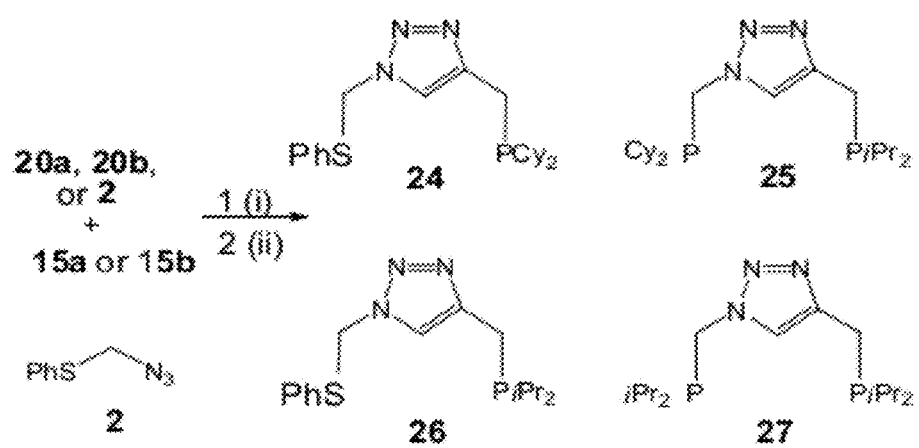
FIG. 9 presents a schematic illustration depicting the combinatorial syntheses of exemplary dialkylphosphine-containing compounds according to some embodiments of the invention.

The present inventors have further demonstrated that such compounds can readily participate in "click" reactions, so as to form alkylphosphine-containing tridentate ligands such as pincer ligands. Combinatorial synthesis of exemplary compounds bearing dialkylphosphine moieties is depicted in FIG. 9.

Thus, a conceptually new approach to the synthesis of tridentate ligands has been developed and demonstrated for both precursor molecules bearing diarylphosphine moieties and precursor molecules bearing dialkylphosphine moieties.

The methodologies taught herein thus allow for efficient and facile preparation of an entirely novel family of tridentate ligands, and further allows the creation of tridentate ligand (e.g., pincer ligand) libraries.

This family of novel tridentate ligands is also termed herein "pincer click ligands" or "PCLs".

Figure 4:
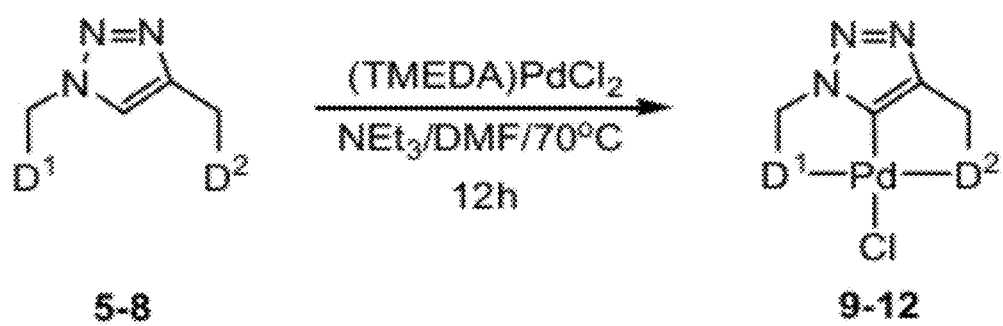
FIG. 4 presents a schematic illustration depicting the formation of exemplary palladium complexes according to embodiments of the invention.
Figure 5A:
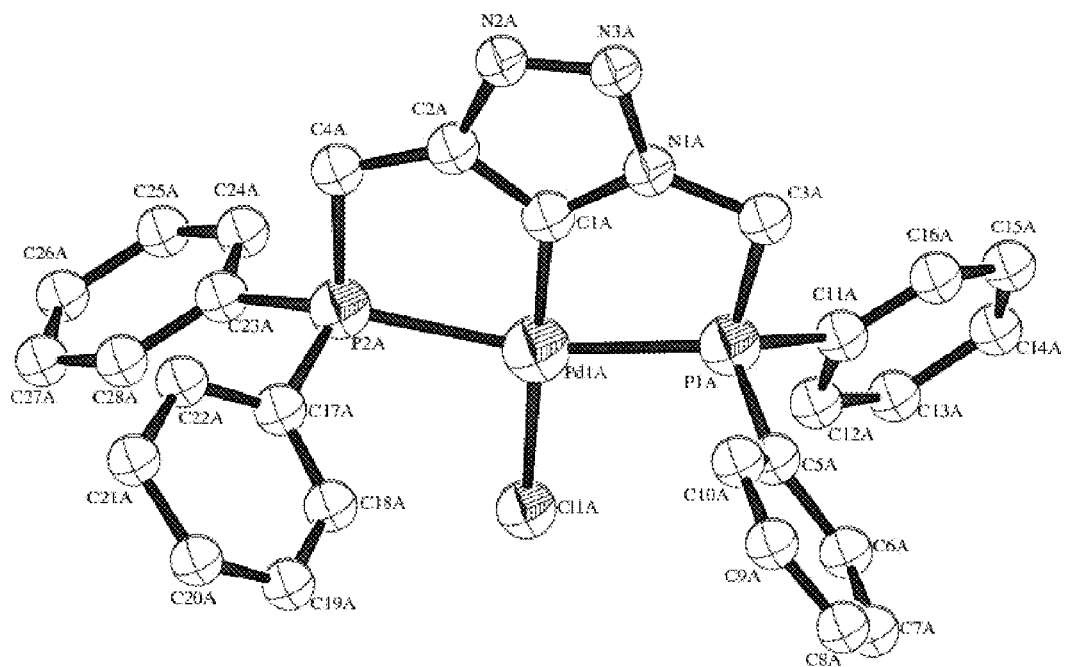
FIGS. 5A and 5B present a perspective view of a molecule of Compound 9 (FIG. 5A) and Compound 13 (FIG. 5B) as determined by X-ray crystallography; hydrogen atoms are omitted for clarity; selected bond lengths [Å] and angles of Compound 9[°]: Pd1A-C1A 1.920(17), Pd1A-P1A 2.310(5), Pd1A-P2A 2.343(6), Pd1A-C11A 2.354(4), P1A-Pd1A-P2A 157.02(18), C1A-Pd1A-C11A 177.8(5); selected bond lengths [Å] and angles of Compound 13[°]: Pt(1)-C(25) 1.908(30), Pt(1)-C1(1) 2.401(15), Pt(1)-P(2) 2.348(13), Pt(1)-P(1) 2.261(11), P(1)-Pt(1)-P(2) 159.7(3), C(25)-Pt(1)-C1(1) 177.3(9), C(25)-Pt(1)-P(1) 82.2(9), C(25)-Pt(1)-P(2) 79.0(9), P(2)-Pt(1)-C1) 99.3(3), P(1)-Pt(1)-C1(1) 99.7(3)
Figure 5B:
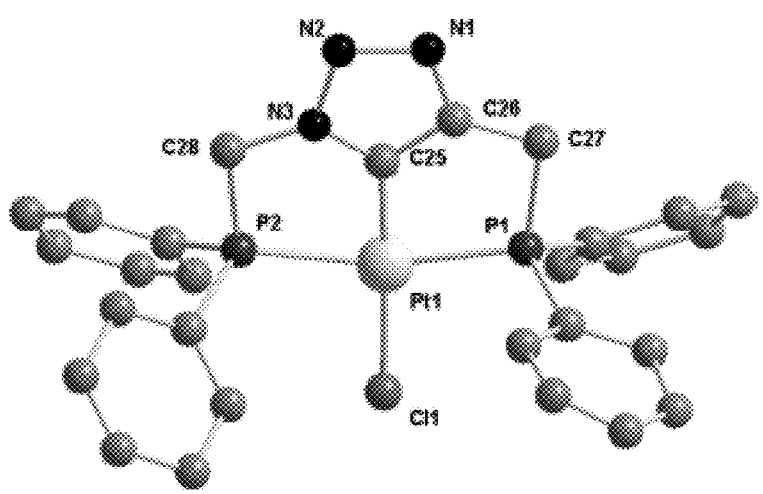

The tridentate ligands may be used to form organometallic complexes, as exemplified in FIGS. 4 and 5A-5B.

As is further demonstrated in the Examples section that follows, well-defined transition metal complexes based on these new ligands were prepared and structurally characterized, demonstrating a tridentate mode of coordination for the newly developed compounds. These complexes were further tested and found as highly efficient catalysts.

The novel methodology described herein was found to be highly advantageous for combinatorial synthesis of non-trivial ligands from relatively simple building blocks. It allows for efficient preparation and screening of a broad range of organometallic catalysts for a variety of synthetic applications. Further, the use of "click" conditions ensure operationally simple and reliable reaction protocols, broad functional group tolerance, high yields and easy purification of the products. It allows a selective straightforward synthesis of tailor-made homo- and hetero-tridentate ligands exclusively, and the electron donating groups can be easily varied. Moreover, the triazole unit in the backbone of the ligand offers an interesting alternative to the traditional phenyl-based frame. It may be further functionalized, and additional metal ions could be coordinated to the nitrogen atom after the creation of the pincer complex.

Hence, according to an aspect of some embodiments of the invention there are provided novel diarylphosphine-containing compounds, each comprising a triazole core unit, which is substituted at positions 1 and 4 thereof by moieties that contain electron-donating groups. As discussed hereinabove, these compounds can serve as tridentate ligands, e.g., pincer ligands, being either homo-tridentate ligands (having identical electron donating groups within the 1,4-substituents) or hetero-tridentate ligands (having different electron donating groups within the 1,4-substituents).

The diarylphosphine-containing compounds may be collectively represented by the general Formula I:

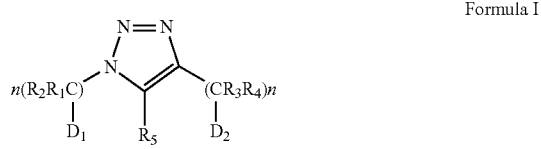

Formula I wherein:
n is an integer from 1 to 4;
$R_1$-$R_4$ are each independently selected from the group consisting of hydrogen, alkyl, cycloalkyl, aryl, heteroaryl, heteroalicyclic, alkoxy, thioalkoxy, hydroxy, thiol, amine, halogen, nitro and cyano;
$R_5$ is a leaving group that is capable of being dissociated so as to form a carbanion;

$D_1$ is an electron donating group of the general Formula IIa:

$$Z_1Z_2Xa \qquad \text{Formula IIa}$$

and
$D_2$ is an electron donating group of the general Formula IIb:

$$Z_3Z_4Xb \qquad \text{Formula IIb;}$$

whereas:
Xa and Xb are each independently an electron donating atom; and
$Z_1$, $Z_2$, $Z_3$ and $Z_4$ are each independently absent or a substituent selected from the group consisting of substituted or non-substituted aryl, substituted or non-substituted alkyl, substituted or non-substituted alkoxy and substituted or non-substituted aryloxy, or, alternatively, at least two of $Z_1$, $Z_2$, $R_1$ and $R_2$ (e.g., $Z_1$ and $Z_2$, or $Z_1$ and $R_1$) and/or at least two of $Z_3$, $Z_4$, $R_3$ and $R_4$ (e.g., $Z_3$ and $Z_4$, or $Z_3$ and $R_3$) form together a five- or six-membered heteroalicyclic or heteroaromatic ring. At least one of the electron donating groups $D_1$ and $D_2$, having general Formula IIa or IIb respectively, is such that the electron donating atom is phosphorus and the $Z_1$ and $Z_2$ substituents or the $Z_3$ and $Z_4$ substituents of the phosphorus are each independently a substituted or non-substituted aryl.

Accordingly, the compounds described herein comprise at least one electron donating group ($D_1$ and/or $D_2$ in the general Formula I hereinabove), which comprises a diarylphosphine group.

As used herein, the term "diarylphosphine" describes a R'R"P-group, wherein R' and R" are each independently an aryl, as defined herein. Thus the aryl groups in a diarylphosphine as defined herein can be the same or different.

As widely described in the art, diarylphosphines serve as highly beneficial electron donating groups in pincer type tridentate ligands.

As used herein, the phrase "electron donating group" describes a chemical group that comprises at least one electron donating atom, as this phrase is defined herein. This phrase is also referred to herein interchangeably as "donor", "donor group" and "coordinating group".

As used herein, the phrase "electron donating atom" describes any atom in a chemical group which is capable of donating one or more electrons to an electron acceptor (e.g., a metal ion), so as to coordinatively interact with the acceptor. Typically, the electron donating atom is characterized by the presence of a free electron pair. Various heteroatoms (e.g., phosphorus, sulfur, nitrogen) are known in the art to be capable of acting as electron donating atoms. In addition, a carbon atom in an N-heterocyclic carbene (e.g., an N-heterocyclic carbene which is a five- or six-membered heteroalicyclic or heteroaromatic ring described herein) may be a suitable electron donating atom.

As used herein, the term "carbene" describes any compound or group that contains a carbon atom characterized as having only two valence bonds, as well as a free electron pair. Such a carbon atom is also described herein as a "carbene carbon" or an "electron donating atom".

As used herein, the phrase "N-heterocyclic carbene" describes a carbene in which the carbene carbon is covalently bound to at least one nitrogen atom that forms a part of a heterocyclic group. Typically, the carbene carbon is covalently bound to two heteroatoms (e.g., two nitrogen atoms), which affords a relatively stable carbene. Such carbenes include, without limitation, imidazol-2-ylidenes, 1,2,4-triazol-5-ylidenes and thiazol-2-ylidenes.

As used herein, the term "heterocyclic" encompasses heteroalicyclic and heteroaryl, as these terms are defined herein.

The electron donating capability of an electron donating atom can be manipulated by the nature of its substituents or of substituents of adjacent atoms. Substituents that exhibit an electron inductive effect therefore enhance the electron donating functionality of the electron donating group.

The $D_1$ and $D_2$ groups in Formula I hereinabove can be the same or different. Thus, the resulting tridentate ligand can be a homo-tridentate ligand or a hetero-tridentate ligand. The homo-tridentate ligands, according to embodiments of the invention, include two identical electron donating groups $D_1$ and $D_2$ (e.g., identical diarylphosphine groups described herein). Hetero-tridentate ligands include compounds having different diarylphosphine groups as one of $D_1$ and $D_2$, and/or compounds having an electron donating group which is not a diarylphosphine group. An electron donating group other than diarylphosphine can be a phosphine substituted by one aryl group, a phosphine substituted by one or two groups other than aryl, or can comprise an electron donating atom other than phosphorus.

In some embodiments, $D_1$ and $D_2$ are such that the electron donating atom in each of $D_1$ and $D_2$ is phosphorus. Optionally, the $Z_1$ and $Z_2$ substituents of the $D_1$ phosphorus and the $Z_3$ and $Z_4$ substituents of the $D_2$ phosphorus are each independently a substituted or non-substituted aryl, such that the compound comprises a pair of diarylphosphine groups. Alternatively, only one of the phosphorous atoms in $D_1$ and $D_2$ bears two aryl substituents (either $Z_1$ and $Z_2$ or $Z_3$ and $Z_4$).

Exemplary electron donating groups other than diarylphosphines include, but are not limited to, amine, N— and S-containing heteroalicyclic, N— and S-containing heteroaryls, thioalkoxy, thioaryloxy and N-heterocyclic carbenes, as defined herein.

Hetero-tridentate ligands according to embodiments of the invention can include also compounds having general Formula I above, in which $D_1$ and $D_2$ are the same or different, while the moieties linking these groups to the triazole core are different from one another.

These moieties are represented as $(CR_1R_2)n$ and $(CR_3R_4)n$ in general Formula I hereinabove.

It is to be appreciated that the integer n for the $(CR_1R_2)n$ unit and the integer n for the $(CR_3R_4)n$ unit may be the same or different.

It is to be further appreciated that when n is greater than 1, each carbon atom of the $(CR_1R_2)n$ and/or $(CR_3R_4)n$ units is attached to a $R_1$ and $R_2$ or $R_3$ and $R_4$ substituent, respectively, whereby each of the $(CR_1R_2)n$ and $(CR_3R_4)n$ unit can be the same of be different from one another.

In some embodiments, $(CR_1R_2)n$ and $(CR_3R_4)n$ are the same in length, such that n in both units is the same.

As delineated hereinabove, each of $R_1$, $R_2$, $R_3$ and $R_4$ can be independently hydrogen, alkyl, cycloalkyl, aryl, heteroaryl, heteroalicyclic, alkoxy, thioalkoxy, hydroxy, thiol, amine, halogen, nitro or cyano, as these terms are defined herein.

In some embodiments, each of $R_1$, $R_2$, $R_3$ and $R_4$ is hydrogen.

In some embodiments, one or more of $R_1$, $R_2$, $R_3$ and $R_4$ is other than hydrogen. In some embodiments, the $R_1$, $R_2$, $R_3$ and/or $R_4$ substituent is an electron donating group, as described herein, such that it contributes to the electron donating functionality of the $D_1$ and/or $D_2$ electron donating groups.

In some embodiments, n equals 1. Without being bound to any particular theory, it is assumed that compounds in which n equals 1 exhibit good coordinative performance when used as tridentate ligands for complexing transition metals. Such compounds exhibit high stability that is at least partially attributed to the 5-membered heterocyclic ring(s) formed, which is more pronounced with electron donating atoms such as phosphorus (as compared, for example, to electron donating atoms such as sulfur and nitrogen). However, lengthier units can further exhibit such a coordinative performance, or can beneficially serve for other applications, and hence, n in each of the $(CR_1R_2)n$ and $(CR_3R_4)n$ units can further be independently 2, 3, 4 and even higher.

According to exemplary embodiments of the present invention, n equals 1, such that $(CR_1R_2)n$ and $(CR_3R_4)n$ are each a substituted or non-substituted methylene group (e.g., $CH_2$).

In some embodiments, n equals 1 and $(CR_1R_2)n$ and $(CR_3R_4)n$ are each a —$CH_2$-group.

$R_5$ is a leaving group. The phrase "leaving group" is used in the context of embodiments of the invention to describe a chemical group or atom that is capable of being dissociated from the compound, to thereby form a carbanion.

In some embodiments, $R_5$ is hydrogen. Being at position 5 of the triazole core, this hydrogen is acidic and readily dissociates as a proton, to thereby form a carbanion.

Turning back now to the electron donating groups, it is to be understood that for each electron donating group, $Z_1$ or $Z_2$ can form a bond together with one of $R_1$ and $R_2$, or, alternatively or in addition, $Z_3$ or $Z_4$ can form a bond together with one of $R_3$ and $R_4$, such that the Xa and/or Xb electron donating atoms are linked to the adjacent carbon via a double bond.

Alternatively, or in addition, $Z_1$ or $Z_2$ can form, together with one of $R_1$ and $R_2$, or, alternatively or in addition, $Z_3$ or $Z_4$ can form together with one of $R_3$ and $R_4$, a heteroalicyclic or heteroaromatic (heteroaryl) ring.

In an example, Xa is N, $Z_3$ and $R_3$ form together a bond, such that the nitrogen is linked to the adjacent carbon via a double bond, and $Z_4$ and $R_4$ from together a =CH—CH=CH—CH= group, thus forming, e.g., a pyridin-2-yl group.

Similarly, the electron donating group formed from at least two of $R_1$, $R_2$, $Z_1$ and $Z_2$, and/or between $R_3$, $R_4$, $Z_3$ and $Z_4$, can be piperidin-2y-1, piperazin-2-yl, pyrrolidin-2-yl, tetrahydrothiophen-2-yl, tetrahydropyrane-2-yl and thiophene-2-yl.

In some embodiments, $Z_1$ and $Z_2$ and/or $Z_3$ and $Z_4$ can form together a 5- or 6-membered heteroalicyclic or heteroaromatic ring.

According to an exemplary embodiment, Xa and Xb are each phosphorus. In some embodiments, each of $Z_1$, $Z_2$, $Z_3$ and $Z_4$ is independently a substituted or non-substituted aryl.

According to another exemplary embodiment, Xa is phosphorus and Xb is nitrogen. Optionally, the phosphorus atom is bound to two aryl groups, such that $Z_1$ and $Z_2$ are each aryl. In some embodiments, the nitrogen atom forms a part of a pyridinyl group (e.g., pyridin-2-yl).

According to yet another exemplary embodiment, Xa is sulfur and Xb is phosphorus. In some embodiments, the sulfur atom is bound to an aryl, such that $Z_1$ is aryl and $Z_2$ is absent. In some embodiments, the phosphorus atom is bound to two aryl groups, such that $Z_3$ and $Z_4$ are each aryl.

Exemplary compounds comprising at least one diarylphosphine moiety include:

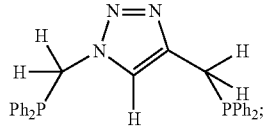

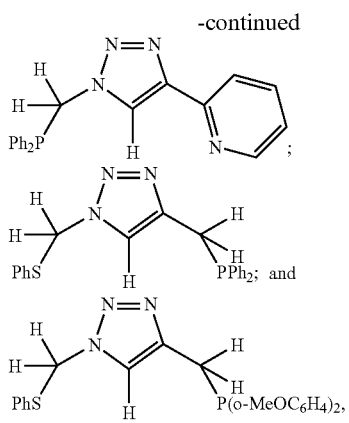

wherein "Ph" denotes phenyl, and "o-MeOC$_6$H$_4$" denotes ortho-methoxyphenyl.

As widely described in the art, diarylphosphine-based ligands are highly suitable for forming organometallic complexes useful as catalysts for various chemical reactions (e.g., Heck reaction).

As exemplified herein in the Examples section, the present inventors have further prepared compounds comprising alkylphosphine groups. As widely described in the art, alkylphosphines (e.g., dialkylphosphines) serve as highly beneficial electron donating groups in pincer type tridentate ligands and complexes formed therewith. As discussed hereinabove, phosphine-containing tridentate ligands, bearing one or more bulky, electron donating groups (e.g., bulky alkyl groups) as substituents of the phosphorus atom, have recently been recognized as highly advantageous in a myriad of applications. Thus, alkylphosphine ligands are expected to be more suitable than diarylphosphine ligands for certain applications.

Hence, according to another aspect of some embodiments of the invention there are provided novel alkylphosphine-containing compounds, each comprising a triazole core unit, which is substituted at positions 1 and 4 thereof by moieties that contain electron-donating groups, as described hereinabove.

The alkylphosphine-containing compounds may be collectively represented by the general Formula I described hereinabove, wherein n, R$_1$-R$_5$, Xa, Xb, and Z$_1$-Z$_4$ are as described above, except that at least one of D$_1$ and D$_2$ is an alkylphosphine group, wherein the electron donating atom is phosphorus, and at least one of Z$_1$ and Z$_2$ or at least one of Z$_3$ and Z$_4$ is selected from the group consisting of a substituted or non-substituted alkyl and a substituted or non-substituted cycloalkyl.

As used herein, the term "alkylphosphine" describes a R'R"P-group, wherein at least one of R' and R" is alkyl or cycloalkyl, as defined herein. The terms "alkylphosphine" and "dialkylphosphine" are therefore used herein for convenience purposes to describe a phosphorous atom that is substituted by one or two non-aromatic moieties which can be either aliphatic, namely, alkyls, or alicyclic, namely, cycloalkyl, as these terms are defined herein.

Optionally, the alkylphosphine comprises one alkyl or cycloalkyl group and one group which is not alkyl or cycloalkyl (e.g., aryl). Thus, it is to be appreciated that an alkylphosphine group may comprise an aryl group, for example, wherein R' is aryl and R" is alkyl or cycloalkyl.

In some embodiments, the Z$_1$ and Z$_2$ or the Z$_3$ and Z$_4$ substituents of the phosphorus are each independently a substituted or non-substituted alkyl or a substituted or non-substituted cycloalkyl, such that the compound comprises a dialkylphosphine group.

As used herein, the term "dialkylphosphine" describes a R'R"P-group, wherein R' and R" are each independently an alkyl or cycloalkyl, as defined herein.

It is to be appreciated that a compound may comprise both a dialkylphosphine group (e.g., as D$_1$) and a diarylphosphine group (e.g., as D$_2$).

In some embodiments, D$_1$ and D$_2$ are such that the electron donating atom in each of D$_1$ and D$_2$ is phosphorus. Optionally, the Z$_1$ and Z$_2$ substituents of the D$_1$ phosphorus and the Z$_3$ and Z$_4$ substituents of the D$_2$ phosphorus are each independently a substituted or non-substituted alkyl or a substituted or non-substituted cycloalkyl, such that the compound comprises a pair of dialkylphosphine groups.

According to an exemplary embodiment, Xa and Xb are each phosphorus. In some embodiments, each of Z$_1$, Z$_2$, Z$_3$ and Z$_4$ is independently a substituted or non-substituted alkyl a substituted or non-substituted cycloalkyl.

According to another exemplary embodiment, Xa is phosphorus and Xb is nitrogen. Optionally, Z$_1$ and Z$_2$ are optionally each independently selected from the group consisting of alkyl and cycloalkyl. In some embodiments, the nitrogen atom forms a part of a pyridinyl group (e.g., pyridin-2-yl).

According to yet another exemplary embodiment, Xa is sulfur and Xb is phosphorus. In some embodiments, the sulfur atom is bound to an aryl, such that Z$_1$ is aryl and Z$_2$ is absent. Alternatively, the Z$_3$ and Z$_4$ are optionally each independently selected from the group consisting of alkyl and cycloalkyl.

In some embodiments, when Xa is phosphorus and at least one of Z$_1$ and Z$_2$ is alkyl, (CR$_1$R$_2$)n is such that n equals 1.

In some embodiments, when Xb is the phosphorus and at least one of Z$_3$ and Z$_4$ is alkyl, (CR$_3$R$_4$)n is such that n equals 1.

As discussed hereinabove, bulky alkyl substituents in alkylphosphine groups have recently been recognized and highly advantageous in a myriad of applications.

Hence, according to some embodiments, the alkyl substituting the phosphorus is a bulky alkyl such as, but not limited to, isopropyl, tent-butyl and a cycloalkyl (such as cyclohexyl). Optionally, the phosphorus is substituted by two bulky alkyl groups (e.g., is a dialkylphosphine group).

Exemplary compounds comprising at least one dialkylphosphine moiety include:

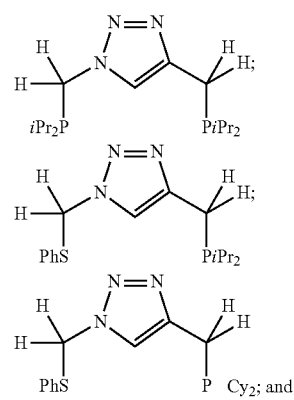

-continued

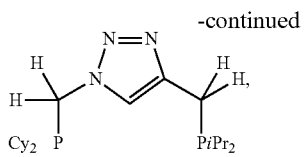

wherein "Ph" denotes phenyl, "Cy" denotes cyclohexyl, and "iPr" denotes isopropyl.

As discussed hereinabove and is exemplified hereinbelow, the compounds represented by general Formula I (e.g., diarylphosphine- and alkylphosphine-containing compounds) may be conveniently prepared from precursor molecules using a cycloaddition reaction (e.g., the "click" reaction).

Hence, according to another aspect of the present invention, there is provided a process of preparing a compound having general Formula I as described hereinabove, the process comprising reacting, via a 1,3-dipolar cycloaddition reaction, a compound having general Formula IIIa:

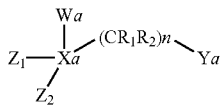

Formula IIIa with a compound having general Formula IIIb:

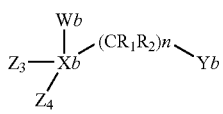

Formula IIIb wherein:

Wa and Wb are each independently a protecting group or absent;

Ya is a —$N_3$ group;

Yb is a —C≡C—$R_5$ group;

n is an integer from 1 to 4, as described herein;

$R_1$-$R_4$ are each independently selected from the group consisting of hydrogen, alkyl, cycloalkyl, aryl, heteroaryl, heteroalicyclic, alkoxy, thioalkoxy, hydroxy, thiol, amine, halogen, nitro and cyano, as described herein;

$R_5$ is a leaving group, as described herein;

Xa and Xb are each independently an electron donating atom, as described herein; and $Z_1$, $Z_2$, $Z_3$ and $Z_4$ are each independently absent or a substituent as described herein, such that at least one of the electron donating atoms is phosphorus and at least one of the $Z_1$ and $Z_2$ or $Z_3$ and $Z_4$ substituents of the phosphorus is a substituted or non-substituted aryl, a substituted or non-substituted alkyl, or a substituted or non-substituted cycloalkyl, as described herein.

As used herein, and is well-known in the art, a 1,3-dipolar cycloaddition reaction is a 2+3 cycloaddition reaction that results in a 5-membered ring and is facilitated by the presence of partial positive and negative charges at the 1 and 3 positions of a substance to which cycloaddition is made.

As delineated hereinabove, in some embodiments, this reaction is performed according to the "click" chemistry, via a reaction coined the "click" reaction. The currently known "click" reaction is performed between an azide and an alkyne, represented by Ya and Yb, respectively, in Formulae IIIa and IIIb, respectively, to thereby form a triazole.

It is noted that other functional groups can be utilized in the methodology described herein, as long as these functional groups, Ya and Yb, are compatible with each other in a 1,3-dipolar cycloaddition reaction that results in a 5-membered or 6-membered ring, and is preferably performed selectively and under mild conditions.

As further discussed hereinabove, the process described herein is advantageously performed in the presence of a copper catalyst, such as a copper (I) catalyst, which allows performing the "click" reaction at ambient temperatures and in high yield and regioselectivity. When using a copper catalyst, the compound of Formula IIIb is selected such that $R_5$ is hydrogen.

Thus, in some embodiments, the cycloaddition reaction is performed at room temperature. As is well known in the art, the ability to perform reactions at room temperature provides considerable advantages, such as convenience and ease of synthesis, cost-effectiveness, reduction of undesired reactions which compete with the cycloaddition reaction, and avoidance of heat-related damage to the precursors and/or product which may reduce yields. Performing a reaction at room temperature is particularly advantageous when one of the reactants is an azide, which is considered heat-sensitive.

As further delineated hereinabove, the starting materials (precursors) utilized in the process described herein, represented by Formulas IIIa and IIIb, can be tailor-made according to the desired properties of the final products. These starting materials are azides and alkynes, each decorated by various substituents, while at least one of the alkyne and azide utilized is being an electron donating group, as described herein.

The starting materials utilized in this process can be prepared as desired via well-known procedures. Some starting materials having Formulas IIIa and IIIb are commercially available. By selecting the Xa, $R_1$, $R_2$, n, $Z_1$ and $Z_2$ of the azide-containing starting material, and similarly, the Xb, $R_3$, $R_4$, n, $Z_3$ and $Z_4$ of the alkyne-containing starting material, the structural and chemical properties of the resulting tridentate ligand can be readily manipulated.

The Xa, $R_1$, $R_2$, n, $Z_1$ and $Z_2$ of the azide-containing starting material, and the Xb, $R_3$, $R_4$, n, $Z_3$ and $Z_4$ of the alkyne-containing starting material are selected so as not to interfere with the cycloaddition reaction and to remain stable under the conditions the cycloaddition reaction is performed. Selecting the appropriate electron-donating atoms and substituents is well within the knowledge of those skilled in the art.

The electron donating group utilized in each of the precursors (starting materials), can be protected during the reaction by means of Wa and Wb protecting groups.

In some embodiments, at least one of Wa and Wb is present as a protecting group. Exemplary protecting groups include borane (e.g., $BH_3$) and oxo (i.e., =O). Such protecting groups are particularly useful when attached to an electron donating atom (e.g., Xa or Xb) that is phosphorus, thereby forming a phosphine-borane complex or a phosphine oxide, respectively. Other protecting groups, such as, for example, thio-oxo (i.e., =S), and other complexing groups, are also contemplated.

The protecting group may be any group which is capable of preventing or limiting a reaction involving the electron donating atom under the reaction conditions of the cycloaddition reaction, and which may be readily removed following cycloaddition. Thus, for example, phosphine-borane complexes and phosphine oxides both prevent an undesirable Staudinger reaction between the azide and the phosphine. The phosphine can then be deprotected, for example, by DABCO (diazabicyclo[2.2.2]octane) in the case of the phosphine-borane complex, or by reduction (e.g., with trichlorosilane) in the case of the phosphine oxide, to thereby obtain a phosphine product with high yields (e.g., about 80%).

The process described herein has numerous important advantages. The conditions of the cycloaddition reaction (e.g., the "click" reaction) allow operationally simple and reliable reaction protocols, broad functional group tolerance, high yields, and easy purification of the product. In addition, the process allows selective and straightforward synthesis of tailor-made hetero-tridentate ligands (i.e., ligands wherein $D_1$ and $D_2$ are not identical) wherein the location of the attachment of each electron donating group to the triazole moiety is readily determined, and the identity of the electron donating groups may be easily varied.

Furthermore, as discussed hereinabove, compounds having Formulas IIIa and IIIb are typically either commercially available or may be prepared in a simple manner by synthetically short protocols, as exemplified in the Examples section that follows, which are well within the capabilities of one of ordinary skill in the art. Preparation of representative PCP (phosphorus-based electron donating groups), PCN (phosphorus-nitrogen-based electron donating groups) and PCS (phosphorus-sulfur-based electron donating groups) tridentate ligands are exemplified in the Examples section that follows.

As exemplified in the Examples section that follows, a number of azido- and alkynyl-based starting materials (precursors) were prepared and smoothly underwent copper(I)-catalyzed reciprocal [2+3] cycloaddition reactions under "click" conditions. Representative examples of the prepared ligands include PCP (Phosphorus-Phosphorus based, Compound 5), PCN (Phosphorus-Nitrogen based, Compound 6) and PCS (Phosphorus-Sulfur based, Compounds 7 and 8) binding modes (see, FIG. 2).

A typical reaction takes place in a polar solvent such as a THF/water solution, without air exclusion to furnish full conversion of the starting materials to the (optionally protected) ligands after stirring for 24 hours at room temperature.

Using the advantageous process described herein, a myriad of diverse tridentate ligands can be prepared. Application of the process described herein in a systemic combinatorial manner therefore results in a wide variety of triazole-based tridentate ligands such as, for example, pincer ligands. Thus, for example, from N(a) precursor compounds having Formula IIIa, and N(b) precursor compounds having Formula IIIb, as many as N(a)×N(b) compounds of Formula I may be prepared (with N being an integer denoting the number of the respective precursor compound).

Hence, according to some embodiments, the process described herein is utilized for forming a combinatorial library of tridentate ligands having general Formula I. The ligands of the library are distinct from one another, being different in at least one of the variables $D_1$, $D_2$ and/or at least one of the variables n and $R_1$-$R_5$.

Accordingly, according to an aspect of embodiments of the invention, there is provided a combinatorial library of tridentate ligands having general Formula I as described herein. Such a combinatorial library comprises, for example, compounds having Formula I as described herein, which differ one from another by the nature of one or more of the electron donating group, e.g., one or more of the electron donating atoms and/or one of more of the substituents of the electron donating atoms; and/or by the nature of the units linking the electron donating group to the triazole core, e.g., the length of one or more of these units, the substituents of the carbon atoms composing this units, etc., as these structural and chemical features are described herein for, for example, compounds represented by general Formula I presented herein.

In some embodiments, a combinatorial library of tridentate ligands as described herein comprises any of the compounds having general Formula I as presented herein. Exemplary combinatorial sub-libraries include, but are not limited to, the following:

=Tridentate ligands having Formula I as described herein, which differ from one another by one of the electron donating groups, and more particularly, by the nature of the substituents of one of the electron donating atoms. Ligands in such sub-library can therefore include compounds having Formula I as described herein, which differ from one another by $Z_1$, by $Z_2$ or both, by $Z_3$, by $Z_4$ or both, or by any of $Z_1$, $Z_2$, $Z_3$ and $Z_4$. In some embodiments, ligands in this sub-library all include one or more diarylphosphine moieties, and differ from one another by the nature of the diarylphosphine moiety and/or by the number of such moieties in the compound. In some embodiments, ligands in this sub-library differ from one another by the absence or presence of one or more alkyl or cycloalkyl as $Z_1$, $Z_2$, $Z_3$ and/or $Z_4$.

=Tridentate ligands having Formula I as described herein, which all have at least one alkylphosphine or dialkylphosphine moiety, and which differ from one another by the nature of Xa or Xb, and/or by at least one of the variables n and $R_1$-$R_5$.

=Tridentate ligands having Formula I as described herein, which all have at least one diarylphosphine moiety, and which differ from one another by the nature of Xa or Xb, and/or by at least one of the variables n and $R_1$-$R_5$.

=Tridentate ligands having Formula I as described herein, which have the same $D_1$ and all differ by the nature of $D_2$, and vice versa.

Such a combinatorial library can be utilized for forming a myriad of diverse organometallic complexes containing such ligands and screening these complexes for a candidate catalyst for a particular reaction, as a non-limiting example.

Thus, for example, a combinatorial library as described herein can be screened for a candidate tridentate ligand for forming a stable organometallic complex with a particular metal. Determining a stability of an organometallic complex is well within the capabilities of a person skilled in the art.

In another example, a combinatorial library as described herein can be screened for a candidate tridentate ligand for forming an efficient catalyst for a particular reaction, as is further detailed hereinbelow.

The tridentate ligands described herein can be further be utilized for applications other than forming organometallic complexes. Any such application for a pincer ligand is contemplated herein.

The compounds described herein are designed capable of forming an organometallic complex with various transition metals, due to the presence of a leaving group at the $5^{th}$ position of the triazole core. The carbon atom at the 5-position of the triazole moiety comprised by the compounds described herein becomes a carbanion relatively easily, and is located between the two electron donating groups, and is therefore particularly suitable for direct metal insertion to form, for example, a pincer metal complex.

Hence, according to another aspect of some embodiments of the present invention, there is provided an organometallic complex comprising a metal and a compound having Formula I, as described herein, wherein the compound serves as a tridentate ligand being in complex with the metal. Such organometallic complexes represent pincer type complexes, which are also referred to herein as metal pincer complexes, or simply as pincer complexes.

The organometallic complexes described herein can be collectively represented by the general Formula V:

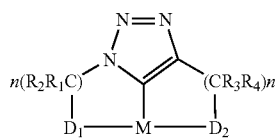

Formula V wherein:

n is an integer from 1 to 4, as described herein;

$R_1$-$R_4$ are each independently selected from the group consisting of hydrogen, alkyl, cycloalkyl, aryl, heteroaryl, heteroalicyclic, alkoxy, thioalkoxy, hydroxy, thiol, amine, halogen, nitro and cyano, as defined herein;

M is a transition metal, as described herein; and $D_1$ and $D_2$ are each an electron donating group as described herein.

It is to be understood that "M" in the general Formula V encompasses both metal atoms and metal atoms bound to one or more additional ligands (e.g., a halogen).

As used herein, and is well known in the art, the phrase "transition metal" describes an element whose atom has an incomplete d sub-shell, or which can give rise to cations with an incomplete d sub-shell (see, IUPAC definition).

Any transition metal or a complex thereof that is commonly utilized in pincer-type complexes is encompassed by the variable "M". These typically include late transition metals, such as those of Groups 7, 8, 9, 10 and 11. Non-limiting examples include palladium, platinum, rhodium, ruthenium, iridium, nickel, cobalt, iron, osmium and the like.

In some embodiments, the organometallic complex described herein comprises at least one of the $D_1$ and $D_2$ electron-donating groups in which the electron donating atom is phosphorous and its substituents, namely, $Z_1$ and $Z_2$ or $Z_3$ and $Z_4$ are each independently a substituted or non-substituted aryl, as defined herein. Such organometallic complexes therefore comprise one or more diarylphosphine electron donating group(s).

In some embodiments, the organometallic complex described herein comprises at least one of the $D_1$ and $D_2$ electron-donating groups in which the electron donating atom is phosphorous and at least one of its substituents, namely, $Z_1$ or $Z_2$, or $Z_3$ or $Z_4$, is a substituted or non-substituted alkyl, or a substituted or non-substituted cycloalkyl, as defined herein. Such organometallic complexes therefore comprise one or more alkylphosphine and/or dialkylphosphine electron donating group(s).

It is to be noted that the chemical and functional properties of organometallic complexes having one or more diarylphosphine moieties and organometallic complexes having one or more alky- or dialkyl-phosphine moieties are different.

As discussed herein, the tridentate ligands described hereinabove are particularly suitable for binding to a metal so as to form a complex. Complexing of the metal by the tridentate ligand may be easily performed, as exemplified in the Examples section hereinbelow, to yield a stable organometallic complex.

Hence, according to another aspect of some embodiments of the present invention, there is provided a process of preparing the organometallic complex described hereinabove. The process, according to this aspect of embodiments of the present invention, is effected by contacting a salt and/or a complex of the metal with the compound having Formula I, as described hereinabove. In some embodiments, the contacting is performed under basic conditions, so as to facilitate metal insertion upon removal of the acidic hydrogen at position 5 of the triazole.

Exemplary processes are described in detail in the Examples section that follows.

Optionally, the process described herein can further comprise, subsequent to reacting the tridentate ligand and the metal or its salt or complex, additional attachment(s) or modification(s) of substituents that do not participate directly in the formed complex, as long as the complex remains stable under the reaction conditions. These include, for example, modification of the triazole core, modification of any of the $R_1$-$R_4$ substituents in general Formula V, modification of any of the $Z_1$-$Z_4$ substituents (e.g., modifying a substituent in the aryl moiety), and the like. Such modifications can be performed according to synthetic pathways known in the art.

As discussed hereinabove, a combinatorial library of tridentate ligands may be prepared according to embodiments of the present invention. This library can be used to form a combinatorial library of organometallic complexes containing these ligands.

Hence, in some embodiments, there is provided a combinatorial library of organometallic complexes having the above Formula V. The organometallic complexes of the library are distinct from one another, being different in at least one of the coordinated metal (the variable "M", as defined herein), the variables $D_1$, $D_2$ and/or at least one of the variables n and $R_1$-$R_5$, as discussed herein.

In exemplary embodiments, a combinatorial library of organometallic complexes as described herein includes organometallic complexes having Formula V as presented herein, which differ from one another by the coordinated metal, yet otherwise include the same ligand.

In exemplary embodiments, a combinatorial library of organometallic complexes as described herein includes organometallic complexes having Formula V as presented herein, which differ from one another by the nature of the ligand, as described herein for a combinatorial library of tridentate ligands, and which all include the same metal.

In exemplary embodiments, a combinatorial library of organometallic complexes as described herein includes organometallic complexes having Formula V as presented herein, in which the tridentate ligand comprises one or more diarylphosphine moieties.

In exemplary embodiments, a combinatorial library of organometallic complexes as described herein includes organometallic complexes having Formula V as presented herein, in which the tridentate ligand comprises one or more dialkylphosphine moieties.

Other combinatorial libraries of organometallic complexes are also contemplated.

As discussed hereinabove, many organometallic complexes, and particularly complexes having a "pincer" structure, are useful for various purposes, for example, as catalysts for any of a wide variety of chemical (organic) reactions. However, finding an optimal catalyst may require examining the properties of a large number of organometallic complexes. Facile combinatorial access to a novel family of tridentate ligands and their corresponding metal complexes opens the door to rapid and convenient screening of these complexes in various catalytic transformations, as exemplified in the Examples section with palladium complexes with respect to catalysis of the Heck reaction.

Hence, according to another aspect of some embodiments of the invention there is provided a method of identifying a candidate organometallic complex for catalyzing a chemical (organic) reaction. The method, according to this aspect of the invention, is effected by screening the abovementioned library of organometallic complexes, by means of determining a catalytic activity of the organometallic complexes in the organic reaction, thereby identifying the candidate organometallic complex. Optionally, a candidate is identified by selecting a target catalytic activity and identifying a complex having a catalytic activity of at least the target activity. In some embodiments, more than one candidate complex is identified.

As used herein, the term "catalyzing" describes a function of promoting a chemical reaction which otherwise is very slow, does not occur or occurs at substantially low conversion rate and/or yield. Catalyzing a chemical reaction can be effected in the presence of a catalytic or stoichiometric amount of the complex.

Similarly, the phrase "catalytic activity" is used to describe an activity in promoting a chemical reaction, either catalytic or stoichiometric.

Determining a catalytic activity of organometallic complexes is well within the capabilities of those skilled in the art, and can be effected, for example, by determining the turnover number (TON) in a reaction. The complex or complexes that exhibit the highest turnover number in the selected chemical reaction is identified as a candidate catalyst for performing this reaction.

Many chemical reactions have been shown to efficiently utilize pincer type complexes. These include, for example, Heck reaction (using palladium complexes), Suzuki-Miyaura couplings (using, for example, palladium complexes), dehydrogenation of alkanes (using, for example, iridium complexes), hydrogen transfer reactions (using, for example, ruthenium complexes), aldolic condensation (using, for example, platinum or palladium complexes), asymmetric allylic alkylation (using, for example, palladium complexes), and catalytic dehydrogenation of amines and alcohols.

Other applications of the compounds and complexes described herein include cyclopropanation of alkenes, dehydrogenative esterification, and amidation.

Thus, in some embodiments, a combinatorial library of organometallic complexes as described herein is screened for an efficient catalyst for Heck reaction. In these embodiments, an exemplary combinatorial library can include organometallic complexes having Formula V as described herein, which all share the presence of one or more diarylphosphine moiety, and which differ from one another by the nature or number of the diarylphosphine moieties, or by at least one of the variables n and $R_1$-$R_5$. Such a combinatorial library can be also used for screening for a catalyst for dehydrogenation of saturated hydrocarbons or for dehydrogenative coupling of alcohols with amines.

In some embodiments, a combinatorial library of organometallic complexes as described herein is screened for an efficient catalyst for an allylic alkylation reaction. In these embodiments, an exemplary combinatorial library can include organometallic complexes having Formula V as described herein, which all share the presence of one or more dialkylphosphine moiety, and which differ from one another by the nature or number of the dialkylphosphine moieties, or by at least one of the variables n and $R_1$-$R_5$. Such a combinatorial library can be also used for screening for a catalyst for a Heck reaction, a Suzuki reaction, a Kharasch reaction, a hydrogenation, a dehydrogenation, and/or an aldol condensation.

As demonstrated in the Examples section, organometallic complexes of embodiments of the present invention may be highly efficient catalysts of chemical reactions (e.g., Heck reaction). As further discussed herein, various chemical reactions are performed in the presence of pincer-type organometallic complexes.

Hence, according to another aspect of embodiments of the present invention, there is provided a chemical reaction performed in the presence of an organometallic complex as described herein, for example, an organometallic complex identified as a catalyst using the screening method described hereinabove.

Exemplary chemical reactions to be catalyzed by the organometallic complexes described herein are listed hereinabove.

As discussed hereinabove, the pincer ligands and organometallic complexes described herein may be readily prepared by a process utilizing compounds having the abovementioned Formulas IIIa and IIIb, as described herein. In order to facilitate such a process, the present inventors have prepared novel exemplary compounds having Formulas IIIa and IIIb, and developed novel synthetic methodologies for preparing such compounds.

Hence, according to another aspect of embodiments of the present invention, there is provided an azide-containing compound having the general Formula VI:

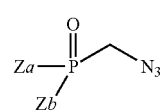

Formula VI wherein Za and Zb are each independently selected from the group consisting of a substituted or non-substituted aryl, a substituted or non-substituted alkyl and a substituted or non-substituted cycloalkyl.

Formula VI corresponds to general Formula IIIa described hereinabove, wherein $R_1$ and $R_2$ in Formula IIIa are hydrogen, n is 1, Xa is phosphorus, Wa is oxo (i.e., =O), and the variables $Z_1$ and $Z_2$ in Formula IIIa correspond to the variables Za and Zb in Formula VI.

It is to be noted that compounds having Formula IIIa as described herein, in which n is than 1 and/or $R_1$ and $R_2$ are other than hydrogen, are also contemplated herein.

According to another aspect of embodiments of the present invention, there is provided an alkyne-containing compound having the general Formula VII:

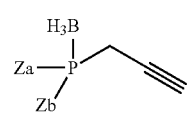

Formula VII wherein Za and Zb are each independently selected from the group consisting of a substituted or non-substituted aryl, a substituted or non-substituted alkyl and a substituted or non-substituted cycloalkyl.

Formula VII corresponds to general Formula IIIb described hereinabove, wherein $R_3$ and $R_4$ in Formula IIIb are hydrogen, n is 1, Xb is phosphorus, Wb is $BH_3$, and the variables $Z_3$ and $Z_4$ in Formula IIIb correspond to the variables Za and Zb in Formula VII.

It is to be noted that compounds having Formula IIIb as described herein, in which n is than 1 and/or $R_3$ and $R_4$ are other than hydrogen, are also contemplated herein.

In some embodiments, Za and Zb in Formula VI and/or Formula VII are each independently a substituted or non-substituted aryl. Such a compound comprises a diarylphosphine oxide group.

In some embodiments, at least one of Za and Zb in Formula VI and/or Formula VII is a substituted or non-substituted alkyl or a substituted or non-substituted cycloalkyl. Such a compound comprises an alkylphosphine oxide group. Optionally, each of Za and Zb is independently selected from the group consisting of a substituted or non-substituted alkyl and a substituted or non-substituted cycloalkyl. Such a compound comprises a dialkylphosphine oxide group.

Processes for the preparation of diarylphosphine-containing compounds having Formula VI and Formula VII are exemplified in the Examples section herein.

Hence, according to another aspect of embodiments of the present invention, there is provided a process for preparing an azide-containing compound of general Formula VI described hereinabove, wherein Za and Zb are each independently a substituted or non-substituted aryl. The process comprises converting a diaryl halophosphine containing the aryl groups Za and Zb described hereinabove (e.g., ZaZbPF, ZaZbPCl, ZaZbPBr, or ZaZbPI, wherein Za and Zb are each aryl as defined and exemplified herein) to a corresponding hydroxymethyldiarylphosphine oxide (e.g., ZaZbP(=O)—$CH_2OH$), and reacting the hydroxymethyldiarylphosphine oxide with an azide (e.g., sodium azide) to obtain the compound of Formula VI.

In exemplary embodiments, the hydroxy group of the hydroxymethyldiarylphosphine oxide is first reacted with an agent (e.g., tosyl chloride) that facilitates reaction (e.g., nucleophilic substitution) with an azide.

In an exemplary embodiment, the hydroxymethyldiarylphosphine oxide is prepared by reacting the diaryl halophosphine with formaldehyde (e.g., in an acidic aqueous solution).

According to another aspect of embodiments of the present invention, there is provided a process for preparing an alkyne-containing compound of general Formula VII described hereinabove, wherein Za and Zb are each independently a substituted or non-substituted aryl. The process comprises converting a diarylphosphine containing the aryl groups Za and Zb (e.g., as described hereinabove) to a corresponding phosphine-borane complex (e.g., ZaZbP(—$BH_3$)—Cl), and reacting the phosphine-borane complex with a reactive propargyl.

According to exemplary embodiments, the phosphine-borane complex is contacted with a very strong base (e.g., n-butyl lithium), and the reactive propargyl is a propargyl substituted by a leaving group such as halide (e.g., propargyl bromide), such that the phosphine-borane complex reacts with the reactive propargyl by nucleophilic substitution.

As discussed herein, the present inventors have surprisingly uncovered that compounds having general Formulas VI wherein Za and/or Zb are alkyl can not be readily prepared according to a process corresponding to the process described above for diarylphosphines (e.g., by converting a dialkyl halophosphine to a hydroxymethyldialkylphosphine oxide).

As exemplified in the Examples section, the present inventors have developed various alternative synthetic processes for preparing such compounds.

Hence, according to another aspect of embodiments of the present invention, there is provided a process for preparing the compound having general Formula VI, wherein at least one of Za and Zb is a substituted or non-substituted alkyl or cycloalkyl.

According to some embodiments, the process comprises converting a corresponding halophosphine (e.g., ZaZbPF, ZaZbPCl, ZaZbPBr, or ZaZbPI, wherein Za and Zb are as defined in Formula VI) to a corresponding phosphonylacetic acid (e.g., ZaZbP(=O)—$CH_2CO_2H$, and converting the phosphonylacetic acid to a bromomethylphosphine oxide (e.g., ZaZbP(=O)—$CH_2Br$).

Optionally, the phosphonylacetic acid is obtained by reacting the halophosphine with a compound comprising an acetate ester moiety substituted with a leaving group (e.g., halogen), for example, a bromoacetate ester, so as to obtain a phosphonylacetate ester. The phosphonylacetate ester may then be hydrolyzed so as to obtain the phosphonylacetic acid.

In exemplary embodiments, the phosphonylacetic acid is converted to the bromomethylphosphine oxide by reaction with $Br_2$.

According to some embodiments, the process comprises converting a corresponding halophosphine (e.g., a halophosphine described hereinabove) to a phosphonylacetate (e.g., a phosphonylacetate ester ZaZbP(=O)—$CH_2CO_2R$, wherein R is alkyl, cycloalkyl, aryl), converting the phosphonylacetate to a corresponding alpha-bromo phosphonyl acetate, and converting the alpha-bromo phosphonyl acetate to a corresponding bromomethylphosphine oxide.

A phosphonylacetate ester may optionally be obtained as described hereinabove.

In exemplary embodiments, the phosphonylacetate is converted to a dibromo phosphonyl acetate before being converted (e.g., by reaction with $SnCl_2$) to the bromo phosphonyl acetate.

Optionally, the alpha-bromo phosphonyl acetate is converted to the bromomethylphosphine oxide by heating (e.g., at about 160° C.). In exemplary embodiments, a bromomethylacetate ester (e.g., ZaZbP(=O)—$CHBrCO_2R$ wherein R is alkyl, cycloalkyl, aryl) is converted to a bromomethylacetate that is a bromomethylacetic acid (e.g., ZaZbP(=O)—$CHBrCO_2H$), for example, by acid hydrolysis, and the bromomethylacetic acid is subsequently converted to the abovementioned bromomethylphosphine oxide.

According to the embodiments described hereinabove, the process further comprises reacting the obtained bromomethylphosphine oxide with an azide (e.g., sodium azide) to obtain the compound of Formula VI.

The abovementioned alkylphosphine oxide-containing compounds having Formula VI, as well as the various intermediates (e.g., bromomethyl derivatives, acetate derivatives of alkylphosphine oxides) described hereinabove in the process for preparing alkylphosphine-containing compounds of Formula VI, represent a wide variety of novel alkylphosphine oxide derivatives which may be prepared according to the novel processes described herein. Such alkylphosphine oxide derivatives may be useful for a wide variety of applications (e.g., in organic syntheses), and cannot be readily synthesized by previously used methods, as described herein.

Hence, according to another aspect of embodiments of the present invention, there is provided a compound having a general Formula VIII:

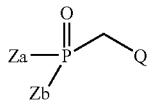

Formula VIII wherein:

Q is selected from the group consisting of azide, halide, carboxy, and hydroxy, and at least one of Za and Zb (and optionally each of Za and Zb) is a substituted or non-substituted alkyl or a substituted or non-substituted cycloalkyl.

In some embodiments, Q is other than COOH.

As further discussed herein, the present inventors have surprisingly uncovered that compounds having general Formulas VII wherein Za and/or Zb are alkyl can not be readily prepared according to a process corresponding to the process described above for diarylphosphines (e.g., by reacting a phosphine-borane complex with a propargyl halide). As exemplified in the Examples section, the present inventors have developed synthetic processes for overcoming this obstacle.

Hence, according to another aspect of embodiments of the present invention, there is provided a process for preparing the compound having general Formula VII, wherein at least one of Za and Zb is a substituted or non-substituted alkyl or cycloalkyl. The process comprises reacting a propargyl Grignard reagent (e.g., a propargyl magnesium halide, such as $(CH_3)_3Si-C{\equiv}C-CH_2-MgBr$) with a halophosphine-borane complex (e.g., $ZaZbP(-BH_3)-Cl$, $ZaZbP(-BH_3)-Br$) to obtain the compound of Formula VII. Optionally, the propargyl Grignard reagent is protected at one end of the alkyne group, for example, by a trimethylsilyl (TMS) group, and the process further comprises removing the protecting group subsequent to reaction of the phosphine-borane complex with the reactive propargyl.

As used herein throughout, the term "alkyl" refers to a saturated or unsaturated aliphatic hydrocarbon including straight chain and branched chain groups. In some embodiments, the alkyl group has 1 to 20 carbon atoms. In some embodiments, the alkyl is a medium size alkyl having 1 to 10 carbon atoms. In some embodiments, the alkyl is a lower alkyl having 1 to 4 carbon atoms. The alkyl group may be substituted or non-substituted. When substituted, the substituent group can be, for example, cycloalkyl, aryl, heteroaryl, heteroalicyclic, halo, hydroxy, alkoxy, aryloxy, thiohydroxy, thioalkoxy, thioaryloxy, disulfide, sulfinyl, sulfonyl, sulfonate, sulfate, cyano, nitro, phosphonyl, phosphinyl, oxo, carbonyl, thiocarbonyl, urea, thiourea, carbamyl, thiocarbamyl, amido, carboxylate, sulfonamido and amine, as these terms are defined herein. In some embodiments, the substituent is alkyl, cycloalkyl, aryl, heteroaryl, heteroalicyclic, alkoxy, thioalkoxy, hydroxy, thiol, amine, nitro and/or cyano.

A "cycloalkyl" group refers to an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene and adamantane. A cycloalkyl group may be substituted or non-substituted. When substituted, the substituent group can be, for example, cycloalkyl, aryl, heteroaryl, heteroalicyclic, halo, hydroxy, alkoxy, aryloxy, thiohydroxy, thioalkoxy, thioaryloxy, disulfide, sulfinyl, sulfonyl, sulfonate, sulfate, cyano, nitro, phosphonyl, phosphinyl, oxo, carbonyl, thiocarbonyl, urea, thiourea, carbamyl, thiocarbamyl, amido, carboxylate, sulfonamido and amine, as these terms are defined herein. In some embodiments, the substituent is alkyl, cycloalkyl, aryl, heteroaryl, heteroalicyclic, alkoxy, thioalkoxy, hydroxy, thiol, amine, nitro and/or cyano.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or non-substituted. When substituted, the substituent group can be, for example, cycloalkyl, aryl, heteroaryl, heteroalicyclic, halo, hydroxy, alkoxy, aryloxy, thiohydroxy, thioalkoxy, thioaryloxy, disulfide, sulfinyl, sulfonyl, sulfonate, sulfate, cyano, nitro, phosphonyl, phosphinyl, oxo, carbonyl, thiocarbonyl, urea, thiourea, carbamyl, thiocarbamyl, amido, carboxylate, sulfonamido and amine, as these terms are defined herein. In some embodiments, the substituent is alkyl, cycloalkyl, aryl, heteroaryl, heteroalicyclic, alkoxy, thioalkoxy, hydroxy, thiol, amine, halogen, nitro and/or cyano.

A "heteroaryl" group refers to a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furan, thiophene, imidazole, oxazole, thiazole, pyrazole, pyridine, pyrimidine, quinoline, isoquinoline and purine. The heteroaryl group may be substituted or non-substituted. When substituted, the substituent group can be, for example, cycloalkyl, aryl, heteroaryl, heteroalicyclic, halo, hydroxy, alkoxy, aryloxy, thiohydroxy, thioalkoxy, thioaryloxy, disulfide, sulfinyl, sulfonyl, sulfonate, sulfate, cyano, nitro, phosphonyl, phosphinyl, oxo, carbonyl, thiocarbonyl, urea, thiourea, carbamyl, thiocarbamyl, amido, carboxylate, sulfonamido and amine, as these terms are defined herein. In some embodiments, the substituent is alkyl, cycloalkyl, aryl, heteroaryl, heteroalicyclic, alkoxy, thioalkoxy, hydroxy, thiol, amine, halogen, nitro and/or cyano.

A "heteroalicyclic" group refers to a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or non-substituted. When substituted, the substituent group can be, for example, cycloalkyl, aryl, heteroaryl, heteroalicyclic, halo, hydroxy, alkoxy, aryloxy, thiohydroxy, thioalkoxy, thioaryloxy, disulfide, sulfinyl, sulfonyl, sulfonate, sulfate, cyano, nitro, phosphonyl, phosphinyl, oxo, carbonyl, thiocarbonyl, urea, thiourea, carbamyl, thiocarbamyl, amido, carboxylate, sulfonamido and amine, as these terms are defined herein. In some embodiments, the substituent is selected from the group consisting of alkyl, cycloalkyl, aryl, heteroaryl, heteroalicyclic, alkoxy, thioalkoxy, hydroxy, thiol, amine, nitro and/or cyano. Representative examples are 4,5-dihydroimidazole, piperidine, piperazine, tetrahydrofuran, tetrahydropyran, morpholine and the like.

As used herein, the terms "amine" and "amino" refer to a —NR'R" group, wherein R' and R" are selected from the group consisting of hydrogen and substituted or non-substituted alkyl, cycloalkyl, heteroalicyclic (bonded through a ring carbon), aryl, and heteroaryl (bonded through a ring carbon). In some embodiments, R' and R" are each independently hydrogen or an alkyl comprising 1 to 4 carbon atoms. In some embodiments, R' and R" are each hydrogen.

A "hydroxy" group refers to an —OH group.

An "azide" group refers to a —N=N$^+$=N (—N$_3$) group.

An "alkoxy" group refers to both —O-alkyl and —O-cycloalkyl groups.

An "aryloxy" group refers to both —O-aryl and —O-heteroaryl groups.

A "thiohydroxy" group or "thiol" refers to a —SH group.

A "thioalkoxy" group refers to both —S-alkyl and —S-cycloalkyl groups.

A "thioaryloxy" group refers to both —S-aryl and —S-heteroaryl groups.

A "disulfide" group refers to both a —S-thioalkoxy and a —S-thioaryloxy group.

A "carbonyl" group refers to a —C(=O)-R' group, where R' is defined as hereinabove.

A "thiocarbonyl" group refers to a —C(=S)—R' group, where R' is as defined herein.

An "oxo" group refers to a =O group.

A "carboxylate" encompasses both —C(=O)—O—R' and R'C(=O)—O— groups, where R' is as defined herein.

A "thiocarboxy" or "thiocarboxylate" group refers to both —C(=S)—O—R' and —O—C(=S)R' groups, where R' is as defined herein.

A "halo" or "halogen" group refers to fluorine, chlorine, bromine or iodine.

A "sulfinyl" group refers to an —S(=O)—R' group, where R' is as defined herein.

A "sulfonyl" group refers to an —S(=O)$_2$—R' group, where R' is as defined herein.

A "sulfonate" group refers to an —S(=O)$_2$—O—R' group, where R' is as defined herein.

A "sulfate" group refers to an —O—S(=O)$_2$—O—R' group, where R' is as defined as herein.

A "sulfonamide" or "sulfonamido" group encompasses both —S(=O)$_2$—NR'R" and R'S(=O)$_2$—N(R')— groups, where R' and R" are as defined herein.

A "carbamyl" or "carbamate" group encompasses —OC(=O)—NR'R" and R'OC(=O)—NR"— groups, where R' and R" are as defined herein.

A "thiocarbamyl" or "thiocarbamate" group encompasses —OC(=S)—NR'R" and R'OC(=S)—NR"— groups, where R' and R" are as defined herein.

An "amide" or "amido" group encompasses —C(=O)—NR'R" and R'C(=O)—NR"— groups, where R' and R" are as defined herein.

A "urea" group refers to an —N(R')—C(=O)—NR"R'" group, where each of R' and R" is as defined herein, and R'" is defined as R' and R" are defined herein.

A "nitro" group refers to an —NO$_2$ group.

A "cyano" group refers to a —C≡N group.

The term "phosphonyl" or "phosphonate" describes a —P(=O)(OR')(OR") group, with R' and R" as defined hereinabove.

The term "phosphate" describes an —O—P(=O)(OR')(OR") group, with each of R' and R" as defined hereinabove.

The terms "phosphinyl" and "phosphine" describe a —PR'R" group, with each of R' and R" as defined hereinabove.

The term "phosphine oxide" describes a —P(=O)R'R" group, where R' and R" are as defined herein.

The term "thiourea" describes a —N(R')—C(=S)—NR"R'" group, with each of R', R" and R'" as defined hereinabove.

The term "alkene" refers to an alkyl, as defined herein, which comprises at least two carbon atoms, and at least one carbon-carbon double bond.

The term "alkyne" or "alkynyl" refers to an alkyl, as defined herein, which comprises at least two carbon atoms, and at least one carbon-carbon triple bond.

An example of alkyne is propargyl, which comprises 3 carbon atoms and one triple bond. In some embodiments, where n in the general Formula I herein is 1, the compounds is made by assembling an azide and a propargyl.

As used herein the term "about" refers to ±10%.

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" or "process" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Materials and Methods

Materials:

Bis(phenyl) propargylphosphine borane complex (Compound 3a) was prepared as described in Detz et al. [*Org. Lett.* 2006, 8, 3227].

Tetramethylethylenediamine(TMEDA)-PdCl$_2$ was prepared as described in De Graaf et al. [*Organometallics* 1989, 8, 2907].

General Methods:

Oxygen- and moisture-sensitive reactions were carried out under an atmosphere of purified nitrogen in a glove-box equipped with an inert gas purifier, or by using standard Schlenk techniques.

Dry triethylamine was obtained by distillation from CaH$_2$.

Solvents were purified by passing through a column of activated alumina under an inert atmosphere.

All commercially available reagents were used as received, unless indicated otherwise.

Analytical thin layer chromatography (TLC) was performed on pre-coated silica gel 60 F-254 plates (particle size 0.040-0.055 mm, 230-400 mesh) and visualization was accomplished using UV light or by staining with basic KmnO$_4$ dye.

NMR spectra were recorded at 300 MHz/75 MHz ($^1$H/$^{13}$C NMR) in CDCl$_3$ unless otherwise stated on a Bruker ADVANCE 300 MHz spectrometer at 23° C. Chemical shifts (δ) are reported in parts per million and the residual solvent peak was used as an internal standard (CDCl$_3$: δ 7.261/77.0, 1H/13C NMR). $^{31}$P NMR signals are in ppm and referenced to external 85% H$_3$PO$_4$. Data are reported as follows: chemical shift, multiplicity (s=singlet, d=doublet, t=triplet, q=quartet, p=pentet, m=multiplet, b=broad), integration, and coupling constant(s) (Hz).

Example 1

Synthesis of Azide Derivatives of Diarylphosphines
Synthesis of Azidomethyl Diphenylphosphine Oxide (Compound 1)

The synthesis of Compound 1 is depicted in FIG. 3.

Synthesis of hydroxymethyl diphenylphosphine oxide: Hydroxymethyl diphenylphosphine oxide was prepared according to Lawrence & Jackson [*J. Chem. Soc., Perkin Trans.* 2002, 1, 2260]. To a mixture of HCl (18.9 ml) and aqueous formaldehyde (18.9 ml, 37 wt %) was added diphenyl chlorophosphine (2.80 ml, 10.6 mmol). The reaction mixture was heated to 100° C. for 18 hours under a nitrogen atmosphere. The reaction was neutralized with aqueous NaHCO$_3$, and the aqueous phase was extracted with CH$_2$Cl$_2$ (3×30 ml). The organic phase was dried with anhydrous Na$_2$SO$_4$. Hydroxymethyl diphenylphosphine oxide (2.907 grams, 89% yield) was obtained after evaporation of the solvent as a colorless oil.

$^1$H NMR (CDCl$_3$) δ: 7.71-7.36 (m, 10H, Ar), 6.16 (s, 1H), 4.34 (d, 2H, J=2.1 Hz).

$^{13}$C NMR (CDCl$_3$) δ: 133.9 (d, J$_{CP}$=2.6 Hz), 133.2 (d, J$_{CP}$=9.2 Hz), 132.3 (d, J$_{CP}$=97 Hz), 130.4 (d, J$_{CP}$=11.6 Hz), 62.9 (d, J$_{CP}$=75 Hz).

$^{31}$P NMR (202 MHz) δ: 28.6.

Synthesis of azidomethyl diphenylphosphine oxide: This compound was prepared according to the procedure described by Detz et al. [*Org. Lett.* 2006, 8, 3227], with modification. To 50 ml of freshly distilled pyridine was added hydroxymethyl diphenylphosphine oxide (2.907 grams, 12.5 mmol) and freshly recrystallized toluene sulfonyl chloride (2.862 grams, 15 mmol). The obtained mixture was stirred at room temperature for 18 hours under a nitrogen atmosphere. The mixture was then diluted with CH$_2$Cl$_2$ (50 ml) and washed with H$_2$O (3×50 ml). The solvent was evaporated, and the obtained residue was then re-dissolved in anhydrous dimethyl formamide (30 ml). To this mixture was added sodium azide (2.031 grams, 31.25 mmol). The reaction mixture was heated to 110° C. for 5 hours under a nitrogen atmosphere. The reaction was quenched with water, and was extracted with CH$_2$Cl$_2$ (3×50 ml). The organic phase was dried with anhydrous Na$_2$SO$_4$. The product was purified on silica, using ethyl acetate as eluent, to give the product (1.53 gram, 51% yield) as a white powder.

$^1$H NMR (CDCl$_3$) δ: 7.78-749 (m, 10H), 3.98 (d, 2H, J$_{HP}$=7.5 Hz, CH$_2$).

$^{13}$C NMR (CDCl$_3$) δ: 132.6 (d, J$_{CP}$=2.7 Hz), 131.2 (d, J$_{CP}$=9.6), 130.0 (d, J$_{CP}$=101 Hz), 128.8 (d, J$_{CP}$=12.0 Hz), 49.5 (d, J$_{CP}$=76.5 Hz).

$^{31}$P NMR δ: 28.8.

B. Synthesis of Azidomethyl Phenyl Sulfide (Compound 2):

The structure of Compound 2 is presented in FIG. 2.

To 5.3 ml of freshly distilled acetonitrile was added chloromethyl phenyl sulfide (1.0 gram, 6.303 mmol), sodium azide (614 mg, 9.45 mmol) and crown ether-5 (0.250 ml, 1.261 mmol). The solution was stirred for 48 hours under a nitrogen atmosphere and 10 ml water were thereafter added thereto. The aqueous phase was extracted with CH$_2$Cl$_2$ (3×10 ml) and the combined organic layers were washed with water (15 ml) and brine (15 ml). The organic phase was dried with anhydrous Na$_2$SO$_4$. The product (994 mg, 95% yield) was obtained after evaporation of the solvent as a pale yellow oil.

$^1$H NMR (CDCl$_3$) δ: 7.50-7.47 (m, 2H), 7.34-7.30 (m, 3H), 4.52 (s, 2H, CH$_2$).

$^{13}$C NMR (CDCl$_3$) δ: 131.5, 129.6, 128.1, 56.3 (CH$_2$).

Example 2

Synthesis of Alkyne Derivative of Diarylphosphines

The synthesis of alkyne derivatives of diarylphosphines is depicted in FIG. 3.

Synthesis of bis(2-methoxyphenyl) propargylphosphine borane complex (Compound 3b): Bis(2-methoxyphenyl) phosphine borane complex was prepared according to Busacca & Senanayake [*Org. Lett.* 2005, 7, 4277]. To a solution of the bis(2-methoxyphenyl)phosphine borane complex (110 mg, 0.423 mmol) in tetrahydrofuran (2 ml), n-butyl lithium (1.6 M in hexane, 265 μl, 0.423 mmol) was added at −78° C. under argon atmosphere. The solution was stirred for 15 minutes and propargylbromide (80% in toluene, 110 μl, 0.465 mmol) was then added, quenching the phosphine anion at −78° C. After 15 minutes, water was added and the solution was warmed to room temperature. The aqueous phase was extracted with ethyl acetate (3×10 ml) and the combined organic layers were washed with water (20 ml) and brine (20 ml). The organic phase was dried with anhydrous Na2SO4. The product (87 mg, 69% yield) was obtained after evaporation of the solvent as a pale yellow oil.

$^1$H NMR (CDCl$_3$) δ: 7.56-7.44 (m, 4H), 6.98-6.90 (m, 4H), 3.73 (s, 6H, O—CH$_3$) 3.51-3.45 (dd, 2H, $J_{HH}$=2.7 Hz, $J_{HP}$=13.7 Hz, CH$_2$), 1.85 (dt, 1H, $J_{HH}$=2.7 Hz, $J_{HP}$=5.7 Hz, C≡C—H), 1.60-0.25 (br m, 3H, BH$_3$).

$^{13}$C NMR (CDCl$_3$) δ: 161.4, 135.3, 333.6, 121.2, 116.5, 111.6, 77.2 (C≡C—H), 71.4 (C≡C—H), 55.9 (OCH$_3$), 17.2 (CH$_2$). The $^{13}$C assignments were confirmed by DEPT (distortionless enhancement by polarization transfer) experiment.

$^{31}$P NMR δ: 19.2 (d, $J_{PB}$=61 Hz)

Mass spectrometry (MS-MALDI) m/z: 285 [M—BH$_3$].

Example 3

Preparation of Pincer Ligands

A variety of pincer ligands were prepared using the Huisgen dipolar cycloaddition of azides and alkynes to yield triazoles. Precursors comprising an azidomethyl group, such as described in Example 1, were reacted with precursors comprising a propargyl (prop-2-ynyl) group, such as those described in Example 2, resulting in the formation of 1,4-substituted triazole pincer ligands.

Preparation of Protected Forms of Pincer Ligands:

Phosphine donor groups in the pincer ligand were obtained by using precursors comprising a protected form (phosphine oxide or phosphine-borane complex) of the phosphine group.

As an example, the synthesis of the protected form (borane complex) of the pincer ligand Compound 7 (see, FIG. 2) was performed as follows:

Synthesis of protected form of Compound 7: To the alkyne precursor bis(phenyl) propargylphosphine borane complex (Compound 3a) (144 mg, 0.605 mmol) in 0.6 ml tetrahydrofurane was added the azide precursor azidomethyl phenyl sulfide (Compound 2) (100 mg, 0.605 mmol). In a separate vessel, CuSO$_4$.5H$_2$O (75.3 mg, 0.303 mmol) was dissolved in 0.6 ml distilled water. Upon addition of sodium ascorbate (599 mg, 3.025 mmol) to the aqueous mixture, the resulting dark brown mixture was quickly added to the reaction. The obtained reaction mixture was stirred at room temperature for 14 hours under nitrogen. The aqueous phase was extracted with ethyl acetate (3×10 ml) and the combined organic layers were washed with water (20 ml) and brine (20 ml). The organic phase was dried with anhydrous Na$_2$SO$_4$. The protected form (borane complex) of Compound 7 (189 mg, 80% yield) was obtained after evaporation as a white powder.

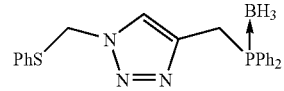

Protected form of Compound 7

$^{31}$P NMR (202 MHz): 14.5 (d).

$^1$H NMR (500 MHz, D$_2$O) δ: 7.69-7.65 (m, 4H), 7.36 (s, 1H, triazole-H), 7.08-7.07 (m, 2H), 6.97-6.87 (m, 6H), 6.87 (m, 3H), 4.77 (s, 2H, CH$_2$—S), 3.51 (d, 2H, $J_{HP}$=11 Hz, CH$_2$—P), 2.2-1.5 (br m, 3H, BH$_3$).

$^{13}$C NMR (500 MHz, D$_2$O) δ: 141.1, 134.2 (d, $J_{CP}$=9.23 Hz), 134.1, 133.8, 132.8 (d, $J_{CP}$=2.62 Hz), 131.0, 130.6, 130.4 (d, $J_{CP}$=9.56 Hz), 129.9, 129.8, 129.7, 129.6, 129.5, 129.3, 124.5 (d, $J_{CP}$=3.18 Hz), 54.67 (CH$_2$—S), 26.2 (d, $J_{CP}$=36.1 Hz, CH$_2$—P). The $^{13}$C assignments were confirmed by DEPT experiments.

Mass spectroscopy (MS-MALDI): m/z (%)=402 (55) [M−1]$^+$.

Using essentially the same procedures, the following protected forms of pincer ligands were obtained (see, FIG. 2):

Synthesis of protected form of Compound 5: The azide precursor Compound 1 was reacted with the alkyne precursor Compound 3a according to the above-described procedures to obtain the following compound:

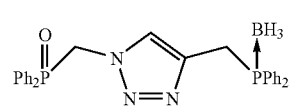

Protected form of Compound 5

$^1$H NMR (CDCl$_3$) δ: 7.64-7.61 (m, 10H), 7.43-7.36 (m, 11H), 5.11 (d, 2H, $J_{HP}$=6.9 Hz, N—CH$_2$—P), 3.66 (d, 2H, $J_{HP}$=11.1 Hz, C—CH$_2$—P), 1.5-0.3 (br m, 3H, BH$_3$).

$^{13}$C NMR (75 MHz) δ: 138.8 (d, $J_{CP}$=2.74 Hz), 132.5 (d, $J_{CP}$=2.45 Hz), 132.0 (d, $J_{CP}$=9.23 Hz), 131.0 (d, $J_{CP}$=1.91 Hz) 130.8 (d, $J_{CP}$=9.27 Hz), 128.6, 128.5 (d, $J_{CP}$=68.46 Hz), 128.4, 128.3, 127.6 (d, $J_{CP}$=20.65 Hz), 124.0 (d, $J_{CP}$=2.78 Hz), 49.8 (d, $J_{CP}$=70.36 Hz, CH$_2$—P), 24.0 (d, $J_{CP}$=35.83 Hz CH$_2$—P). The $^{13}$C assignments were confirmed by DEPT.

$^{31}$P NMR (121 MHz) δ: 23.62 (s, 1P, P=O) 14.78 (m, 1P, P—BH$_3$).

Synthesis of protected form of Compound 6: The azide precursor Compound 1 was reacted with the alkyne precursor 2-ethynylpyridine according to the above-described procedures to obtain the following compound:

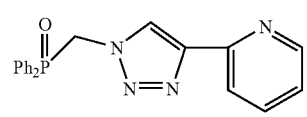

Protected form of Compound 6

$^1$H NMR (300 MHz, CDCl$_3$) δ: 8.58 (s, 1H), 8.44 (s, 1H), 8.02 (d, 1H), 7.81-7.47 (m, 11H, Ar), 7.21 (m, 2H), 5.32 (d, 2H, $J_{HP}$=7.2 Hz, CH$_2$—P).

$^{13}$C NMR (125 MHz) δ: 149.7, 149.4, 136.8, 133.0 (d, $J_{CP}$=2.7 Hz), 131.2 (d, $J_{CP}$=10.0 Hz), 129.3, 129.1 (d, $J_{CP}$=12.1 Hz), 123.4, 122.9, 120.2, 50.3 (d, $J_{CP}$=70.1 Hz, CH$_2$—P).

$^{31}$P NMR (120 MHz) δ: 24.4.

Mass spectroscopy (MS-ESI$^+$): m/z=361 [M+1].

Synthesis of protected form of Compound 8: The azide precursor Compound 2 was reacted with the alkyne precursor Compound 3b according to the above-described procedures to obtain the following compound:

Protected form of Compound 8

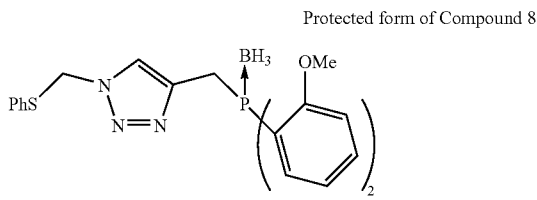

$^1$H NMR (500 MHz, CDCl$_3$) δ: 7.80-7.75 (m, 2H, Ar) 7.56 (d, 1H), 7.05-7.03 (m, 4H Ar), 6.88-6.87 (M, 2H, Ar), 6.67-6.64 (m, 2H, Ar), 6.34-6.31 (m, 2H, Ar), 4.62 (s, 2H, CH$_2$—S), 4.26 (d, 2H, J$_{HP}$=12.5 Hz, CH$_2$—P), 3.18 (s, 6H, O—Me), 2.2-1.8 (br m, 3H, BH$_3$).

$^{13}$C NMR (125 MHz) δ: 163.1, 142.5, 134.4 (d, J$_{CP}$=10.9 Hz), 134.4 (d, J$_{CP}$=1.76 Hz), 133.8, 130.9, 129.7, 129.5, 129.3, 129.1, 124.0 (d, J$_{CP}$=2.98 Hz), 122.4 (d, J$_{CP}$=11.0 Hz), 119.0 (d, J$_{CP}$=54.6 Hz), 113.0 (d, J$_{CP}$=4.6 Hz), 56.8 (O—Me), 54.5 (CH$_2$—S), 25.1 (d, J$_{CP}$=50.0 Hz, CH$_2$—P). The $^{13}$C assignments were confirmed by DEPT.

$^{31}$P NMR (202 MHz) δ: 15.2 (m).

Mass spectroscopy (MS-ESI$^+$): m/z (%)=462 (100) [M−1]$^+$.

Deprotection of Phosphine Groups of Pincer Ligands:

Deprotection of Compound 5: The phosphine oxide group of the protected form of Compound 5 was reduced as follows:

Trichlorosilane (934 μl, 9.25 mmol) and triethyl amine (2.60 ml, 18.5 mmol) were added to the protected form of Compound 5 (458.2 mg, 0.93 mmol) in toluene (30 ml) and dichloromethane (5 ml). This mixture was stirred in a closed, argon-filled flask and heated to 100° C. for 18 hours. The reaction mixture was then cooled and filtered through a pad of elite under inert conditions, resulting in the reduced phosphine. The obtained material was concentrated.

The phosphine-borane complex was then deprotected as follows:

The obtained material was re-dissolved in anhydrous tetrahydrofurane (10 ml). To this solution was added DABCO (124 mg, 1.11 mmol). The reaction mixture was then heated to 70° C. for 4 hours, resulting in full deprotection of the borane from the phosphine group. Remaining DABCO was removed by filtration through a short plug of silica. Washing with diethyl ether gave Compound 5 as a colorless solid (400 mg, 93% yield).

Compound 5

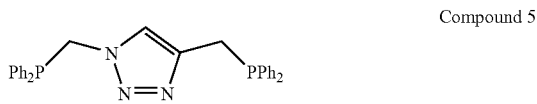

$^1$H NMR (500 MHz, CDCl$_3$) δ: 7.41-7.30 (m, 15H, Ar), 6.94 (s, 1H, triazole-H), 4.96 (d, 2H, J$_{HP}$=4.8 Hz, N—CH$_2$—P), 3.47 (s, 2H, C—CH$_2$—P).

$^{13}$C NMR (125 MHz) δ: 145.8 (d, J$_{CP}$=11.0 Hz), 139.5 (d, J$_{CP}$=14.0 Hz), 136.3 (d, J$_{CP}$=12.7 Hz), 134.7 (d, J$_{CP}$=13.9 Hz), 134.5 (d, J$_{CP}$=13.2 Hz), 131.5, 130.7, 130.6 (d, J$_{CP}$=3.8 Hz), 130.3, 130.2, 123.5, 55.8 (d, J$_{CP}$=19.6 Hz, N—CH$_2$—P), 27.1 (d, J$_{CP}$=14.9 Hz, C—CH$_2$—P). The $^{13}$C assignments were confirmed by DEPT.

$^{31}$P NMR (202 MHz) δ: −16.7.

Mass spectroscopy (MS-MALDI): m/z=488 [M+Na].

Elemental analysis: As the phosphine groups are air-sensitive, elemental percentages were calculated for the mono-phosphine oxide form: C, 69.85; H, 5.23; and di-oxide form: C, 67.60; H, 5.07. Found: C, 68.57; H, 5.98.

Using essentially the same procedures as described for deprotecting Compound 5, the following compounds were prepared:

Deprotection of Compound 6: Compound 6 was obtained by reducing the phosphine oxide of the protected form, according to the above-described procedures.

Compound 6

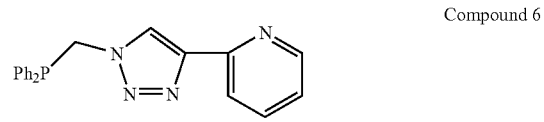

$^{31}$P NMR (120 MHz) δ: −13.4.

$^1$H NMR (300 MHz, CDCl$_3$) δ: 8.56 (d, 1H), 8.25 (d, 1H), 8.12 (s, 1H), 7.74 (t, 1H), 7.45-7.34 (m, 10H, Ar), 7.20 (m, 1H), 5.14 (d, 2H, J$_{HP}$=4.5 Hz, CH$_2$—P).

Deprotection of Compound 7: Compound 7 was obtained by converting the phosphine-borane complex of the protected form to a phosphine group, according to the above-described procedures.

Compound 7

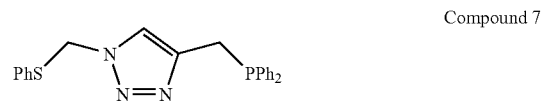

$^1$H NMR (500 MHz, CDCl$_3$) δ: 7.42-7.19 (m, 15H, Ar), 7.10 (s, 1H, triazole-H), 5.48 (s, 2H, CH$_2$—S), 3.50 (s, 2H, CH$_2$—P).

$^{13}$C NMR (125 MHz) δ: 14.2 (d, J$_{CP}$=10.8 Hz), 139.4 (d, J$_{CP}$=14.1 Hz), 134.6, 134.5, 134.1, 133.6, 131.2, 130.1, 130.4 (d, J$_{CP}$=7.5 Hz), 130.3, 122.8 (d, J$_{CP}$=6.9 Hz), 55.6 (CH$_2$—S), 27.1 (d, CH$_2$—P, J$_{CP}$=15.4 Hz). The $^{13}$C assignments were confirmed by DEPT.

$^{31}$P NMR (202 MHz) δ: −16.68.

Mass spectroscopy (MS-MALDI): m/z=390 [M+1].

Elemental analysis: Calculated C, 67.85; H, 5.18. Found: C, 67.05; H, 5.69.

Deprotection of Compound 8: Compound 8 was obtained by converting the phosphine-borane complex of the protected form to a phosphine group, according to the above-described procedures.

Compound 8

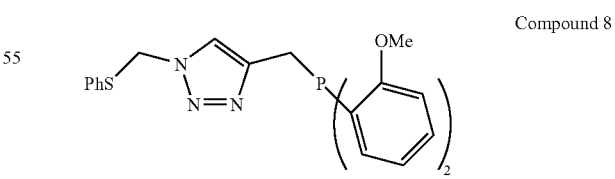

$^{31}$P NMR (202 MHz) δ: −33.7.

$^1$H NMR (300 MHz, CDCl$_3$) δ: 7.25-7.08 (m, 9H), 7.07-6.78 (m, 5H), 5.39 (s, 2H, CH$_2$—S), 3.70 (s, 6H, O—Me), 3.52 (s, 2H, CH$_2$—P). $^{13}$C NMR (202 MHz) δ: 161.2 (d, J$_{CP}$=13 Hz), 145.7 (d, J$_{CP}$=11.9 Hz), 133.0, 132.9, 132.3, 130.2, 129.3, 128.4, 142.3 (d, J$_{CP}$=15.8 Hz), 120.9, 120.8, 110.1, 55.5 (O—Me), 51.1 (d, CH$_2$—S), 21.4 (d, CH$_2$—P, J$_{CP}$=14.7 Hz). The $^{13}$C assignments were confirmed by DEPT.

Mass spectroscopy (MS-ESI$^+$): m/z=488 [M+K].

Elemental analysis: Calculated for phosphine oxide form: C, 61.92; H, 5.20. Found: C, 61.75; H, 5.90.

Example 4

Preparation of Palladium and Platinum Pincer Complexes

The preparation of exemplary palladium pincer complexes according to embodiments of the invention is depicted in FIG. 4.

Preparation of Compound 9: Compound 5 (20 mg; 0.043 mmol), tetramethylethylenediamine(TMEDA)-PdCl$_2$ (12 mg; 0.043 mmol) and triethylamine (10 equivalents) were combined in 2 ml of dimethylformamide. The resulting solution was heated at 70° C. for 12 hours. The solvent was evaporated and the residue was washed with ether (3×3 ml) and extracted with toluene/tetrahydrofuran (3×3 ml). The combined extractions were evaporated, resulting in pure compound 9 in a yield of 78%.

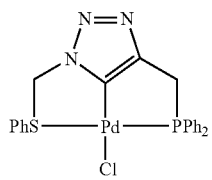

Compound 9

$^{31}$P {$^1$H} NMR (CDCl$_3$) 33.1 (d, J$_{PP}$=462.0 Hz); 23.4 (d, J$_{PP}$=462.0 Hz).

$^1$H NMR (CDCl$_3$): 7.30-6.79 (m, 20H, Ar), 4.86 (d, J$_{HP}$=4.7 Hz, 2H, N—CH$_2$—P), 3.68 (d, J$_{HP}$=5.2 Hz, 2H, C—CH$_2$—P).

$^{13}$C NMR (CDCl$_3$): 163.02 (bs, C$_{ipso}$), 132.61 (s, Ar), 132.55 (s, Ar), 132.48 (s, Ar), 132.40 (s, Ar), 132.31 (s, Ar), 131.33 (s, Ar), 130.72 (s, Ar), 130.31 (s, Ar), 128.88 (s, Ar), 128.70 (s, Ar), 128.56 (s, Ar), 128.40 (s, Ar), 128.12 (s, Ar), 67.25 (d, J$_{CP}$=30.0 Hz, N—CH$_2$—P), 52.34 (d, J$_{CP}$=39.5 Hz, C—CH$_2$—P) (assignment of $^{13}$C{$^1$H} NMR signals was confirmed by $^{13}$C DEPT).

Elemental analysis: Calculated: C, 55.46; H, 3.99. Found: C, 53.93; H, 3.78.

Using essentially the same procedures, the following complexes were prepared: Compound 10:

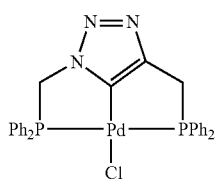

Compound 10

Compound 10 was prepared by complexing palladium to Compound 6.

$^{31}$P{$^1$H} NMR (CDCl$_3$): 21.4 (s).

$^1$H NMR (CDCl$_3$): 8.43-7.01 (m, 14H, Ar), 5.30 (d, J$_{HP}$=6.9 Hz, 2H, N—CH$_2$—P).

$^{13}$C NMR (CDCl$_3$): 153.92 (bs, C$_{ipso}$), 149.52 (s, Ar), 136.45 (s, Ar), 133.08 (s, Ar), 133.00 (s, Ar), 132.14 (s, Ar), 131.25 (d, J$_{CP}$=3.1 Hz), 129.04 (d, 2.4 Hz), 123.31 (s, Ar), 122.92 (s, Ar), 120.25 (s, Ar), 68.01 (d, J$_{CP}$=24.7 Hz, N—CH$_2$—P). Assignment of $^{13}$C{$^1$H} NMR signals was confirmed by $^{13}$C DEPT.

Elemental analysis: Calculated: C, 49.51; H, 3.32. Found: C, 49.36; H, 3.54.

Compound 11:

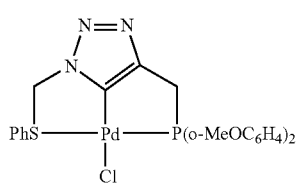

Compound 11

Compound 11 was prepared by complexing palladium to Compound 7.

$^{31}$P{$^1$H} NMR (CDCl$_3$) 24.17 (s).

$^1$H NMR (CDCl$_3$): 7.96-7.24 (m, 15H, Ar), 5.82 (s, 2H, CH$_2$—S), 3.84 (d, J$_{HP}$=11.3 Hz, 2H, CH$_2$—P).

$^{13}$C NMR (CDCl$_3$): 151.35 (d, J$_{CP}$=6.1 Hz C$_{ipso}$), 136.72 (s, Ar), 136.50 (s, Ar), 135.40 (d, J$_{CP}$=3.2 Hz, Ar), 135.01 (s, Ar), 132.76 (s, Ar), 132.34 (s, Ar), 132.10 (s, Ar), 131.61 (s, Ar), 131.40 (s, Ar), 130.33 (s, Ar), 130.11 (s, Ar), 127.04 (d, J$_{CP}$=13.2 Hz), 58.11 (CH$_2$—S), 30.12 (d, J$_{CP}$=33.1 Hz, CH$_2$—P). Assignment of $^{13}$C{$^1$H} NMR signals was confirmed by $^{13}$C DEPT.

Elemental analysis: Calculated: C, 49.83; H, 3.61. Found: C, 50.31; H, 4.09.

Compound 12:

Compound 12 was prepared by complexing palladium to Compound 8.

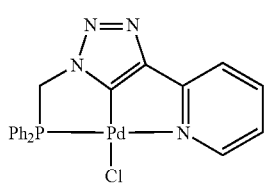

Compound 12

$^{31}$P{$^1$H} NMR (CDCl$_3$) 25.35 (s).

$^1$H NMR (CDCl$_3$): 8.03-6.55 (m, 13H, Ar) 4.86 (s, 2H, CH$_2$—S), 4.51 (d, J$_{HP}$=7.4 Hz, 2H, CH$_2$—P), 3.42 (s, 6H, OCH$_3$). $^{13}$C NMR (CDCl$_3$): 166.25 (s, Ar), 156.51 (bs, C$_{ipso}$), 139.89 (s, Ar), 139.70 (s, Ar), 137.40 (s, Ar), 136.9 (s, Ar), 134.06 (s, Ar), 132.84 (s, Ar), 132.61 (s, Ar), 132.43 (s, Ar), 127.11 (s, Ar), 125.45 (d, J$_{CP}$=9.2 Hz, Ar), 116.05 (d, J$_{CP}$=3.9 Hz, Ar), 59.82 (O—CH$_3$), 57.61 (CH$_2$—S), 28.13 (d, J$_{CP}$=38.3 Hz, CH$_2$—P) (assignment of $^{13}$C{$^1$H} NMR signals was confirmed by $^{13}$C DEPT).

Elemental analysis: Calculated: C, 48.83; H, 3.93. Found: C, 49.51; H, 4.78.

Addition of palladium to Compounds 7 and 8 at room temperature resulted in the appearance of a yellow color. X-ray analysis suggested that bidentate complexes were formed in which the metal is coordinated with the phosphorus atom and with a nitrogen atom in the tetrazole ring, and that the bidentate complexes are converted to the corresponding tridentate complexes (Compounds 11 and 12, respectively) by heating at 70° C.

As shown in Table 1, $^{31}P\{^1H\}$ NMR showed quantitative formation of the complexes as a single product as compared to the corresponding free ligands.

TABLE 1

| Compound (free ligand) | $^{31}$P Shift (ppm) | Compound (palladium complex) | $^{31}$P Shift (ppm) |
|---|---|---|---|
| 5 | −16.7 | 9 | 33.1 (d), 23.4 (d) |
| 6 | −13.4 | 10 | 21.4 (s) |
| 7 | −16.7 | 11 | 24.2 (s) |
| 8 | −33.7 | 12 | 25.4 (s) |

In addition, the preparation of an exemplary platinum pincer complex according to embodiments of the invention was performed as follows.

Preparation of Compound 13: Compound 5 (21 mg; 0.045 mmol), cyclooctadiene(COD)-PtCl$_2$ (17 mg; 0.045 mmol) and triethylamine (10 equivalents) were combined in 2 ml of dimethylformamide. A bright yellow color indicated the formation of the bidentate complex. The resulting solution was heated at 70° C. for 18 hours. The solvent was evaporated and the residue was washed with ether (3×3 ml) and extracted with toluene/tetrahydrofuran. The combined extractions were evaporated, resulting in pure compound 13 in a yield of 100%.

Compound 13

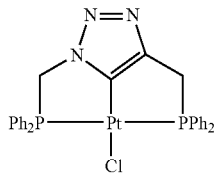

$^{31}P\{^1H\}$ NMR (CD$_2$Cl$_2$) δ: 38.13 (d, J$_{PP}$=445 Hz, J$_{PPt}$=2813 Hz), 28.58 (d, J$_{PP}$=445 Hz, J$_{PPt}$=3084 Hz).

$^1$H NMR (CD$_2$Cl$_2$): 7.96-7.92 (m, 8H, Ar), 7.58-7.51 (m, 12H, Ar), 5.27 (d, J$_{HP}$=7.0 Hz, 2H, P—CH$_2$—N), 3.83 (d, J$_{HP}$=10.5 Hz, 2H, P—CH$_2$—C).

$^{13}C\{^1H\}$ NMR (CD$_2$Cl$_2$): δ: 152.0 (d, C$_{ipso}$), 135.0 (q, J$_{CP}$=12.1 Hz), 133.8, 132.9, 131.2 (d, J$_{CP}$=11.0 Hz), 130.9 (d, J$_{CP}$=10.6 Hz), 54.5 (d, J$_{CP}$=45.2 Hz, P—CH$_2$—N), 32.1 (d, J$_{CP}$=41.2 Hz, P—CH$_2$—C).

Mass spectroscopy (MS ESI): m/z=695.0812 (M+H)$^+$; (C$_{28}$H$_{25}$N$_3$P$_2$ClPt).

Example 5

Structure of Palladium and Platinum Pincer Ligand Complexes

Compound 9 was characterized in solution by multinuclear NMR techniques. As described in Example 4, the $^{31}$P NMR spectrum of Compound 9 was shows two doublets at 33.1 and 23.4 ppm with a typical trans phosphorus-phosphorus coupling constant of 462.0 Hz. In the $^{13}$C NMR spectrum the ipso carbon gives rise to a broad signal centered at 163.0 ppm indicating a formed carbon-metal bond. Similar results were obtained from NMR analysis of Compounds 10-13, as further described in Example 4 hereinabove.

The molecular structure of Compound 9 was confirmed by X-ray analysis. Yellow crystals of Compound 9 suitable for single crystal X-ray analysis were obtained by slow diffusion of diethyl ether to a dichloromethane solution.

As shown in FIG. 5A, the palladium atom is located in the centre of a distorted square planar structure with the chloride group occupying a position trans to the carbon atom of the triazole. The two phosphine groups are located in mutual trans positions with a P—Pd—P angle of 157.02.

CCDC 673968 contains the supplementary crystallographic data. These crystallographic data can be obtained free of charge from the Cambridge Crystallographic Data Centre via www.ccdc.cam.ac.uk/data_request/cif.

The molecular structure of Compound 13, the platinum analog of Compound 9, was similarly characterized by NMR and X-ray analysis.

As described in Example 4, the $^{31}$P NMR spectrum of Compound 13 shows two doublets at 38.13 and 28.58 ppm with a typical trans phosphorus-phosphorus coupling constant of 445 Hz. The $^{195}$Pt—P satellites for both doublets with J$_{PPt}$=2813 and 3084 Hz respectively, clearly indicate coordination of both phosphine arms to the platinum center.

Monoclinic crystals of Compound 13 suitable for X-ray analysis were obtained by slow diffusion of diethyl ether to a dimethylformamide solution.

As shown in FIG. 5B, the platinum atom is located in the centre of a distorted square planar structure with the chloride group occupying a position trans to the carbon atom of the triazole. The two phosphine groups are located in mutual trans positions with a P—Pt—P angle of 159.65.

These results indicate that that the triazole-based pincer ligands are tridentate ligands, as the metal binds not only to the donor groups attached to the triazole, but also to the carbon atom of the triazole.

Example 6

Catalytic Efficiency of Complexes

Facile combinatorial access to a novel family of pincer-ligands and their corresponding metal complexes opens the door to rapid and convenient screening of these systems in various catalytic transformations. With numerous palladium complexes in hand, the ligand influence on catalytic activity in the Heck reaction was examined. The Heck reaction examined is depicted in Scheme 1 hereinbelow.

Scheme 1

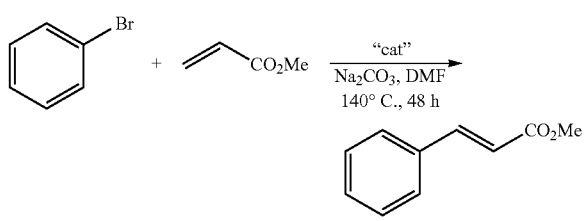

6 mmol of methyl acrylate was added to 5 mmol of bromobenzene in dimethylformamide, followed by the addition of an equimolar amount of sodium carbonate. The catalyst was added in amounts of 3.5×10$^{-5}$ mmol of complex (7×10$^{-4}$ mol %). The resulting mixture was stirred at 140° C. while the reaction progression was followed by gas chromatography. Results of these experiments are presented in Table 2.

TABLE 2

| Compound | Yield [%] | TON (turnover number) |
|---|---|---|
| 9 | 94 | 134,000 |
| 10 | 88 | 125,000 |
| 11 | 29 | 42,000 |
| 12 | 5 | 6,900 |

As shown in Table 2, Compounds 9 and 10 are incredibly efficient catalysts for the Heck reaction. Interestingly, based upon yield and conversion, Compound 9 is among the most active and efficient catalysts for Heck coupling with aryl bromides. Compound 9 mediates the reaction of bromobenzene with methyl acrylate giving a 94% yield and an observed TON (turnover number) of 134,000 after 48 hours.

These results indicate that preparation of pincer type tridentate ligands as described herein is highly advantageous for combinatorial synthesis of non-trivial ligands from relatively simple building blocks.

Example 7

Synthesis of Alkyne Derivatives of Dialkylphosphines

Reaction of lithium dialkyl phosphides with propargyl bromide, in analogy to the procedure described for diarylphosphines in Example 2, resulted in an irresolvable mixture of the desired propargyl phosphine species along with phosphine-allene species (data not shown). Employment of trimethylsilyl(TMS)-protected propargyl bromide also did not afford the desired results (data not shown). Attempts to directly use dialkyl phosphine in reactions with both protected and unprotected propargyl halides led to the formation of tetra-alkyl phosphonium salts via double propargylation of the secondary phosphine (data not shown).

Figure 6:
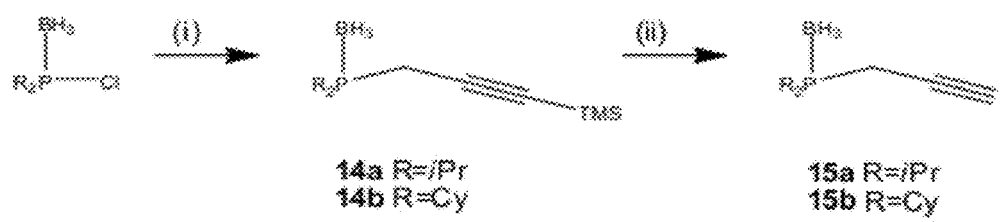
FIG. 6 presents a schematic illustration depicting the syntheses of a dialkyl-containing building block according to some embodiments of the present invention (TMS=trimethylsilyl; iPr=isopropyl; Cy=cyclohexyl)

To avoid the abovementioned obstacles, the following synthesis for the preparation of such compounds was designed and successfully practiced, employing the phosphorus-based species as the electrophile rather than the nucleophile, as depicted in FIG. 6 for exemplary embodiments according to the present invention.

Protection of the alkynyl hydrogen was used in order to prevent the formation of the corresponding allene-substituted phosphines.

General Procedure:

Synthesis of trimethylsilyl (TMS)-protected dicyclohexyl propargylphosphine-borane complex (Compound 14b): 3-(Trimethylsilyl)propargyl magnesium bromide Grignard reagent was prepared according to Hernandez & Soderquist [*Org. Lett.,* 2005, 7, 5397]. To a three-necked 25 ml round bottom flask equipped with a condenser, magnesium turnings (97 mg, 4 mmol), HgCl$_2$ (25 mg) and one crystal of I$_2$ were added. Dry diethyl ether (2 ml) was thereafter added, and the reaction mixture was stirred at room temperature for 1 hour. TMS-propargyl bromide (382 mg, 2 mmol) was then added dropwise, and the obtained solution was refluxed for 30 minutes. The reaction mixture was thereafter cooled at room temperature, and decanted through a cannula under positive pressure of argon to produce a solution of 3-(trimethylsilyl)propargyl magnesium bromide Grignard reagent.

To the prepared Grignard reagent, a solution of dicyclohexyl chlorophosphine-borane complex (Cy$_2$PCl.BH$_3$) (247 mg, 1 mmol) in toluene (1 ml) was added dropwise. The mixture was stirred for 40 hours at room temperature, and was then poured into a solution of NH$_4$Cl (0.56 gram, 10.4 mmol) in water (1.5 ml). The obtained mixture was stirred for 10 minutes and was thereafter extracted with ethyl acetate (2×20 ml). The combined organic extracts were dried over Na$_2$SO$_4$, filtered and concentrated by vacuum. The crude mixture was separated by flash chromatography, using hexane/CH$_2$Cl$_2$ 3:2 as eluent (R$_f$=0.3), to afford TMS-protected dicyclohexyl propargylphosphine-borane complex (Compound 14b) as a colorless oil (0.200 gram, 62% yield).

$^1$H NMR (CDCl$_3$) δ: 0.09 (s, 9H, Si(CH$_3$)$_3$), 1.10-1.55 (m, 10H), 1.60-1.95 (m, 12H), 2.46 (d, 8.9 Hz, 2H, PCH$_2$).

$^{13}$C NMR (CDCl$_3$) δ: 0.1, 12.4 (d, J$_{CP}$=28 Hz, PCH$_2$), 26.2, 26.7, 26.75, 27.0, 27.1, 31.0 (d, J$_{CP}$=31 Hz, CH), 89.1, 98.8.

$^{31}$P NMR (CDCl$_3$) δ: 25.3.

Compound 14b

Using essentially the same procedure as described above, TMS-protected diisopropyl propargylphosphine-borane complex (Compound 14a) was prepared from diisopropyl chlorophosphine-borane complex.

Compound 14a $^1$H NMR (CDCl$_3$) δ: 0.1 (s, 9H), 1.25 (d, 6H), 1.27 (d. 6H), 2.19-2.25 (m, 2H, CH—P), 2.6 (d, J$_{HP}$=9 Hz, 2H).

$^{13}$C NMR (CDCl$_3$) δ: 0.1, 12.5 (d, J$_{CP}$=28 Hz, CH$_2$), 16.8, 21.3 (d, J$_{CP}$=32 Hz, CH), 88.7, 98.2.

$^{31}$P NMR (CDCl$_3$) δ: 33.5 (q, J$_{PB}$=70 Hz).

Removal of TMS protective group: NH$_4$F (185 mg, 5 mmol) was added to a stirred mixture of TMS-protected dicyclohexyl propargylphosphine-borane complex (161 mg, 0.5 mmol) in methanol (1.9 ml). After 16 hours at room temperature, the mixture was concentrated by vacuum. The residue was mixed with water (10 ml) and extracted with ethyl acetate (2×10 ml). The combined organic extracts were dried over Na$_2$SO$_4$, filtered and concentrated by vacuum to give dicyclohexyl propargylphosphine-borane complex (Compound 15b) (0.100 gram, 80% yield) as an off-white solid.

Compound 15b $^1$H NMR (CDCl$_3$) δ: 1.15-1.55 (m, 10H), 1.65-2.00 (m, 12H), 2.07 (dt, J$_{HP}$=3.8 Hz, J$_{HH}$=2.8 Hz, 1H), 2.48 (dd, J$_{HP}$=9.0 Hz, J$_{HH}$=2.8 Hz, 2H, CH$_2$).

$^{13}$C NMR (CDCl$_3$) δ: 11.0 (d, J$_{CP}$=29.6 Hz), 28.9, 26.4 (d, J$_{CP}$=2.5 Hz), 26.6 (d, J$_{CP}$=2.5 Hz), 26.7 (d, J$_{CP}$=2.5 Hz), 26.8 (d, J$_{CP}$=10 Hz), 30.7 (d, J$_{CP}$=30.5 Hz, CH—P), 71.7 (d, J$_{CP}$=4.6 Hz), 76.4 (d, J$_{CP}$=12 Hz).

$^{31}$P NMR (CDCl$_3$) δ: 29.4 (br m).

Using essentially the same procedure as described above, the TMS group was removed from TMS-protected-diisopropyl propargylphosphine-borane complex to obtain diisopropyl propargylphosphine-borane complex (Compound 15a).

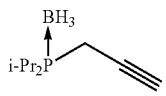

Compound 15a $^1$H NMR (CDCl$_3$) δ: −0.03-0.9 (br m, 3H, BH$_3$), 1.23 (d, 6H, CH$_3$), 1.26 (d, 6H, CH$_3$), 2.1 (q, 1H), 2.2-2.3 (m, 2H, CH—P), 2.6 (dd, J$_{HP}$=9.0 Hz, J$_{HH}$=3.0 Hz).

$^{13}$C NMR (CDCl$_3$) δ: 11.2 (d, J$_{CP}$=28.9 Hz, CH$_2$), 16.9 (d, J$_{CP}$=12.6 Hz, CH$_3$), 21.3 (d, J$_{CP}$=31.4 Hz, CH), 71.7 (d, J$_{CP}$=5.0 Hz, C≡C—H), 76.2 (d, J$_{CP}$=12.6 Hz, C≡C—H).

$^{31}$P NMR (CDCl$_3$) δ: 35.8. The $^{13}$C assignments were confirmed by DEPT (distortionless enhancement by polarization transfer) experiment.

Mass Spectrometry (HRMS ESI): Measured mass (M+H)$^+$ 171.1495 (C$_9$H$_{21}$BP); Calculated mass 171.1474.

Example 8

Synthesis of Azide Derivatives of Dialkylphosphines

Attempts to prepare dialkyl azidomethyl phosphine oxides by procedures analogous to those described in Example 1 for preparing aryl-substituted analogs did not furnish satisfactory results (data not shown).

Hence, a novel synthetic route was designed and successfully practiced. The novel synthesis involves the preparation of dialkyl azidomethyl phosphine oxide azide 20 from the corresponding bromide 19, which can be obtained, in turn, from the corresponding carboxylic acid 18, as generally depicted in FIG. 7A for the retrosynthesis and is further depicted in more detail in FIG. 7B for exemplary embodiments according to the present invention.

Synthesis of dialkylphosphinyl acetate ester (general procedure): To benzyl (or t-butyl) bromoacetate (15 mmol) was added the corresponding dialkyl chlorophosphine (10 mmol). After stirring the neat mixture for 10 minutes at room temperature, the mixture was kept for 3 days without stirring. A viscous mixture was obtained, which was dissolved in 10 ml CHCl$_3$. This solution was removed from inert atmosphere, and added dropwise to a stirred mixture of NaHCO$_3$ (40 mmol). The organic layer was separated and the aqueous phase was extracted with CHCl$_3$ (2×10 ml). The combined organic layers were washed with saturated NaHCO$_3$, dried over Na$_2$SO$_4$, filtered and concentrated under vacuum. The crude mixture was separated by flash chromatography, using ethyl acetate:methanol 90:10 as eluent, to give the ester in more than 90% yield.

Using this procedure, the following benzyl esters and t-butyl esters of dialkylphosphinyl acetates were prepared.

Benzyl dicyclohexylphosphinyl acetate (Compound 16b):

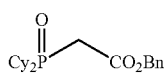

Compound 16b $^1$H NMR (CDCl$_3$) δ: 1.05-1.46 (m, 10H, Cy), 1.51-1.90 (m, 12H, Cy), 2.83 (d, 14.7 Hz, 2H, P—CH$_2$), 5.06 (s, 2H, CH$_2$—C$_6$H$_5$), 7.23-7.33 (m, Ph).

$^{13}$C NMR: 24.4 (d, J$_{CP}$=2.1 Hz, CH$_2$), 24.8 (d, J$_{CP}$=2.6 Hz, CH$_2$), 25.3, 25.8 (d, J$_{CP}$=2.6 Hz, CH$_2$), 26.0 (d, J$_{CP}$=2.1 Hz, CH$_2$), 31.6 (d, J$_{CP}$=47 Hz, P—CH$_2$), 35.6 (d, J$_{CP}$=65 Hz, CH), 66.8 (CH$_2$), 128.1, 128.2, 128.4, 134.7, 166.5.

$^{31}$P NMR (CDCl$_3$) δ: 60.0.

HRMS ESI (M+H)$^-$ 363.2080 (C$_{21}$H$_{32}$O$_3$P); Calculated mass 363.2089

Benzyl diisopropylphosphinyl acetate (Compound 16a):

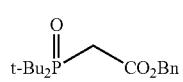

Compound 16a $^1$H NMR (CDCl$_3$) δ: 1.01 (d, 3H), 1.06 (d, 3H), 1.07 (d, 3H), 1.12 (d, 3H), 1.98 (m, 2H, CH), 2.83 (d, J$_{HP}$=14.7 Hz, 2H, P—CH$_2$), 5.02 (s, 2H), 7.18-7.26 (m, 5H)

$^{31}$P NMR (CDCl$_3$) δ: 55.7.

HRMS ESI (M+H)$^-$ 283.1447 (C$_{15}$H$_{24}$O$_3$P); Calculated mass 283.1463.

Benzyl di(t-butyl)phosphinyl acetate (Compound 16c):

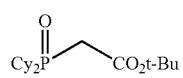

Compound 16c $^1$H NMR (CDCl$_3$) δ: 1.26 (d, J$_{HP}$=14.1 Hz, 18H, C(CH$_3$)$_3$), 2.93 (d, J$_{HP}$=11.3 Hz, 2H, P—CH$_2$), 5.15 (s, 2H), 7.25-7.40 (m, 5H).

$^{13}$C NMR (CDCl$_3$) δ: 26.3, 30.6 (d, J$_{CP}$=41 Hz, P–CH$_2$), 36.4 (d, J$_{CP}$=60 Hz, P(O)C$^{t\text{-}Bu}$), 66.9, 127.9, 128.2, 135.2, 167.3.

$^{31}$P NMR (CDCl$_3$) δ: 56.8.

HRMS ESI (M+H)$^-$ 311.1731 (C$_{17}$H$_{28}$O$_3$P); Calculated mass 311.1776 t-Butyl dicyclohexylphosphinyl acetate (Compound 17b):

Compound 17b

Cy$_2$P—CO$_2$t-Bu $^1$H NMR (CDCl$_3$) δ: 1.16-1.32 (m, 6H, Cy), 1.36-1.55 (m, 4H, Cy), 1.43 (s, 9H, t-Bu), 1.69 (m, 2H, Cy), 1.76-2.00 (m, 10H, Cy), 2.81 (d, J$_{HP}$=15.5 Hz, 2H, P—CH$_2$).

$^{13}$C NMR (CDCl$_3$) δ: 24.8 (d, J$_{CP}$=3.5 Hz, CH$_2$), 25.2 (d, J$_{CP}$=3.2 Hz, CH$_2$), 25.8 (d, J$_{CP}$=1.4 Hz, CH$_2$), 26.3 (d, J$_{CP}$=3.5 Hz, CH$_2$), 26.4 (d, J$_{CP}$=3.9 Hz, CH$_2$), 27.9, 33.4 (d, J$_{CP}$=48 Hz, P—CH$_2$), 36.0 (d, J$_{CP}$=65 Hz, CH), 81.9, 166.2.

$^{31}$P NMR (CDCl$_3$) δ: 50.6.

HRMS ESI (M+H)$^-$ 329.2227 (C$_{18}$H$_{34}$O$_3$P); Calculated mass 329.2246.

t-Butyl diisopropylphosphinyl acetate (Compound 17a):

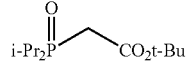

Compound 17a $^1$H NMR (500 MHz, CDCl$_3$) δ: 1.16 (d, J=7.0 Hz, 3H), 1.19 (m, 6H, 2 Me), 1.22 (d, 7.2 Hz, 3H, Me), 1.39 (s, 9H, t-Bu), 2.10 (m, 2H), 2.80 (d, J$_{HP}$=15.2 Hz, 2H, P—CH$_2$).

$^{13}$C NMR (CDCl$_3$) δ: 15.0, 15.6, 25.9 (d, J$_{CP}$=64 Hz, CH), 27.7, 33.2 (d, J$_{CP}$=46 Hz, P—CH$_2$), 81.9, 166.0.

$^{31}$P NMR (CDCl$_3$) δ: 53.2.

HRMS ESI (M+H)$^-$ 249.1610 (C$_{12}$H$_{26}$O$_3$P); Calculated mass 249.1620.

Synthesis of diisopropylphosphinyl acetic acid (reduction of Bn) (Compound 18a): Benzyl diisopropylphosphinyl acetate (Compound 16a, 2.61 grams, 9.2 mmol) was dissolved in absolute ethanol (25 ml) in a 100 ml Fischer Porter hydrogenator. This mixture was hydrogenated over 10% palladium charcoal (0.26 gram) under H$_2$ at a pressure of 4.5 bar. After 18 hours, the reaction mixture was filtered and concentrated under vacuum to yield diisopropylphosphinyl acetic acid (Compound 18a) (1.77 grams, 100% yield) as a white powder.

Compound 18a

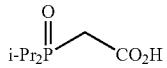

$^1$H NMR (CDCl$_3$) δ: 0.96 (d, J=7.2 Hz, 3H, Me), 0.98 (d, 3H, Me), 0.99 (d, 3H, Me), 1.02 (d, J=7.2 Hz, 3H, Me), 2.05 (m, 2H), 2.73 (d, J$_{HP}$=16.0 Hz, 2H, P—CH$_2$), 11.8 (bs, H, CO$_2$H).

$^{13}$C NMR (CDCl$_3$) δ: 14.3 (d, J$_{CP}$=2.8 Hz, 2Me), 14.9 (d, J$_{CP}$=2.8 Hz, 2Me), 24.8 (d, J$_{CP}$=65 Hz, CH), 30.8 (d, J$_{CP}$=51 Hz, P—CH$_2$), 167.4.

$^{31}$P NMR (CDCl$_3$) δ: 62.3.

HRMS ESI (M+H)$^-$ 193.0986 (C$_8$H$_{18}$O$_3$P); Calculated mass 193.0994.

Using essentially the same procedure, dicyclohexylphosphinyl acetic acid and di(t-butyl)phosphinyl acetic acid were obtained from the corresponding benzyl esters.

Dicyclohexylphosphinyl acetic acid (Compound 18b):

Compound 18b

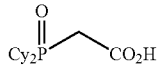

$^1$H NMR (CDCl$_3$) δ: 1.07-1.47 (m, 10H, Cy), 1.58-2.02 (m, 12H, Cy), 2.87 (d, J$_{HP}$=15.6 Hz, 2H, P—CH$_2$), 11.90 (bs, H, CO$_2$H).

$^{13}$C NMR (CDCl$_3$) δ: 24.4 (d, J$_{CP}$=2.1 Hz, CH$_2$), 24.9 (d, J$_{CP}$=2.6 Hz, CH$_2$), 25.5 (CH$_2$), 26.0 (d, J$_{CP}$=5.7 Hz, CH$_2$), 26.2 (d, J$_{CP}$=6.0 Hz, CH$_2$), 31.2 (d, J$_{CP}$=50 Hz, P—CH$_2$), 35.1 (d, J$_{CP}$=65 Hz, CH), 168.0.

$^{31}$P NMR (CDCl$_3$) δ: 56.1.

HRMS ESI (M+H)$^-$ 273.1608 (C$_{14}$H$_{26}$O$_3$P); Calculated mass 273.1620.

Di(t-butyl)phosphinyl acetic acid (Compound 18c):

Compound 18c

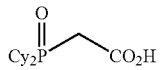

$^1$H NMR (CDCl$_3$) δ: 1.14 (d, J$_{HP}$=14.3 Hz, 18H), 2.71 (d, J$_{HP}$=10.0 Hz, P—CH$_2$), 12.0 (bs, 1H, COOH).

$^{13}$C NMR (CDCl$_3$) δ: 25.7, 28.2 (d, J$_{CP}$=45 Hz, P—CH$_2$), 35.9 (d, J$_{CP}$=59 Hz, P(O)C$^{t\text{-}Bu}$), 167.7.

$^{31}$P NMR (CDCl$_3$) δ: 61.6.

HRMS ESI (M+H) 221.1292 (C$_{10}$H$_{22}$O$_3$P); Calculated mass 221.1307

Synthesis of diisoprpyl bromomethyl phosphine oxide (Compound 19a): Mercuric oxide (1.30 grams, 6.0 mmol), MgSO$_4$ (1.46 grams, 12 mmol), and diisopropylphosphinyl acetic acid (i-Pr$_2$P(O)CH$_2$COOH) (Compound 18a, 1.15 grams, 6 mmol) were combined in anhydrous CH$_2$Cl$_2$ (15 ml) without exclusion of air. A solution of Br$_2$ (1.92 grams, 12 mmol) in CH$_2$Cl$_2$ (15 ml) was added dropwise to the stirred mixture. After 18 hours at room temperature, saturated NaHSO$_3$ (0.5 ml in H$_2$O) was added to the stirred mixture, and the organic solvent was decanted. The solids were triturated with CH$_2$Cl$_2$ (25 ml), and the combined organic layers were stirred with saturated NaHCO$_3$ until evolution of CO$_2$ ceased entirely. The phases were separated, and the organic layer was dried over Na$_2$SO$_4$, filtered and concentrated under vacuum. The crude mixture was separated by flash chromatography on activated alumina, using ethyl acetate:methanol 90:10 as eluent, to give diisopropyl bromomethyl phosphine oxide (Compound 19a) (368 mg, 27% yield) as a colorless oil.

Compound 19a

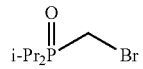

$^1$H NMR (CDCl$_3$) δ: 1.21 (d, J=7.2 Hz, 3H, Me), 1.22 (d, J=7.2 Hz, 3H, Me), 1.26 (d, J=7.3 Hz, 3H, Me), 1.27 (d, J=7.2 Hz, 3H, Me), 2.30 (m, J=2H, CH), 3.36 (d, J$_{HP}$=7.3 Hz, 2H, P—CH$_2$).

$^{13}$C NMR (CDCl$_3$) δ: 15.3 (d, J$_{CP}$=2.8 Hz, Me), 16.0 (d, J$_{CP}$=3.2 Hz, Me), 16.5 (d, J$_{CP}$=56 Hz, P—CH$_2$), 24.4 (d, J$_{CP}$=66 Hz, CH).

$^{31}$P NMR (CDCl$_3$) δ: 55.1.

HRMS ESI (M+H)$^-$ 227.0189 (C$_7$H$_{17}$OPBr); Calculated mass 227.0200.

Using essentially the same procedure, dicyclohexyl bromomethyl phosphine oxide and di-t-butyl bromomethyl phosphine oxide were prepared from the corresponding dialkylphosphinyl acetic acids.

Dicyclohexyl bromomethyl phosphine oxide (Compound 19b):

Compound 19b

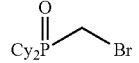

$^1$H NMR (CDCl$_3$) δ: 1.06-2.00 (m, 22H, Cy), 3.19 (d, J$_{HP}$=7.0 Hz, 2H, P—CH$_2$);

$^{13}$C NMR (CDCl$_3$) δ: 16.8 (d, J$_{CP}$=54 Hz, P—CH$_2$), 24.9 (d, 3.2 Hz, CH$_2$), 25.3 (d, J$_{CP}$=3.7 Hz, CH$_2$), 25.5 (dt, J$_{CP}$=1.1 Hz, CH$_2$), 26.0 (CH$_2$), 26.1 (CH$_2$), 26.3 (CH$_2$), 34.4 (d, J$_{CP}$=66 Hz, CH).

$^{31}$P NMR (CDCl$_3$) δ: 49.2.

HRMS ESI (M+H)$^-$ 307.0792 (C$_{13}$H$_{25}$BrOP); Calculated mass 307.0826

Di-t-butyl bromomethyl phosphine oxide (Compound 19c):

Compound 19c

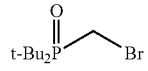

$^1$H NMR (CDCl$_3$) δ: 1.31 (d, J$_{HP}$=13.6 Hz, 18H), 3.36 (d, J$_{HP}$=5.5 Hz, 2H, P—CH$_2$).

$^{13}$C NMR (CDCl$_3$) δ: 16.8 (d, $J_{CP}$=46 Hz, P—CH$_2$), 26.9 (Me), 36.4 (d, $J_{CP}$=59 Hz, P—C$^{t\text{-}Bu}$).

$^{31}$P NMR (CDCl$_3$) δ: 52.3.

HRMS ESI (M+H)$^-$ 255.0499 (C$_9$H$_{21}$BrOP); Calculated mass 255.0513

Synthesis of diisopropyl azidomethyl phosphine oxide (Compound 20a): NaN$_3$ (330 mg, 5 mmol) was added to a solution of diisopropyl bromomethyl phosphine oxide (Compound 19a, 570 mg, 2.5 mmol) in dimethyl sulfoxide (DMSO) (6 ml). The reaction mixture was heated to 90° C. under argon. After 8 hours, the mixture was cooled, treated with water (12 ml) and extracted with CHCl$_3$ (3×6 ml). The combined extracts were washed with water, dried over Na$_2$SO$_4$, filtered, and concentrated by vacuum to give diisopropyl azidomethyl phosphine oxide (Compound 20a) (470 mg, 100% yield) which was used without further purification.

Compound 20a

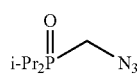

$^1$H NMR (CDCl$_3$) δ: 1.15 (d, J=7.2 Hz, 3H, Me), 1.19 (d, J=7.2 Hz, 3H, Me), 1.20 (d, J=7.2 Hz, 3H, Me), 1.24 (d, J=7.3 Hz, 3H, Me), 2.08 (m, 2H, CH), 3.59 (d, $J_{HP}$=7.9 Hz, 2H, P—CH$_2$).

$^{13}$C NMR (CDCl$_3$) δ: 15.1 (d, $J_{CP}$=3.2 Hz, 2Me), 15.6 (d, $J_{CP}$=2.6 Hz, 2Me), 24.5 (d, $J_{CP}$=64 Hz, CH), 43.9 (d, $J_{CP}$=65 Hz, P—CH$_2$).

$^{31}$P NMR (CDCl$_3$) δ: 56.1.

HRMS ESI (M+H)$^-$ 190.1078 (C$_7$H$_{17}$N$_3$OP); Calculated mass 190.1109.

Using essentially the same procedure, dicyclohexyl azidomethyl phosphine oxide and di-t-butyl azidomethyl phosphine oxide were prepared from the corresponding dialkyl bromomethyl phosphine oxides.

Dicyclohexyl azidomethyl phosphine oxide (Compound 20b):

Compound 20b

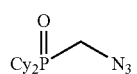

$^1$H NMR (CDCl$_3$) δ: 1.07-1.42 (m, 10H, Cy), 1.56-1.90 (m, 12H, Cy), 3.47 (d, $J_{HP}$=7.7 Hz, 2H, P—CH$_2$).

$^{13}$C NMR (CDCl$_3$) δ: 24.6 (d, $J_{CP}$=3.5 Hz, CH$_2$), 25.1 (d, $J_{CP}$=2.8 Hz, CH$_2$), 25.5 (d, $J_{CP}$=1.1 Hz, CH$_2$), 26.0 (d, $J_{CP}$=4.6 Hz, CH$_2$), 26.2 (d, $J_{CP}$=4.6 Hz, CH$_2$), 34.4 (d, $J_{CP}$=64 Hz, CH), 43.7 (d, $J_{CP}$=64 Hz, P—CH$_2$).

$^{31}$P NMR (CDCl$_3$) δ: 51.1.

HRMS ESI (M+H)$^-$ 270.1733 (C$_{13}$H$_{25}$N$_3$OP); Calculated mass 270.1735

Di-t-butyl azidomethyl phosphine oxide (Compound 20c):

Compound 20c

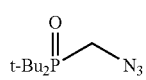

$^1$H NMR (CDCl$_3$) δ: 1.28 (d, $J_{HP}$=13.8 Hz, 18H), 3.63 (d, $J_{HP}$=6.2 Hz, 2H, P—CH$_2$).

$^{13}$C NMR (CDCl$_3$) δ: 26.5 (Me), 35.5 (d, $J_{CP}$=59 Hz, P—C$^{t\text{-}Bu}$), 43.9 (d, $J_{CP}$=59 Hz, P—CH$_2$).

$^{31}$P NMR (CDCl$_3$) δ: 55.7.

HRMS ESI (M+H)$^-$ 218.1405 (C$_9$H$_{21}$N$_3$OP); Calculated mass 218.1422.

Example 9

Alternative Synthesis of Azide Derivatives of Dialkylphosphines

As an alternative to part of the procedures described in Example 8, a dialkyl bromomethyl phosphine oxide was prepared from t-butyl dialkylphosphinyl acetate as depicted in FIG. 8, for exemplary embodiments of the present invention, and is described in detail below. Preparation of the t-butyl dialkylphosphinyl acetate, as well as conversion of the dialkyl bromomethyl phosphine oxide to the dialkyl azidomethyl phosphine oxide product, was performed as described in Example 8.

Synthesis of t-butyl diisopropylphosphinyl bromoacetate (Compound 21a): t-Butyl diisopropylphosphinyl acetate (Compound 17a) was prepared as described in Example 8.

A solution of 50% aqueous NaOH (2.40 grams) mixed with water (2.4 ml) was cooled to 0-5° C. in a water/ice bath. Br$_2$ (2.16 grams, 13.5 mmol) was added dropwise to the stirred solution at a rate which maintained the reaction mixture below 10° C. A solution of t-butyl diisopropylphosphinyl acetate (Compound 17a, 0.67 gram, 1.75 mmol) in 1,4-dioxane (4.5 ml) was added dropwise to the stirred solution while maintaining the reaction temperature below 10° C. After stirring for 30 minutes, the reaction mixture was extracted with diethyl ether (4×5 ml). The combined organic extracts were dried over Na$_2$SO$_4$, filtered and concentrated under vacuum to afford t-butyl diisopropylphosphinyl dibromoacetate (1.10 gram, 95% yield) as a colorless viscous oil. The dibromide was essentially pure as determined by TLC and NMR analysis and was used in the following step without further purification.

To a solution of t-butyl diisopropylphosphinyl dibromoacetate (0.71 gram, 2.17 mmol) in methanol (4 ml) at 0° C. was added a cooled solution of tin(II) chloride dihydrate (0.39 gram, 1.73 mmol) and acetic acid (0.21 gram) in methanol (4 ml). After stirring for 30 minutes at 0-5° C., the reaction mixture was diluted with water (16 ml) and extracted with CHCl$_3$ (3×10 ml). The combined extracts were washed with water, dried over Na$_2$SO$_4$, filtered and concentrated by vacuum at 50° C. The crude mixture was separated by flash chromatography, using ethyl acetate/methanol 90:10 as eluent, to give t-butyl diisopropylphosphinyl bromoacetate (Compound 21a) (0.42 gram, 63% yield) as a colorless oil.

Compound 21a

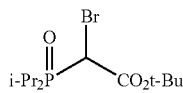

$^1$H NMR (CDCl$_3$) δ: 0.97-1.10 (m, 12H, Me), 1.24 (s, 9H, t-Bu), 2.24 (m, 2H, CH$^{i\text{-}Pr}$), 4.21 (d, $J_{HP}$=10.0 Hz, H, P—CHBr).

$^{13}$C NMR (CDCl$_3$) δ: 15.4 (d, $J_{CP}$=2.8 Hz, Me), 15.8 (d, $J_{CP}$=3.5 Hz, Me), 15.9 (d, $J_{CP}$=3.5 Hz, Me), 16.2 (d, $J_{CP}$=2.8 Hz, Me), 24.9 (d, $J_{CP}$=65 Hz, CH$^{i\text{-}Pr}$), 25.0 (d, $J_{CP}$=65 Hz, CH$^{i\text{-}Pr}$), 27.2 (Me$^{t\text{-}Bu}$), 38.3 (d, $J_{CP}$=39 Hz, P—CHBr), 83.7) (C$^{t\text{-}Bu}$), 164.2.

$^{31}$P NMR (CDCl$_3$) δ: 54.5.

Mass spectroscopy (HRMS ESI): Measured mass (M+H)$^+$ 327.0724 (C$_{12}$H$_{25}$O$_3$PBr); Calculated mass 327.0725.

Using essentially the same procedure, t-butyl dicyclohexylphosphinyl bromoacetate (Compound 21b) was prepared from t-butyl dicyclohexylphosphinyl acetate (Compound 17b, prepared as described in Example 8).

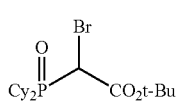

Compound 21b $^1$H NMR (CDCl$_3$) δ: 1.07-1.24 (m, 6H, Cy), 1.32-1.47 (m, 4H, Cy), 1.38 (s, 9H, t-Bu), 1.61 (m, 2H, Cy), 1.66-2.24 (m, 10H, Cy), 4.33 (d, J$_{HP}$=9.4 Hz, 1H, P—CHBr).

$^{13}$C NMR (CDCl$_3$) δ: 25.9 (CH$_2$), 27.5 (Me), 35.4 (d, J$_{CP}$=64.3 Hz, CH$^{Cy}$), 35.5 (d, J$_{CP}$=64.3 Hz, CH$^{Cy}$), 38.8 (d, J$_{CP}$=37.8 Hz, P—CHBr), 83.9 (C$^{t-Bu}$), 164.6.

$^{31}$P NMR (CDCl$_3$) δ: 49.4.

Mass spectroscopy (HRMS ESI): Measured mass (M+H)$^+$ 407.1358 (C$_{18}$H$_{33}$BrO$_3$P); Calculated mass 407.1351.

Synthesis of diisopropylphosphinyl bromoacetic acid Compound 22a): Trifluoroacetic acid (1.2 ml, 16.2 mmol) was added dropwise to a solution of t-butyl diisopropylphosphinyl bromoacetate (Compound 21a, 0.40 gram, 1.22 mmol) in CHCl$_3$ (1.2 ml), and the mixture was stirred at room temperature for 16 hours. The mixture was thereafter concentrated under vacuum to afford crude diisopropylphosphinyl bromoacetic acid (Compound 22a) (0.33 gram, 100% yield). This material was used in the following step without further purification.

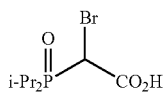

Compound 22a $^1$H NMR (CDCl$_3$) δ: 1.18-1.29 (m, 12H, Me), 2.56 (m, 2H, 2CH$^{i-Pr}$), 4.71 (d, J$_{HP}$=11.1 Hz, 1H, P—CHBr), 12.9 (s, 1H, CO$_2$H).

$^{13}$C NMR (CDCl$_3$) δ: 15.5 (d, J$_{CP}$=2.5 Hz, Me), 15.8 (d, J$_{CP}$=3.5 Hz, Me), 15.9 (d, J$_{CP}$=3.2 Hz, Me), 16.0 (d, J$_{CP}$=2.8 Hz, Me), 25.1 (d, J$_{CP}$=63 Hz, CH$^{i-Pr}$), 25.3 (d, J$_{CP}$=64 Hz, CH$^{i-Pr}$), 37.1 (d, J$_{CP}$=42 Hz, P—CHBr), 166.3.

$^{31}$P NMR (CDCl$_3$) δ: 60.6.

Mass spectroscopy (HRMS ESI): Measured mass (M+H)$^+$ 271.0091 (C$_8$H$_{17}$O$_3$PBr); Calculated. mass 271.0099.

Using essentially the same procedure, dicyclohexylphosphinyl bromoacetic acid (Compound 22b) was prepared from the corresponding t-butyl ester (Compound 21b).

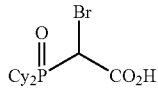

Compound 22b $^1$H NMR (CDCl$_3$) δ: 1.17-2.03 (m, 2H, Cy), 2.21-2.45 (m, 2H), 4.71 (d, J$_{HP}$=11.1 Hz, 1H, P—CHBr—).

$^{13}$C NMR (CDCl$_3$) δ: 25.3-25.7, 26.0-26.4, 34.9 (d, J$_{CP}$=63.0 Hz, CH$^{Cy}$), 35.2 (d, J$_{CP}$=63.0 Hz, CH$^{Cy}$), 36.7 (d, J$_{CP}$=41.9 Hz, P—CHBr), 166.1.

$^{31}$P NMR (CDCl$_3$) δ: 57.

Mass spectroscopy (HRMS ESI): Measured mass (M+H)$^+$ 351.0717 (C$_{14}$H$_{25}$BrO$_3$P); Calculated. mass 351.0725.

Synthesis of diisopropyl bromomethyl phosphine oxide (decarboxylation) (Compound 19a): Diisopropylphosphinyl bromoacetic acid (Compound 22a, 0.33 gram, 1.22 mmol) was charged in a 25 ml round bottom flask equipped with a magnet stirrer and condenser. The flask was heated to 160-165° C. for 30 minutes under a vacuum (6 mmHg). The crude residue was separated by flash chromatography, using ethyl acetate/methanol 90:10 as eluent, to give diisopropyl bromomethyl phosphine oxide (Compound 19a) (0.19 gram, 69% yield) as a colorless oil.

Example 10

Preparation of Pincer Ligands Comprising a Dialkyl Phosphinyl Moiety

The new phosphine-containing compounds such as described in Examples 7-9 hereinabove can be utilized in a variety of synthetic applications. Of these, their applicability to the selective combinatorial synthesis of tridentate ligands is demonstrated herein. In the interest of expanding this library to include bulky, electron-donating substituents, a number of dialkyl phosphine-containing compounds, and azidomethyl sulfide 2, were used in the Huisgen dipolar cycloaddition described in Example 3 (the click reaction).

Precursors comprising an azidomethyl group (azide derivatives), such as described in Examples 8 and 9, were reacted with precursors comprising a propargyl group (alkyne derivatives), such as those described in Example 7, resulting in the formation of 1,4-substituted triazole pincer ligands having one or two protected dialkyl phosphinyl moieties, as depicted in FIG. 9, for exemplary embodiments of the present invention.

It was found that [2+3] cycloaddition utilizing the dialkyl phosphine-containing compounds described herein proceeds smoothly even with phosphine species bearing bulky i-propyl and cyclohexyl substituents. The synthesis of a number of representative ligands, including symmetrically and non-symmetrically substituted PCP and PCS species, is shown in FIG. 9.

After Cu(I)-catalyzed cycloaddition and concomitant phosphine deprotection, novel alkyl-substituted electron-donating phosphine-based pincer click ligands were prepared.

Preparation of Protected Forms of Pincer Ligands:

Dialkyl phosphine donor groups in the pincer ligand were obtained by using precursors comprising a protected form (phosphine oxide or phosphine-borane complex) of the dialkyl phosphine group.

As an example, the synthesis of the protected form of the pincer ligand having a diisopropyl phosphine oxide moiety and a diisopropyl phosphine-borane complex (protected form of Compound 27) was performed as follows.

Synthesis of protected form of Compound 27: The azide precursor Compound 19a (350 mg, 1.85 mmol) was added to the alkyne precursor Compound 15a (315 mg, 1.85 mmol) in 3 ml THF. In a separate vessel, CuSO$_4$.5H$_2$O (230 mg, 0.925 mmol) was dissolved in 3 ml distilled water. Upon addition of sodium ascorbate (916 mg, 4.62 mmol) to the aqueous mixture, the resulting dark brown mixture was quickly added to the reaction. The reaction mixture was stirred at room temperature for 48 hours under nitrogen. The aqueous phase was extracted with CH$_2$Cl$_2$ (3×10 ml) and the combined organic layers were washed with water (20 ml) and brine (20 ml). The organic phase was dried with anhydrous Na$_2$SO$_4$. The obtained crude mixture was separated by flash chromatography, using 90:10 CH$_2$Cl$_2$:MeOH as eluent, to give the protected form of Compound 27 as a white solid (yield was 76%).

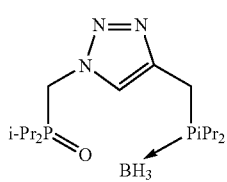

Protected form of Compound 27

$^1$H NMR (CDCl$_3$) δ:1.11-1.23 (m, 24H, CH$_3$), 2.01-2.10 (m, 4H, CH), 3.13 (d, J$_{HP}$=10.2 Hz, 2H, P—CH$_2$—C), 4.77 (d, J$_{HP}$=6.3 Hz, 2H, P—CH$_2$—N), 7.84 (s, 1H, triazole-H).

$^{13}$C NMR (CDCl$_3$) δ: 15.3 (d, J$_{CP}$=22.5 Hz), 16.9, 17.9 (d, J$_{CP}$=30 Hz), 21.7 (d, J$_{CP}$=37.5 Hz), 25.1 (d, J$_{CP}$=67.5 Hz), 44.6 (d, J$_{CP}$=60 Hz), 124.6, 147.

$^{31}$P NMR (CDCl$_3$) δ: 35.6 (d, 1P), 53.8 (s, 1P).

Mass spectroscopy (HRMS ESI): Measured mass (M+H)$^+$ 360.2492 (C$_{16}$H$_{37}$BN$_3$OP$_2$); Calculated mass 360.2505.

Using essentially the same procedure, the following protected forms of pincer ligands were also obtained:

Synthesis of protected form of Compound 28: The azide precursor Compound 19b was reacted with the alkyne precursor Compound 15a according to the above-described procedure to obtain the following compound (yield: 69%):

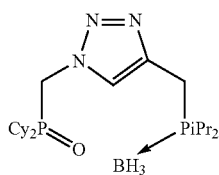

Protected form of Compound 28

$^1$H NMR (CDCl$_3$) δ: 1.04-1.19 (m, 22H), 1.61-1.79 (m, 14H), 1.94-2.06 (m, 2H, CH$^{iPr}$), 3.03 (d, J$_{HP}$=10.5 Hz, P—CH$_2$—C), 4.71 (d, J$_{HP}$=6.3 Hz, P—CH$_2$—N), 7.74 (s, 1H, triazole-H).

$^{13}$C NMR (CDCl$_3$) δ: 15.3 (d, J$_{CP}$=22.5 Hz), 17.7 (d, J$_{CP}$=30 Hz, CH$_2$), 24.6, 25.4, 25.8, 26.4 (CH$_2$), 26.6 (CH$_2$), 26.7 (CH$_2$), 31.4 (d, J$_{CP}$=30.8 Hz), 44.6 (d, J$_{CP}$=60 Hz, CH$_2$, 124.5, 140.8.

$^{31}$P NMR (CDCl$_3$) δ: 27.6 (m, 1P), 53.9 (s, 1P). The $^{13}$C assignments were confirmed by DEPT.

Mass spectroscopy (HRMS ESI): Measured mass (M+H)$^+$ 440.3105 (C$_{22}$H$_{45}$BN$_3$OP$_2$); Calculated mass 440.3131.

Synthesis of protected form of Compound 29: The azide precursor Compound 2 was reacted with the alkyne precursor Compound 15a according to the above-described procedures to obtain the following compound (yield: 85%):

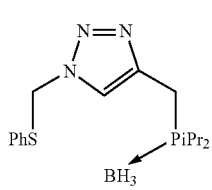

Protected form of Compound 29

$^1$H NMR (200 MHz, CDCl$_3$) δ: 1.44-1.58 (m, 12H), 2.20-2.39 (m, 2H), 3.76 (d, J$_{HP}$=11.4 Hz, CH$_2$—P), 5.44 (s, 2H, CH$_2$—S), 7.58-7.81 (m, 5H), 8.46 (s, 1H, triazole-H).

$^{13}$C NMR (CDCl$_3$) δ: 16.1 (d, J$_{CP}$=30 Hz, CH$_2$—P), 16.7 (d, J$_{CP}$=7.5 Hz), 22.4 (d, J$_{CP}$=30 Hz), 55.2 (CH$_2$—S), 125.3, 129.1, 131.1, 132.4, 139.4.

$^{31}$P NMR (CDCl$_3$) δ: 38.6 (br m).

Synthesis of protected form of Compound 30: The azide precursor Compound 2 was reacted with the alkyne precursor Compound 15b according to the above-described procedures to obtain the following compound (yield: 79%):

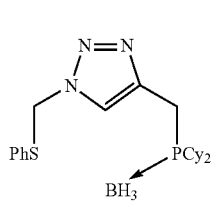

Protected form of Compound 30

$^1$H NMR (CDCl$_3$) δ: 0.2-0.7 (br m, 3H, BH$_3$), 1.17-1.24 (m, 10H), 1.68-1.83 (m, 12H), 3.08 (d, J$_{HP}$=6.6 Hz, 2H, P—CH$_2$), 5.59 (s, 2H, S—CH$_2$), 7.65 (s, 1H, triazole-H).

$^{13}$C NMR (CDCl$_3$) δ: 17.9 (d, J$_{CP}$=15 Hz, CH$_2$—P), 25.8, 26.4, 26.5, 26.6, 26.7, 26.8, 31.4 (d, J$_{CP}$=11.3 Hz, CH—P), 53.8 (CH$_2$—S), 122.4, 128.6, 129.4, 131.6, 132.2, 140.6. The $^{13}$C assignments were confirmed by DEPT.

$^{31}$P NMR (CDCl$_3$) δ: 24.5 (d).

Deprotection of Phosphine Groups of Pincer Ligands:

Deprotection of Compound 27: The phosphine oxide group of the protected form of Compound 27 was reduced as follows:

The protected form of Compound 27 (285 mg, 0.79 mmol) was dissolved in 2 ml CH$_2$Cl$_2$ and 5 ml toluene. To this solution phenylsilane (1.47 ml, 11.9 mmol) was added. The reaction mixture was then heated to 90° C. in a closed vessel. After 18 hours, borane-dimethylsulfide complex was added, and the mixture was concentrated in vacuum. The crude mixture was separated by flash chromatography, using 100:0 to 80:20 hexane:ethyl acetate as gradient eluent, to afford 167 mg of the borane-protected ligand as a white powder.

The borane-protected pincer ligand was then deprotected as follows:

The ligand was redissolved in methanol (2 ml) and dioxane (6 ml) and was heated to 90° C. in a closed vessel over powdered 4 Å molecular sieves. After 18 hours the reaction mixture was cooled, decanted, and evaporated to give 150 mg (60% yield) of Compound 27 as a clear oil.

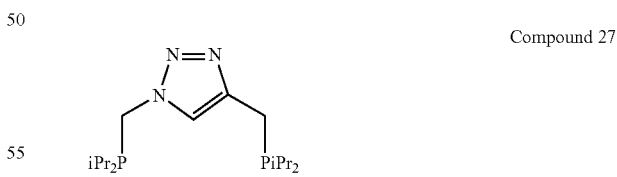

Compound 27

$^1$H NMR (CD$_3$OD) δ: 0.96-1.05 (m, 24H), 1.68-1.78 (m, 2H), 1.79-1.84 (m, 2H), 2.78 (s, 2H), 4.60 (d, J$_{HP}$=6.9 Hz, 2H), 7.69 (s, 1H, triazole-H).

$^{13}$C NMR (CD$_3$OD) δ: 19.1, 19.2, 19.3, 19.4 (CH$_2$), 19.8, 20.0, 20.3, 23.9 (d, J$_{CP}$=13.2 Hz), 24.6 (d, J$_{CP}$=13.2 Hz), 46.3 (d, J$_{CP}$=25.4 Hz, CH$_2$), 123.9 (dd, J$_{CP}$=3.7, 5.8 Hz, triazole-H), 147.4 (d, J$_{CP}$=11.1 Hz).

$^{31}$P NMR (CD$_3$OD) δ: 5.79 (s, 1P). 6.57 (s, 1P).

Mass spectroscopy (HRMS ESI): Measured mass (M+H)$^+$ 330.2240 (C$_{16}$H$_{34}$N$_3$P$_2$); Calculated mass 330.2228.

Using essentially the same procedures, the following compounds were obtained:

Deprotection of Compound 28: Compound 28 was obtained by converting the phosphine oxide and phosphine-borane complex of the protected form to phosphine groups, according to the above-described procedures.

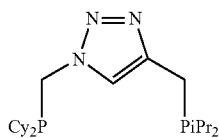

Compound 28

$^1$H NMR (C$_6$D$_6$) δ: 0.73-0.83 (m, 6H), 1.26-1.85 (br m, 24H), 2.99 (s, 2H, P—CH$_2$—C), 4.13 (d, J$_{HP}$=3.6 Hz, P—CH$_2$—N), 7.45 (s, 1H, triazole-H).

$^{13}$C NMR (C$_6$D$_6$) δ: 18.6 (d, J$_{CP}$=10.3 Hz), 19.0 (d, J$_{CP}$=20.4 Hz), 19.4 (d, J$_{CP}$=15.5 Hz), 22.8 (d, J$_{CP}$=14.0 Hz), 27.5 (d, J$_{CP}$=4.0 Hz), 27.6 (d, J$_{CP}$=7.0 Hz), 29.4 (d, J$_{CP}$=9.0 Hz), 30.3 (d, J$_{CP}$=14.0 Hz), 33.9 (d, J$_{CP}$=15.4 Hz), 44.9 (d, J$_{CP}$=25.7 Hz).

$^{31}$P NMR (C$_6$D$_6$) δ: 0.06 (s, 1P), 8.72 (s, 1P).

Mass spectroscopy (HRMS ESI): Measured mass (M+H)$^+$ 410.2880 (C$_{22}$H$_{42}$N$_3$P$_2$); Calculated mass 410.2854.

Deprotection of Compound 29: Compound 29 was obtained by converting the phosphine-borane complex of the protected form to a phosphine group, according to the above-described procedures.

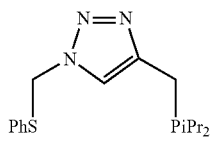

Compound 29

$^1$H NMR (C$_6$D$_6$) δ: 1.03-1.19 (m, 12H), 1.73-1.81 (m, 2H, CH), 2.95 (s, 2H, S—CH$_2$), 5.08 (d, J$_{HP}$=4.5 Hz, 2H, P—CH$_2$), 7.06-7.08 (m, 2H), 7.32-7.35 (m, 3H).

$^{13}$C NMR (C$_6$D$_6$) δ: 19.0, 19.1, 19.3 (CH$_2$), 19.9 (d, J$_{CP}$=15.4 Hz), 23.7 (d, J$_{CP}$=14.8 Hz), 52.7 (S—CH$_2$), 120.7, 128.1, 129.4, 131.8.

$^{31}$P NMR (C$_6$D$_6$) δ: 5.2.

Deprotection of Compound 30: Compound 30 was obtained by converting the phosphine-borane complex of the protected form to a phosphine group, according to the above-described procedures.

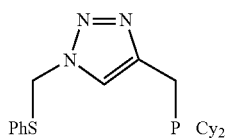

Compound 30

$^1$H NMR (C$_6$D$_6$) δ: 1.26-1.35 (m, 10H), 1.62-1.90 (m, 12H), 2.96 (s, 2H, CH$_2$—P), 4.96 (s, 2H, CH$_2$—S), 6.97-7.00 (m, 2H), 7.26-7.28 (m, 4H).

$^{13}$C NMR (C$_6$D$_6$) δ: 26.7, 27.5 (d, J$_{CP}$=7.5 Hz), 29.3 (d, J$_{CP}$=7.5 Hz), 30.3 (d, J$_{CP}$=15 Hz), 33.9 (d, J$_{CP}$=30 Hz), 52.7, 129.4, 131.7.

$^{31}$P NMR (C$_6$D$_6$) δ: −0.25.

Example 11

Palladium and Platinum Pincer Complexes Comprising a Dialkyl Phosphinyl Moiety

In order to examine the feasibility of the dialkylphosphine-containing pincer ligands to behave as tridentate ligands, the reactivity of a representative ligand (Compound 27) with a Pd precursor was explored. It was found that upon gentle heating a solution of Compound 27 with (TMEDA)PdCl$_2$ (TMEDA=tetramethylethylenediamine) in the presence of triethylamine, pincer complex 35 was formed, as shown in FIG. 9, and is further detailed hereinbelow. Following the reaction by $^{31}$P NMR showed complete and selective conversion of the starting ligand into the complex 35 after 18 hours. Compound 35 was fully characterized by multinuclear NMR techniques. The $^{31}$P NMR of 35 exhibits two doublets at 56.2 and 65.7 ppm with a coupling constant of 413 Hz characteristic to two non-equivalent phosphorus atoms located in mutual trans positions. The ipso-carbon resonates at 164.2 ppm, clearly demonstrating its bond to the metal.

Preparation of Compound 35:

Compound 35 was prepared by complexing palladium to Compound 27 using the procedures described in Example 4 (yield=77%).

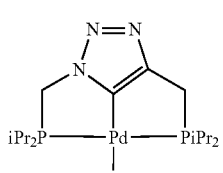

Compound 35

$^1$H NMR (CDCl$_3$) δ: 1.15-1.45 (m, 24H), 2.45-2.56 (m, 4H, CH), 2.90 (d, J$_{HP}$=8.7 Hz), 4.53 (d, J$_{HP}$=5.4 Hz).

$^{13}$C NMR (DMF-d$_7$) δ: 19.5 (dd, J$_{CP}$=2.1, 4.7 Hz), 19.8 (dd, J$_{CP}$=5.0, 12.0 Hz), 20.8 (d, J$_{CP}$=27.4 Hz), 25.9 (dd, J$_{CP}$=4.3, 17.5 Hz), 26.4 (dd, J$_{CP}$=4.3, 16.9 Hz), 45.8 (d, J$_{CP}$=29.8 Hz), 164.2 (C-ipso).

$^{31}$P NMR (CDCl$_3$) δ: 56.2 (d, J$_{PP}$=413 Hz, 1P), 65.7 (d, J$_{PP}$=413 Hz, 1P).

Mass spectroscopy (MS ESI): m/z=471.2 (M+1).

Preparation of Compound 37:

Compound 37 was prepared by complexing palladium to Compound 29. 0.032 mmol of Compound 29 was combined with 0.032 mmol (CH$_3$CN)$_2$PdCl$_2$ in 2 ml tetrahydrofuran (THF). The solvent was removed under reduced pressure and the crude residue was washed with diethyl ether (3×3 ml) and toluene (3×3 ml) and extracted with THF and dimethylformamide. The combined extracts were evaporated to give the product as a white solid (yield=100%).

After addition of palladium at room temperature, a yellow color appeared, indicating the formation of a bidentate complex, as described in Example 4. The presence of the bidentate intermediate was confirmed by X-ray analysis (data not shown).

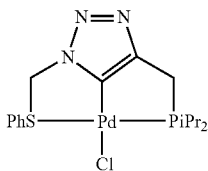

Compound 37

$^1$H NMR (DMF-d$_7$) δ: 8.50 (s, 1H, triazole-H), 8.03-8.01 (m, 2H), 7.87-7.84 (m, 3H), 7.74 (d, 2H), 7.55 (d, 2H), 7.43-7.40 (m, 2H), 7.30-7.27 (m, 2H), 6.34 (s, 2H, CH$_2$—S), 3.91 (s, 6H, O—CH$_3$), 3.80 (s, 2H, CH$_2$—P).

$^{13}$C{$^1$H} NMR (DMF-d$_7$) δ: 162.3, 138.4 (dd, J$_{CP}$=2.1, 4.7 Hz), 19.8 (dd, J$_{CP}$=5.0, 12.0 Hz), 20.8 (d, J$_{CP}$=27.4 Hz), 25.9 (d, J$_{CP}$=12 Hz), 136.6, 134.2, 133.3. 131.6 (d, J$_{CP}$=10 Hz), 130.3, 122.7 (d, J$_{CP}$=13 Hz), 114.1 (d, J$_{CP}$=5.0 Hz), 69.3 (s, CH$_2$—S), 57.7 (s, OCH$_3$), 25.8 (d, J$_{CP}$=108 Hz).

$^{31}$P{$^1$H} NMR (DMF-d$_7$) δ: 42.3 (d, J$_{PP}$=413 Hz, 1P), 65.7 (d, J$_{PP}$=413 Hz, 1P).

Elemental analysis: Calculated C, 45.99; H, 3.86; Found C, 44.99; H, 53.55.

Using essentially the same procedure, Compound 38 was prepared from Compound 30

Preparation of Compound 38:

Compound 38 was prepared by complexing palladium to Compound 30 using the procedures described above (yield=100%).

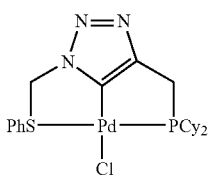

Compound 38

$^1$H NMR (DMF-d$_7$) δ: 8.45 (s, 1H, triazole-H), 7.37-7.52 (m, 5H, Ph), 6.17 (s, 2H, CH$_2$—S), 3.37 (d, J$_{HP}$=11.4 Hz, CH$_2$—P), 2.53-2.65 (m, 2H, CH), 1.44 (dd, J$_{HH}$=7.12 Hz, J$_{HP}$=18.3 Hz, 6H, CH$_3$), 1.17 (dd, J$_{HH}$=6.84 Hz, J$_{HP}$=16.7 Hz, 6H, CH$_3$).

$^{13}$C{$^1$H} NMR (DMF-d$_7$) δ: 149.4 (d, J$_{CP}$=7.05 Hz, C$_{Ar}$), 131.9, 129.4, 128.5, 123.3 (d, J$_{CP}$=12.5 Hz, C$_{Ar}$H), 54.9 (CH—S), 24.8 (d, J$_{CP}$=28.3 Hz, CH—CH$_3$), 17.8 (d, J$_{CP}$=28.3 Hz, CH$_2$—P), 17.4, 16.7.

$^{31}$P{$^1$H} NMR (DMF-d$_7$) δ: 83.4.

Elemental analysis: Calculated C, 38.53; H, 4.85; Found C, 39.84; H, 5.72.

Preparation of Compound 39:

The platinum analog of Compound 38 was formed by complexing platinum to Compound 30 using the procedures described in Example 4. After addition of platinum at room temperature, a bright yellow color appeared, indicating the formation of a bidentate complex, as described in Example 4. The presence of the bidentate intermediate was confirmed by X-ray analysis (data not shown).

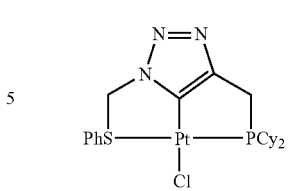

Compound 39

$^1$H NMR (DMF-d$_7$) δ: 8.55 (s, 1H, triazole-H), 7.68-7.56 (m, 5H, Ar), 6.30 (s, CH$_2$S), 3.36 (d, J$_{HP}$=10 Hz, CH$_2$—P), 2.52-2.33 (m, 4H), 1.94-1.45 (m, 18H).

$^{13}$C{$^1$H} NMR (DMF-d$_7$) δ: 151.6, 132.0, 131.9, 129.7, 123.2, 55.2, 27.0, 26.9, 26.3, 26.0, 25.9, 25.7.

$^{31}$P{$^1$H} NMR (DMF-d$_7$) δ: 46.11 (s, J$_{PPt}$=3482 Hz).

Elemental Analysis: Calculated C, 39.58; H, 4.83; Found C, 40.16; H, 5.13.

Mass spectroscopy (MS ESI): m/z=665.1035 (M+H)$^+$; calculated mass (C$_{22}$H$_{31}$N$_3$PSCl$_2$Pt) 665.1001.

Example 12

Catalytic Efficiency of Dialkylphosphine-Containing Pincer Complexes

The ligand influence of dialkylphosphine-containing pincer complexes on catalytic activity in the following reactions is examined.

Heck Reaction:

Various dialkylphosphine-containing pincer ligand-palladium complexes, such as are described above, are tested for their ability to catalyze a Heck reaction. Bromobenzene and methyl acrylate are reacted in the presence of each complex, as described in Example 6, and the yield and turnover number (TON) are determined. The efficacy of different complexes as catalysts may be compared in order to determine the effect of different types of ligand on efficacy.

Using similar procedures, the ligand influence of dialkylphosphine-containing pincer complexes on catalytic activity is determined for a Suzuki reaction, an allylic alkylation reaction, and a hydrogenation and/or dehydrogenation reaction.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A compound having a general Formula VIII:

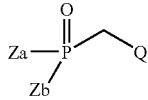

Formula VIII wherein:

Q is selected from the group consisting of azide; and at least one of Za and Zb is a substituted or non-substituted alkyl or a substituted or non-substituted cycloalkyl.

2. The compound of claim 1, wherein each of Za and Zb is independently selected from the group consisting of a substituted or non-substituted alkyl and a substituted or non-substituted cycloalkyl.

3. A compound having a general Formula VIII:

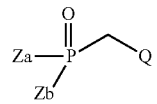

Formula VIII wherein:

Q is selected from the group consisting of azide, halide, carboxy, and hydroxy; and at least one of Za and Zb is a substituted or non-substituted branched-chain alkyl or a substituted or non-substituted cycloalkyl.

4. The compound of claim 3, wherein each of Za and Zb is independently selected from the group consisting of a substituted or non-substituted branched-chain alkyl and a substituted or non-substituted cycloalkyl.

* * * * *